(12) United States Patent
Neidhart et al.

(10) Patent No.: US 12,391,670 B2
(45) Date of Patent: Aug. 19, 2025

(54) FUNCTIONALIZED AMINOTRIAZINES

(71) Applicant: LEADXPRO AG, Villigen (CH)

(72) Inventors: Werner Neidhart, Villigen (CH); Denis Bucher, Villigen (CH)

(73) Assignee: LEADXPRO AG, Villigen (CH)

( * ) Notice: Subject to any disclaimer, the term of this patent is extended or adjusted under 35 U.S.C. 154(b) by 1051 days.

(21) Appl. No.: 17/287,467

(22) PCT Filed: Oct. 23, 2019

(86) PCT No.: PCT/EP2019/078789
§ 371 (c)(1),
(2) Date: Apr. 21, 2021

(87) PCT Pub. No.: WO2020/083957
PCT Pub. Date: Apr. 30, 2020

(65) Prior Publication Data
US 2021/0395225 A1 Dec. 23, 2021

(30) Foreign Application Priority Data
Oct. 24, 2018 (EP) ..................................... 18202231

(51) Int. Cl.
*C07D 401/14* (2006.01)
*C07D 401/04* (2006.01)
(Continued)

(52) U.S. Cl.
CPC .......... *C07D 401/14* (2013.01); *C07D 401/04* (2013.01); *C07D 405/14* (2013.01); *C07D 417/14* (2013.01)

(58) Field of Classification Search
CPC .. C07D 401/14; C07D 401/04; C07D 405/14; C07D 417/14; C07D 413/14; A61P 35/00
(Continued)

(56) References Cited

U.S. PATENT DOCUMENTS 7,790,728 B2* 9/2010 Vidal Juan .............. A61P 37/00
546/268.1
8,809,525 B2* 8/2014 Congreve ............ C07D 403/12
544/182
(Continued)

FOREIGN PATENT DOCUMENTS

CN 107406425 A 11/2017
WO 2001/080893 A1 11/2001
(Continued)

OTHER PUBLICATIONS

Congreve et al. J. Med. Chem. 2012, 55, 1898-1903, "Discovery of 1,2,4-Triazine Derivatives as Adenosine A2A Antagonists using Structure Based Drug Design" (Year: 2012).*
(Continued)

*Primary Examiner* — Amy L Clark
*Assistant Examiner* — Liyuan Mou
(74) *Attorney, Agent, or Firm* — MEDLER FERRO WOODHOUSE & MILLS PLLC

(57) ABSTRACT

The present invention relates to novel antagonists of the A2B adenosine receptor and pharmaceutical compositions comprising said antagonists as well as their uses for the treatment and prevention of disorders known to be susceptible to improvement by antagonism of the A2B receptor such as asthma, chronic obstructive pulmonary disorder (COPD), pulmonary fibrosis, vascular diseases, allergic diseases, hypertension, retinopathy, diabetes mellitus, inflammatory gastrointestinal tract disorders, inflammatory diseases, autoimmune diseases, renal diseases, neurological disorders and, in particular, cancers. In particular, the present invention relates to compounds of formula (I), wherein R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl; Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$dialkylamino$C_1$-$C_8$alkyl, $C_1$-$C_8$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_4$alkyl, $C_1$-$C_2$haloalkyl, $C_1$-$C_2$alkoxy; or Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by [one or more] substituents selected from halogen, cycloalkyl, $C_1$-$C_8$alkyl, $C_1$-$C_8$alkoxy, $C_1$-$C_8$hydroxalkyl and $C_1$-$C_8$alkoxyalkyl; Ar/Het is selected from pyridinyl, phenyl and oxazolyl wherein said pyridinyl, phenyl and oxazolyl is independently optionally substituted by one or more substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl; or pharmaceutically acceptable salt, or hydrate thereof.

(Continued)

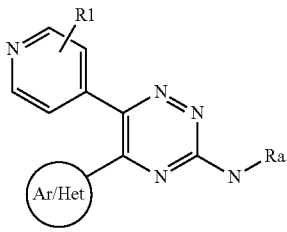

(I)

5 Claims, No Drawings

(51) Int. Cl.
 *C07D 405/14* (2006.01)
 *C07D 417/14* (2006.01)
(58) Field of Classification Search
 USPC .......................................................... 514/236
 See application file for complete search history.

(56) References Cited

U.S. PATENT DOCUMENTS

| | | | |
|---|---|---|---|
| 2009/0270416 A1 | 10/2009 | Boyle | |
| 2021/0230138 A1 | 7/2021 | Lu et al. | |

FOREIGN PATENT DOCUMENTS

| | | | | |
|---|---|---|---|---|
| WO | 2005/070926 | A1 | 8/2005 | |
| WO | 2006/113704 | A1 | 10/2006 | |
| WO | 2006/131835 | A2 | 12/2006 | |
| WO | 2007/017096 | A1 | 2/2007 | |
| WO | 2007/031440 | A2 | 3/2007 | |
| WO | WO-2011095625 | A1 * | 8/2011 | ......... A61K 31/4427 |
| WO | 2016/135048 | A1 | 9/2016 | |
| WO | 2016/150901 | A1 | 9/2016 | |
| WO | 2018/041771 | A1 | 3/2018 | |
| WO | 2018/054846 | A1 | 3/2018 | |
| WO | 2018/130184 | A1 | 7/2018 | |
| WO | 2019/158070 | A1 | 8/2019 | |

OTHER PUBLICATIONS

International Search Report in PCT/EP2019/078789, mailed Dec. 4, 2019.
Allard et al., "Targeting A2 adenosine receptors in cancer," Immunol. Cell Biol. 95:333-339 (2017).
Bahreyni, et al., "Role of adenosine signaling in the pathogenesis of breast cancer," J. Cell. Physiol. 233:1836-1843 (2018).
Figler et al., "Links between insulin resistance, adenosine $A_{2B}$ receptors, and inflammatory markers in mice and humans," Diabetes 60:669-679 (2011).
Iannone et al., "Blockade of $A_{2B}$ adenosine receptor reduces tumor growth and immune suppression mediated by myeloid-derived suppressor cells in a mouse model of melanoma," Neoplasia N. Y. N 15:1400-1409 (2013).
Ihara et al., "An in vivo screening system to identify tumorigenic genes," Oncogene 36:2023-2029 (2017).
Kalla and Zablocki, "Progress in the discovery of selective, high affinity $A_{2B}$ adenosine receptor antagonists as clinical candidates," Purinergic Signalling 5:21-29 (2009).
Kasama et al., "Adenosine $A_{2B}$ receptor promotes progression of human oral cancer," BMC Cancer 15:563 (2015).
Kuhn et al., "Intramolecular hydrogen bonding in medicinal chemistry," J. Med. Chem. 53:2601-261 (2010).
Ntantie et al., "An Adenosine-Mediated Signaling Pathway Suppresses Prenylation of the GTPase Rap1B and Promotes Cell Scattering," Sci. Signal. 6, ra39 (2013).
Ohta et al., "$A_{2A}$ adenosine receptor protects tumors from antitumor T cells," Proc. Natl. Acad. Sci. U.S.A. 103:13132-13137 (2006).
Peng et al., "Adenosine signaling contributes to ethanol-induced fatty liver in mice," J. Clin. Invest. 119:582-594 (2009).
Popoli et al., "Potential therapeutic relevance of adenosine $A_{2B}$ and $A_{2A}$ receptors in the central nervous system," CNS Neurol. Disord. Drug Targets 11:664-674 (2012). Abstract only.
Ryzhov et al., "Host $A_{2B}$ adenosine receptors promote carcinoma growth," Neoplasia N. Y. N 10:987-995 (2008).
Sun et al., "Role of $A_{2B}$ adenosine receptor signaling in adenosine-dependent pulmonary inflammation and injury," J. Clin. Invest. 116:2173-2182 (2006).
Sun and Huang, "Adenosine A2B Receptor: From Cell Biology to Human Diseases," Front. Chem. 4(37): 1-11 (2016).
Zablocki et al., "$A_{2B}$ adenosine receptor antagonists and their potential indications," Expert Opin. Ther. Pat. 16:1347-1357 (2006).
Zhou et al., "The adenosine $A_{2B}$ receptor promotes tumor progression of bladder urothelial carcinoma by enhancing MAPK signaling pathway," Oncotarget 8, 48755-48768 (2017).

* cited by examiner

FUNCTIONALIZED AMINOTRIAZINES

The present invention relates to novel antagonists of the A2B adenosine receptor and pharmaceutical compositions comprising said antagonists as well as their uses for the treatment and prevention of disorders known to be susceptible to improvement by antagonism of the A2B receptor such as asthma, chronic obstructive pulmonary disorder (COPD), pulmonary fibrosis, vascular diseases, allergic diseases, hypertension, retinopathy, diabetes mellitus, inflammatory gastrointestinal tract disorders, inflammatory diseases, autoimmune diseases, renal diseases, neurological disorders and, in particular, cancers.

RELATED ART

The listing or discussion of an apparently prior-published document in this specification should not necessarily be taken as an acknowledgement that the document is part of the state of the art or is common general knowledge.

Adenosine is an endogenous modulator of a number of physiological responses, which include vasodilation, pain, and inflammation. Adenosine receptors belong to the G-coupled signaling receptors, couple to different type of G proteins and mediate various signaling pathways in cells. Adenosine receptors are broadly expressed in normal tissues in four subtypes, namely A1, A2A, A2B and A3. The A2B receptor is found in many different cellular types, but it has traditionally elicited less interest than the A1, A2A, and A3 subtypes due to its low affinity for adenosine. The involvement of adenosine and in particular of the A2B receptor have, however, been demonstrated in processes such as interleukin secretion, $Ca^{2+}$ mobilization, hepatic glucose regulation, tumor vascularization, and cardio protection. Thus, the potential of adenosine A2B receptor antagonists as therapeutics have recently been suggested for various indications, such as for respiratory diseases, metabolic disorders, renal diseases, disorders and diseases associated with the central nervous system and in particular in oncology.

Thus, the adenosine-receptor pathway is considered a promising therapeutic target in cancer and immunocancer therapy, and adenosine signaling is believed and has been shown to regulate apoptosis, angiogenesis, metastasis, and immune suppression in cancer cells (D. Allard, et al., 2017, Immunol. Cell Biol. 95, 333-339; A. Bahreyni, et al., 2018, J. Cell. Physiol. 233, 1836-1843; A. Ohta, et al., 2006, Proc. Natl. Acad. Sci. U.S.A 103, 13132-13137). As indicated, the A2B receptor is found in many different cellular types, but it has traditionally elicited less interest than the A1, A2A, and A3 subtypes due to its low affinity for adenosine. However, the extracellular concentration of adenosine can increase significantly in the hypoxic tumor microenvironment leading to an activation of A2B receptors. In recent years, a link between A2B and cancer has emerged (H. Kasama, et al., 2015, BMC Cancer 15, 563). The tumor-promoting activity of A2B was first demonstrated in A2B-deficient mice, where tumor growth was decreased compared with wild-type counterparts. This effect was associated with a significant decrease in the intratumoral levels of vascular endothelial growth factor (VEGF) and limited amounts of tumor-infiltrating myeloid-derived suppressor cells (MDSCs) (S. Ryzhov et al., 2008, Neoplasia N. Y. N 10, 987-995). A2B was further found to induce tumor growth in lung, colon, and prostate cancers by producing basic fibroblast growth factor (bFGF), and A2B is moreover, known to play a role in the inflammatory response to the tumor. In addition, A2B has been shown to play a role in supporting invasion and metastatic spreading by the accumulation of non-prenylated Rap 1B, a small GTPase controlling cell adhesion (E. Ntantie et al., 2013, Sci. Signal. 6, ra39). Finally, A2B is involved in the regulation of dendritic cells and macrophages differentiation and function, which is crucial for tumor immune-surveillance. There is evidence that A2A inhibitors potentiate antitumor effects largely through the modulation of immune cell functions, such as enhancing the effector functions of cytotoxic lymphocytes and preventing the recruitment and polarization of immunosuppressive cell types in the tumor micro environment. By contrast, data suggest that the pro-tumor effects of A2B occur through both tumor-intrinsic and host-mediated pathways, and that A2B induces immunosuppression mainly via myeloid cells (R. Iannone, et al., 2013, Neoplasia N. Y. N 15, 1400-1409).

High A2B expression has been associated with poor prognosis in several cancers and the mean expression of A2B was found to be increased compared to the adjacent normal tissues in diverse human cancers, including ovarian, lung, liver, oral, colon and prostate cancers (T. Ihara, et al., 2017, Oncogene 36, 2023-2029). Importantly, the expression level of A2B was the highest among the four adenosine receptor subtypes in different ovarian and prostate cancer cell lines (Zhou, et al., 2017, Oncotarget 8, 48755-48768). The selective A2B agonist BAY 60-6583 enhanced melanoma progression in mice, while the selective A2B antagonist PSB 1115 suppressed melanoma growth (R. Iannone, et al., 2013, Neoplasia N. Y. N 15, 1400-1409). In oral squamous cell carcinoma, the A2B receptor was overexpressed and its silencing inhibited growth (H. Kasama, et al., 2015, BMC Cancer 15, 563). Numerous A2B antagonists are currently in development, in particular in oncology, but none has yet received regulatory approval.

In relation to respiratory diseases, A2B receptors mediate the production and release of pro-inflammatory mediators from mast cells, for example, IL-4, IL-8, IL-13, and histamine. Mice treated with A2B receptor antagonist have less pulmonary inflammation, less fibrosis and greater alveolar airspace enlargement than non-treated mice demonstrating the potential of A2B antagonists for reducing pulmonary inflammation in vivo (C.-X. Sun, et al., 2006, J. Clin. Invest. 116, 2173-2182). For this reason, A2B antagonists are considered as promising therapeutic agents in the treatment of respiratory diseases, such as pulmonary fibrosis, pulmonary hypertension (PH), obstructive pulmonary disease (COPD), and asthma (J. Zablocki, et al., 2006, Expert Opin. Ther. Pat. 16, 1347-1357).

Consistent with its anti-inflammatory and immunosuppressive effects, and are related to metabolic diseases, A2B has been found in different aspects of glucose regulation. For instance, A2B antagonists were found to decrease the inflammatory response and improve insulin resistance in a diabetic mouse strain by attenuating the production of IL-6 and other cytokines that influence glucose and fat metabolism (R. A. Figler, et al., 2011, Diabetes 60, 669-679). In addition, A2B antagonists proved to be able to prevent fatty liver formation post alcohol consumption in mice models (Z. Peng, et al., 2009. Adenosine signaling contributes to ethanol-induced fatty liver in mice. J. Clin. Invest. 119, 582-594).

In association with renal diseases, studies on mouse models have shown that A2B inhibition can protect against induced diabetic nephropathy and renal fibrosis. In addition, renal biopsy samples from patients and genetic and pharmacological approaches also supports a potential role for A2B inhibition in the treatment of chronic kidney disease (CKD) and renal ischemia (Y. Sun, et al., 2016, Front. Chem. 4).

The role of A2B antagonists in the central nervous system has attracted less attention than A2A inhibition. However, A2B is closely related to A2A receptors that have shown clear antiparkinsonian effects and are of great interest with respect to Alzheimer's disease, brain ischaemia, spinal cord injury, drug addiction and other conditions. The low affinity of A2B receptors for adenosine implies that they might represent a good therapeutic target, since they are activated only under pathological conditions when adenosine levels raise up to micromolar concentrations (P. Popoli, et al., 2012, CNS Neurol. Disord. Drug Targets 11, 664-674). The availability of safe and selective ligands for A2B receptors would allow exploration of such hypothesis.

Aminotriazines dual adenosine A2A, A1 receptors antagonists have been disclosed in WO2011/095625 and WO2018/130184. Moreover, several other compounds have been suggested as adenosine A2B receptor antagonists, namely pyrazine derivatives, in particular, for the treatment of asthma (WO2007/017096), derivatives of 2-amino pyridines (WO2016/135048), aminothiazoles (WO2005/070926) as well as thienouracil derivatives (WO2016/150901, WO2018/041771, WO2018/054846).

Although numerous A2B receptor antagonists are currently in development, none has yet received regulatory approval, and, thus, there is a need for novel antagonists of the A2B adenosine receptor, in particular for selective adenosine A2B receptor antagonists with respect to other adenosine receptor subtypes.

SUMMARY OF THE INVENTION

The present invention provides novel antagonists of the A2B adenosine receptor of formula I or a pharmaceutically acceptable salt, or a hydrate thereof, and their use as therapeutically active substances for the treatment or prevention of conditions, disorders or diseases, in particular, in the treatment or prevention of cancer. Moreover, the present invention provides processes for the manufacture of said compounds, intermediates as well as pharmaceutical compositions and medicaments containing said compounds or pharmaceutically acceptable salts, or hydrates thereof and, in addition, uses of the same for methods of prevention or treatment of disorders and diseases mediated by activation of adenosine A2B receptor.

In particular, the compounds of formula I, and, thus, the substituted and functionalized N-capped aminotriazines of the present invention represent highly selective adenosine A2B receptor antagonists, in particular, with respect to other adenosine receptor subtypes such as A2A, A1, and A3. Thus, the inventive compounds are uniquely suited for focused therapy ameliorating conditions driven by abnormally high adenosine A2B receptor signaling such as, in particular, in certain cancers. Moreover, the specific N-Cap substitution and functionalization, respectively, further provides particularly favorable properties such as solubility, cell permeation and lipophilicity allowing to tailor these properties, in particular, through the N-Cap functionality, while retaining its high A2B receptor potency and selectivity. It is believed, without being bound hereto, that the interplay between the polar triazine core and the N-cap allows to tailor further polarity and the formation of non-covalent intramolecular bonds between the polar triazine core and polar groups of N-Cap functionality, while retaining its high A2B receptor potency and selectivity. Such intramolecular H-bonds and, for example, sulfur sigma hole to lone pair triazine N interaction are, for example, beneficial for improving solubility and membrane permeation capabilities. As a consequence, the inventive compounds represent a new class of efficacious new therapeutics.

Thus, in a first aspect, the present invention provides compounds of formula I

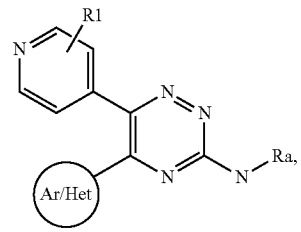

wherein
R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;
Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl and $C_1$-$C_8$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents selected from halogen, cycloalkyl, $C_1$-$C_8$alkyl, $C_1$-$C_8$alkoxy, $C_1$-$C_8$hydroxyalkyl and $C_1$-$C_8$alkoxyalkyl;
Ar/Het is selected from pyridinyl, phenyl and oxazolyl wherein said pyridinyl, phenyl and oxazolyl is independently optionally substituted by one or more, preferably one, substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;
or pharmaceutically acceptable salt, or hydrate thereof.

Thus, in another aspect, the present invention provides compounds of formula I

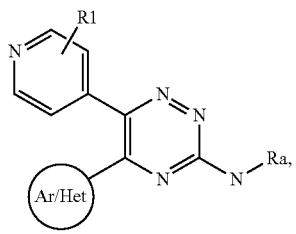

wherein
- R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;
- Ra is selected from phenyl or a heteroaryl, wherein said phenyl or said heteroaryl is optionally independently substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl and a heterocycle selected from oxiran, oxetane, aziridine and azetidine, wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents selected from halogen, cycloalkyl, $C_1$-$C_8$alkyl, $C_1$-$C_8$alkoxy, $C_1$-$C_8$hydroxalkyl and $C_1$-$C_8$alkoxyalkyl; wherein further preferably said heteroaryl is a 5- or 6-membered heteroaryl, wherein again further preferably said 5- or 6-membered heteroaryl is selected from pyridinyl, pyrimidinyl, thiazolyl, thiodiazolyl, oxazolyl, pyrazolyl and triazolyl;
- Ar/Het is selected from pyridinyl, phenyl and oxazolyl wherein said pyridinyl, phenyl and oxazolyl is independently optionally substituted by one or more, preferably one, substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;

or pharmaceutically acceptable salt, or hydrate thereof.

In another aspect, the present invention provides the inventive compound of formula I for use as a medicament.

In another aspect, the present invention provides a pharmaceutical composition comprising the inventive compound of formula I, optionally together with a pharmaceutically acceptable diluent or carrier.

In a further aspect, the present invention provides the inventive compound of formula I or the inventive pharmaceutical composition for use in a method of treating a condition, disorder or disease mediated by activation of the adenosine A2B receptor.

In a further aspect, the present invention provides the inventive compound of formula I or the inventive pharmaceutical composition for use in a method of treating a condition, disorder or disease ameliorated by the inhibition of the adenosine A2B receptor.

In a further aspect, the present invention provides the inventive compound of formula I or the inventive pharmaceutical composition for use in a method of treating a condition or disease susceptible to amelioration by antagonism of the adenosine A2B receptor.

In another aspect, the present invention provides the use of a compound of formula I according to the present invention in the manufacture of a medicament for the treatment of a condition, disorder or disease mediated by activation of the adenosine A2B receptor.

In another aspect, the present invention provides a method of treating a condition, disorder or disease mediated by activation of the adenosine A2B receptor comprising administering a therapeutically effective amount of a compound of formula I according to the present invention.

In another aspect, the present invention provides the inventive compound of formula I or the inventive pharmaceutical composition for use in a method of treating a condition, disorder or disease selected from a respiratory disease, an inflammatory obstructive airways disease, an inflammatory disease, a metabolic disease, a renal disease, a vascular disease, an allergic disease, an inflammatory gastrointestinal tract disorder, an autoimmune disease, a neurological disorder and a cancer.

In another aspect, the present invention provides the use of a compound of formula I according to the present invention in the manufacture of a medicament for the treatment of a condition, disorder or disease selected from a respiratory disease, an inflammatory obstructive airways disease, an inflammatory disease, a metabolic disease, a renal disease, a vascular disease, an allergic disease, an inflammatory gastrointestinal tract disorder, an autoimmune disease, a neurological disorder and a cancer.

In another aspect, the present invention provides a method of treating a condition, disorder or disease selected from a respiratory disease, an inflammatory obstructive airways disease, an inflammatory disease, a metabolic disease, a renal disease, a vascular disease, an allergic disease, an inflammatory gastrointestinal tract disorder, an autoimmune disease, a neurological disorder and a cancer, wherein said method comprises administering to a subject, particularly a human subject, in need thereof, a therapeutically effective amount of an inventive compound of formula I or a pharmaceutically acceptable salt, or hydrate thereof.

Further aspects and embodiments of the present invention will be become apparent as this description continues.

DETAILED DESCRIPTION OF THE INVENTION

Unless defined otherwise, all technical and scientific terms used herein have the same meanings as commonly understood by one of ordinary skill in the art to which this invention belongs. It is to be noted that for clarification the below definitions uses by way of example typically a "$C_1$-$C_8$-" fragment. Such usage is for definition purposes and is not intended to be limited hereto. The definitions for a lower or higher number of carbon atoms, for example a "$C_1$-$C_4$-" or a "$C_1$-$C_3$-" analogue are in accordance thereto.

"$C_1$-$C_8$-alkyl", as used herein, refers to straight chain or branched $C_1$-$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$-$C_8$-alkyl is $C_1$-$C_4$-alkyl.

"$C_1$-$C_8$-alkoxy", as used herein, refers to straight chain or branched $C_1$-$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$-$C_8$-alkoxy is $C_1$-$C_4$alkoxy.

"$C_1$-$C_8$-haloalkoxy", as used herein, refers to straight chain or branched $C_1$-$C_8$-alkoxy which is substituted by one or more halogen.

"Halogen", as used herein, refers to fluorine, chlorine, bromine or iodine; preferably it is fluorine or chlorine. This also applies, correspondingly, to halogen in combination with other meanings, such as haloalkyl.

"$C_1$-$C_8$-haloalkyl", as used herein, refers to $C_1$-$C_8$-alkyl as hereinbefore defined substituted by one or more halogen atoms, preferably one, two or three halogen atoms, preferably fluorine or chlorine atoms. Preferably, $C_1$-$C_8$-haloalkyl is $C_1$-$C_4$-alkyl substituted by one, two or three fluorine or chlorine atoms. Preferred examples include difluoromethyl, trifluoromethyl, chlorodifluoromethyl and 2,2,2-trifluoroethyl.

"$C_1$-$C_8$aminoalkyl", as used herein, refers to $C_1$-$C_8$-alkyl as hereinbefore defined substituted by one or more amino ($NH_2$) groups, preferably one, two or three amino ($NH_2$) groups, most preferably one amino ($NH_2$) group.

"$C_1$-$C_8$dialkylamino$C_1$-$C_8$alkyl", as used herein, refers to $C_1$-$C_8$-alkyl as hereinbefore defined substituted by one amino ($NH_2$) group which is substituted by two $C_1$-$C_8$-alkyl groups as hereinbefore defined, which may be the same or different. Preferably, said substitution of said $C_1$-$C_8$dialkylamino group is at the terminus of said $C_1$-$C_8$-alkyl.

"$C_1$-$C_8$hydroxyalkyl" as used herein, refers to $C_1$-$C_8$-alkyl as hereinbefore defined substituted by one or more hydroxyl (OH) groups, preferably one, two or three hydroxyl (OH) groups, most preferably one hydroxyl (OH) group.

"$C_1$-$C_8$alkylaminocarbonyl", as used herein, refers to $C_1$-$C_8$aminoalkyl as hereinbefore defined attached by a carbon atom to a carbonyl group.

The term "cycloalkyl", as used herein, refers to a mono- or bi-cyclic form, typically and preferably to a mono-cyclic form, and preferably contains 3 to 8 carbon atoms, more preferably 3 to 7 carbon atoms. Specific and preferred examples of monocyclic cycloalkyl groups include cyclopropyl, cyclobutyl and cyclohexyl. The term "$C_3$-$C_6$cycloalkyl", as used herein, refers to a monocyclic form containing 3 to 6 carbon atoms and specifically to cyclopropyl, cyclobutyl, cyclopentyl or cyclohexyl.

The term "aryl", as used herein, refers to a $C_6$-$C_{14}$ monocyclic or polycyclic aryl such as phenyl or naphthyl, anthranyl or phenanthryl, preferably to a $C_6$-$C_{14}$ monocyclic aryl, and most preferably to phenyl. When an aryl radical carries 2 or more substituents, the substituents may be the same or different.

The term "heteroaryl", as used herein, refers to a 5- to 14-membered ring system comprising at least one heteroaromatic ring and containing at least one heteroatom selected from O, S and N. A heteroaryl may be a single ring or two or more fused rings wherein at least one ring contains a heteroatom. Examples of monocyclic heteroaryl include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, triazolyl, imidazolidinyl and pyrazolyl.

In a preferred embodiment of the present invention, said heteroaryl is a 5- or 6-membered heteroaryl, wherein further preferably said 5- or 6-membered heteroaryl is selected from pyridinyl, pyrimidinyl, thiazolyl, thiodiazolyl, oxazolyl, pyrazolyl and triazolyl.

Where a group is said to be optionally substituted, preferably there are optionally 1-5 substituents, more preferably optionally 1-3 substituents, again more preferably optionally 1 or 2 substituents, and most preferably optionally 1 substituent. Where a group is said to be optionally substituted, and where there are more than one substituents for said optional substitution of said group, said more than one substituents can either be the same or different.

The term "treating", "treatment" or "therapy" as used herein refers to means of obtaining a desired physiological effect. The effect may be therapeutic in terms of partially or completely curing a disease or a condition and/or symptoms attributed to the disease or the condition. The term refers to inhibiting the disease or condition, i.e. arresting its development; or ameliorating the disease or condition, i.e. causing regression of the disease or condition.

As used herein, the term "for use" as used in "composition for use in treatment of a disease" shall disclose also the corresponding method of treatment and the corresponding use of a preparation for the manufacture of a medicament for the treatment of a disease".

A "therapeutically effective amount" is the amount of a compound or pharmaceutical composition in accordance with the present invention that will elicit the biological or medical response of a subject, preferably a human subject that is being sought by the researcher, veterinarian, medical doctor or other clinician. The term "therapeutic administration", as used herein, should refer to the administration of therapeutically effective amount.

Thus, in a first aspect, the present invention provides compounds of formula I

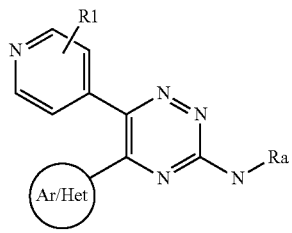

I wherein

R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;

Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents independently selected from halogen, cycloalkyl, $C_1$-$C_8$alkyl, $C_1$-$C_8$alkoxy, $C_1$-$C_8$hydroxalkyl and $C_1$-$C_8$alkoxyalkyl;

Ar/Het is selected from pyridinyl, phenyl and oxazolyl wherein said pyridinyl, phenyl and oxazolyl is independently optionally substituted by one or more, preferably one, substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;

or pharmaceutically acceptable salt, or hydrate thereof.

In a further preferred embodiment, said Ra is selected from phenyl, pyrimidinyl, pyridinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one substituent selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one substituent selected from halogen, cycloalkyl, $C_1$-$C_8$alkyl, $C_1$-$C_8$alkoxy, $C_1$-$C_8$hydroxyalkyl and $C_1$-$C_8$alkoxyalkyl.

In a further preferred embodiment, said Ar/Het is selected from pyridinyl, phenyl and oxazolyl wherein said pyridinyl, phenyl and oxazolyl is independently optionally substituted by one substituent selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl.

In a further preferred embodiment, said Ar/Het is selected from pyridinyl, phenyl and oxazolyl, wherein said pyridinyl, phenyl and oxazolyl is independently optionally substituted by one or more substituents independently selected from halogen, cyano, $C_1$-$C_4$alkyl, $C_1$-$C_4$haloalkyl, $C_1$-$C_4$alkoxy, $C_1$-$C_4$hydroxyalkyl and $C_1$-$C_4$alkoxyalkyl.

In a further preferred embodiment, said Ar/Het is selected from pyridinyl, phenyl and oxazolyl wherein said pyridinyl, phenyl and oxazolyl is independently optionally substituted by one substituent selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl.

In a further preferred embodiment, said Ar/Het is selected from pyridinyl, phenyl and oxazolyl wherein said pyridinyl, phenyl and oxazolyl is independently optionally substituted by one or more substituents independently selected from halogen and, $C_1$-$C_8$alkyl.

In a further very preferred embodiment, said Ar/Het is selected from pyridinyl, phenyl and oxazolyl wherein said pyridinyl, phenyl and oxazolyl is independently optionally substituted by one substituent selected from halogen and, $C_1$-$C_4$alkyl.

In a further very preferred embodiment, said Ar/Het is selected from pyridinyl, phenyl and oxazolyl wherein said pyridinyl, phenyl and oxazolyl is independently optionally substituted by one or more substituents independently selected from fluorine and methyl.

In a further very preferred embodiment, said Ar/Het is selected from pyridinyl, phenyl and oxazolyl wherein said pyridinyl, phenyl and oxazolyl is independently optionally substituted by one substituent selected from fluorine and methyl.

In a further very embodiment, said R1 represents 1 or 2 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl or $C_1$-$C_8$alkoxyalkyl. In a further very embodiment, said R1 represents 1 R1 substituent, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl or $C_1$-$C_8$alkoxyalkyl. In a further very embodiment, said R1 represents 1, 2 or 3 identical or different R1 substituents, wherein said R1 is independently at each occurrence selected from hydrogen, halogen, $C_1$-$C_4$alkyl, $C_1$-$C_4$haloalkyl, $C_1$-$C_4$alkoxy, $C_1$-$C_4$hydroxyalkyl or $C_1$-$C_4$alkoxyalkyl. In a further very embodiment, said R1 represents 1, 2 or 3 identical or different R1 substituents, wherein said R1 is independently at each occurrence selected from hydrogen, halogen, $C_1$-$C_2$alkyl, $C_1$-$C_2$haloalkyl, $C_1$-$C_2$alkoxy, $C_1$-$C_2$hydroxyalkyl or $C_1$-$C_2$alkoxyalkyl. In a further very embodiment, said R1 represents 1, 2 or 3 identical or different R1 substituents, wherein said R1 is independently at each occurrence selected from hydrogen, halogen, methyl, $C_1$-haloalkyl, methoxy or hydroxymethyl. In a further very embodiment, said R1 represents 1 or 2 identical or different R1 substituents, wherein said R1 is independently at each occurrence selected from hydrogen, halogen, $C_1$-$C_4$alkyl, $C_1$-$C_4$haloalkyl, $C_1$-$C_4$alkoxy, $C_1$-$C_4$hydroxyalkyl or $C_1$-$C_4$alkoxyalkyl. In a further very embodiment, said R1 represents 1 or 2 identical or different R1 substituents, wherein said R1 is independently at each occurrence selected from hydrogen, halogen, $C_1$-$C_2$alkyl, $C_1$-$C_2$haloalkyl, $C_1$-$C_2$alkoxy, $C_1$-$C_2$hydroxyalkyl or $C_1$-$C_2$alkoxyalkyl. In a further very embodiment, said R1 represents 1 or 2 identical or different R1 substituents, wherein said R1 is independently at each occurrence selected from hydrogen, halogen, methyl, $C_1$-haloalkyl, methoxy or hydroxymethyl.

It is to be noted that in case the number of R1 substituents is not specified when describing the R1 further herein—thus be it by way of example: 1 to 3 R1, or, 1 or 2 R1—then said reference to R1 should refer to compounds of the present invention containing solely one (1) R1 substituent.

In a further very preferred embodiment, said compound is a compound of formula Ia, formula Ib or formula Ic, wherein each of said R2 in said formula Ia, formula Ib or formula Ic represents 1 to 3 identical or different R2 substituents, wherein preferably said R2 is independently at each occurrence selected from hydrogen, $C_1$-$C_8$alkyl, $C_1$-$C_8$hydroxyalkyl, $C_1$-$C_8$haloalkyl, $C_1$-$C_8$alkoxyalkyl, halogen, cyano and $C_1$-$C_8$alkoxy.

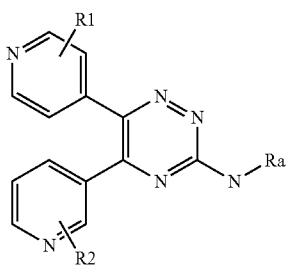

Ia

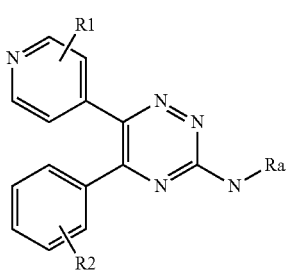

Ib

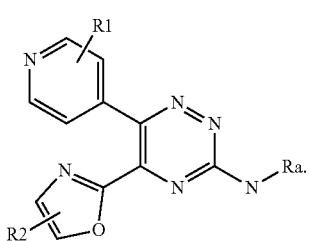

Ic

In a further very preferred embodiment, said compound is a compound of formula Ia, formula Ib or formula Ic, wherein each of said R2 in said formula Ia, formula Ib or formula Ic represents 1 or 2 identical or different R2 substituents, wherein preferably said R2 is independently at each occurrence selected from hydrogen, $C_1$-$C_8$alkyl, $C_1$-$C_8$hydroxyalkyl, $C_1$-$C_8$haloalkyl, $C_1$-$C_8$alkoxyalkyl, halogen, cyano and $C_1$-$C_8$alkoxy, wherein further preferably said R2 are independently at each occurrence selected from hydrogen, $C_1$-$C_4$alkyl, $C_1$-$C_4$hydroxyalkyl, $C_1$-$C_4$haloalkyl, $C_1$-$C_4$alkoxyalkyl, halogen, cyano and $C_1$-$C_4$alkoxy.

In a further very preferred embodiment, said compound is a compound of formula Ia, formula Ib or formula Ic, wherein each of said R2 in said formula Ia, formula Ib or formula Ic represents 2 identical or different R2 substituents, wherein preferably said R2 is independently at each occurrence selected from hydrogen, $C_1$-$C_8$alkyl, $C_1$-$C_8$hydroxyalkyl, $C_1$-$C_8$haloalkyl, $C_1$-$C_8$alkoxyalkyl, halogen, cyano and $C_1$-$C_8$alkoxy, wherein further preferably said R2 are independently at each occurrence selected from hydrogen, $C_1$-$C_4$alkyl, $C_1$-$C_4$hydroxyalkyl, $C_1$-$C_4$haloalkyl, $C_1$-$C_4$alkoxyalkyl, halogen, cyano and $C_1$-$C_4$alkoxy.

In a further very preferred embodiment, said compound is a compound of formula Ia, formula Ib or formula Ic, wherein each of said R2 in said formula Ia, formula Ib or formula Ic represents 1 R2 substituent, wherein preferably said R2 is independently at each occurrence selected from hydrogen, $C_1$-$C_8$alkyl, $C_1$-$C_8$hydroxyalkyl, $C_1$-$C_8$haloalkyl, $C_1$-$C_8$alkoxyalkyl, halogen, cyano and $C_1$-$C_8$alkoxy, wherein further preferably said R2 is independently at each occurrence selected from hydrogen, $C_1$-$C_4$alkyl, $C_1$-$C_4$hydroxyalkyl, $C_1$-$C_4$haloalkyl, $C_1$-$C_4$alkoxyalkyl, halogen, cyano and $C_1$-$C_4$alkoxy.

It is to be noted that in case the number of R2 substituents is not specified when describing the R2 further herein—thus be it by way of example: 1 to 3 R2, or, 1 or 2 R2-then said reference to R2 should refer to compounds of the present invention containing solely one (1) R2 substituent.

Thus, in a further very preferred embodiment, said compound is a compound of formula Ia, formula Ib or formula Ic, wherein R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, and R2 represents 1 to 3 identical or different R2 substituents, wherein said R2 is independently at each occurrence selected from hydrogen, $C_1$-$C_8$alkyl, halogen, cyano and $C_1$-$C_8$alkoxy, wherein preferably said R2 is independently at each occurrence selected from hydrogen, $C_1$-$C_4$alkyl, $C_1$-$C_4$hydroxyalkyl, halogen, cyano and $C_1$-$C_4$alkoxy.

Ia

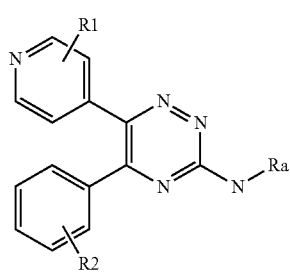

Ib

Ic

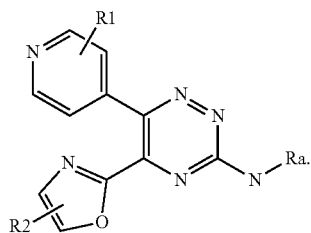

Thus, in a further very preferred embodiment, said compound is a compound of formula Ia, formula Ib or formula Ic, wherein R2 is independently selected from hydrogen, $C_1$-$C_8$alkyl, halogen, cyano and $C_1$-$C_8$alkoxy, wherein preferably said R2 is independently selected from hydrogen, $C_1$-$C_4$alkyl, $C_1$-$C_4$hydroxyalkyl, halogen, cyano and $C_1$-$C_4$alkoxy.

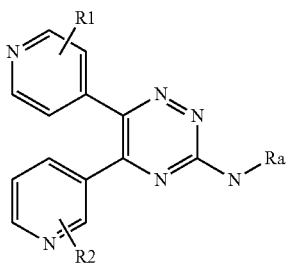

Ia

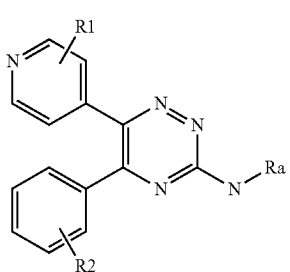

Ib

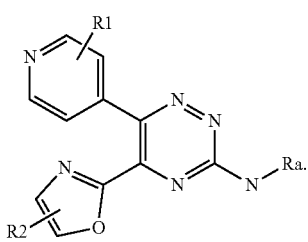

Ic

In a further very preferred embodiment of the present invention, said compound is a compound of formula Ia

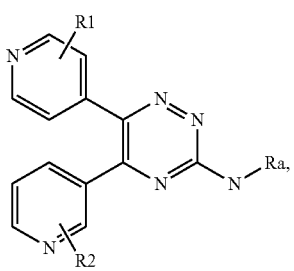

Ia wherein R2 is selected from hydrogen, $C_1$-$C_8$alkyl, halogen, cyano and $C_1$-$C_8$alkoxy, wherein preferably said R2 is independently selected from hydrogen, $C_1$-$C_4$alkyl, $C_1$-$C_4$hydroxyalkyl, halogen, cyano and $C_1$-$C_4$alkoxy.

In a further very preferred embodiment of the present invention, said compound is a compound of formula Ib

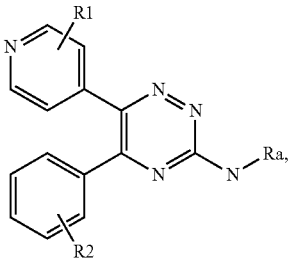

Ib wherein R2 is selected from hydrogen, $C_1$-$C_8$alkyl, $C_1$-$C_8$hydroxyalkyl, halogen, cyano and $C_1$-$C_8$alkoxy, wherein preferably said R2 is independently selected from hydrogen, $C_1$-$C_4$alkyl, $C_1$-$C_4$hydroxyalkyl, halogen, cyano and $C_1$-$C_4$alkoxy.

In a further very preferred embodiment of the present invention, said compound is a compound of formula Ic

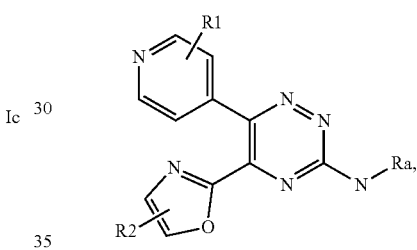

Ic wherein R2 is selected from hydrogen, $C_1$-$C_8$alkyl, $C_1$-$C_8$hydroxyalkyl, halogen, cyano and $C_1$-$C_8$alkoxy, wherein preferably said R2 is independently selected from hydrogen, $C_1$-$C_4$alkyl, $C_1$-$C_4$hydroxyalkyl, halogen, cyano and $C_1$-$C_4$alkoxy.

In a further preferred embodiment, said Ra is selected from phenyl, pyridinyl, pyrimidinyl thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more, preferably one, substituents independently selected from halogen, hydroxyl, cycloalkyl, $C_1$-$C_2$alkyl-substituted cycloalkyl, $C_1$-$C_4$alkyl, $C_1$-$C_4$haloalkyl, $C_1$-$C_4$alkoxy, $C_1$-$C_8$alkylaminocarbonyl, $C_1$-$C_4$hydroxyalkyl, $C_1$-$C_4$haloalkoxy, $C_1$-$C_4$dialkylamino$C_1$-$C_4$alkyl and $C_1$-$C_4$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or wherein Ra is —CONHR' wherein R' is selected from $C_1$-$C_4$alkyl, cycloalkyl, aryl, heteroaryl and $C_1$-$C_4$alkyl-N-morpholino, wherein said aryl, heteroaryl and $C_1$-$C_4$alkyl-N-morpholino is independently optionally substituted by one or more preferably one, substituents independently selected from halogen, cycloalkyl, $C_1$-$C_4$alkyl, $C_1$-$C_4$alkoxy, $C_1$-$C_4$hydroxalkyl and $C_1$-$C_4$alkoxyalkyl.

In a further preferred embodiment, said Ra is selected from phenyl, pyridinyl, pyrimidinyl thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more substituents independently selected from halogen, hydroxyl, cycloalkyl, $C_1$-$C_2$alkyl-substituted cycloalkyl, $C_1$-$C_4$alkyl, $C_1$-$C_4$haloalkyl, $C_1$-$C_4$alkoxy, $C_1$-$C_4$alkylaminocarbonyl, $C_1$-$C_4$hydroxyalkyl, $C_1$-$C_4$haloalkoxy, $C_1$-$C_4$dialkylamino$C_{1-2}$alkyl and $C_1$-$C_4$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or wherein Ra is —CONHR' wherein R' is selected from $C_1$-$C_4$alkyl, cycloalkyl, aryl, heteroaryl and $C_1$-$C_4$alkyl-N-morpholino, wherein said aryl and said heteroaryl is independently optionally substituted by one or more substituents independently selected from halogen, cycloalkyl, $C_1$-$C_4$alkyl, $C_1$-$C_4$alkoxy, $C_1$-$C_4$hydroxyalkyl and $C_1$-$C_4$alkoxyalkyl.

In a further preferred embodiment, said Ra is selected from phenyl, pyridinyl, pyrimidinyl thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one substituent independently selected from halogen, hydroxyl, cycloalkyl, $C_1$-$C_4$alkyl-substituted cycloalkyl, $C_1$-$C_4$alkyl, $C_1$-$C_4$haloalkyl, $C_1$-$C_4$alkoxy, $C_1$-$C_4$alkylaminocarbonyl, $C_1$-$C_4$hydroxyalkyl, $C_1$-$C_4$haloalkoxy, $C_1$-$C_4$dialkylamino$C_1$-$C_4$alkyl, $C_1$-$C_4$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or wherein Ra is —CONHR' wherein R' is selected from $C_1$-$C_4$alkyl, cycloalkyl, aryl, heteroaryl and $C_1$-$C_4$alkyl-N-morpholino, wherein said aryl and said heteroaryl is independently optionally substituted by one substituent independently selected from halogen, cycloalkyl, $C_1$-$C_4$alkyl, $C_1$-$C_4$alkoxy, $C_1$-$C_4$hydroxyalkyl and $C_1$-$C_4$alkoxyalkyl.

In a further preferred embodiment, said Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more substituents independently selected from halogen, hydroxyl, cycloalkyl, $C_1$-$C_2$alkyl-substituted cycloalkyl, $C_1$-$C_4$alkyl, $C_1$-$C_2$haloalkyl, $C_1$-$C_2$alkoxy, $C_1$-$C_2$alkylaminocarbonyl, $C_1$-$C_4$hydroxyalkyl, $C_1$-$C_2$haloalkoxy, $C_1$-$C_2$dialkylamino$C_1$-$C_2$alkyl $C_1$-$C_2$aminoalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy; or wherein Ra is —CONHR' wherein R' is selected from $C_1$-$C_2$alkyl, cycloalkyl, aryl, heteroaryl and $C_1$-$C_2$alkyl-N-morpholino, wherein said aryl and said heteroaryl is independently optionally substituted by one or more substituents independently selected from halogen, $C_1$-$C_2$alkyl, $C_1$-$C_2$alkoxy, $C_1$-$C_2$hydroxalkyl and $C_1$-$C_2$alkoxyalkyl.

In a further preferred embodiment, said Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one substituent independently selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_2$haloalkyl, $C_1$-$C_2$alkoxy, $C_1$-$C_2$alkylaminocarbonyl, $C_1$-$C_4$hydroxyalkyl, $C_1$-$C_2$haloalkoxy, $C_1$-$C_2$dialkylamino$C_1$-$C_2$alkyl, $C_1$-$C_2$aminoalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy; or wherein Ra is —CONHR' wherein R' is selected from $C_1$-$C_2$alkyl, $C_3$-$C_6$cycloalkyl, aryl, heteroaryl and $C_1$-$C_2$alkyl-N-morpholino, wherein said aryl and said heteroaryl is independently optionally substituted by one substituent independently selected from halogen, $C_3$-$C_6$cycloalkyl, $C_1$-$C_2$alkyl, $C_1$-$C_2$alkoxy, $C_1$-$C_2$hydroxalkyl and $C_1$-$C_2$alkoxyalkyl.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one or more substituents independently selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_4$haloalkyl, $C_1$-$C_4$alkoxy, $C_1$-$C_4$hydroxyalkyl, $C_1$-$C_2$haloalkoxy, $C_1$-$C_4$dialkylamino$C_1$-$C_4$alkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_4$alkyl, $C_3$-$C_6$cycloalkyl, aryl, heteroaryl and $C_1$-$C_4$alkyl-N-morpholino, wherein said aryl and said heteroaryl is independently optionally substituted by one or more substituents independently selected from halogen, $C_3$-$C_6$cycloalkyl and $C_1$-$C_4$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent independently selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_4$alkoxy, $C_1$-$C_4$alkoxyalkyl, $C_1$-$C_4$hydroxyalkyl, $C_1$-$C_2$haloalkoxy, $C_1$-$C_4$dialkylamino$C_1$-$C_4$alkyl, $C_1$-$C_4$haloalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_4$alkyl, $C_3$-$C_6$cycloalkyl, aryl, heteroaryl and $C_1$-$C_4$alkyl-N-morpholino, wherein said aryl and said heteroaryl is independently optionally substituted by one substituent independently selected from halogen, $C_3$-$C_6$cycloalkyl and $C_1$-$C_4$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one or more substituents independently selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_2$alkoxy, $C_1$-$C_2$alkoxyalkyl, $C_1$-$C_4$hydroxyalkyl, $C_1$-$C_2$haloalkoxy, $C_1$-$C_2$dialkylamino$C_1$-$C_2$alkyl, $C_1$-$C_2$haloalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_2$alkyl, $C_3$-$C_6$cycloalkyl, aryl, heteroaryl and $C_1$-$C_2$alkyl-N-morpholino, wherein said aryl and said heteroaryl is independently optionally substituted by one or more substituents independently selected from halogen, $C_3$-$C_6$cycloalkyl, and $C_1$-$C_2$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent independently selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_2$alkoxy, $C_1$-$C_2$alkoxyalkyl, $C_1$-$C_4$hydroxyalkyl, $C_1$-$C_2$haloalkoxy, $C_1$-$C_2$dialkylamino$C_1$-$C_2$alkyl, $C_1$-$C_2$haloalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_2$alkyl, $C_3$-$C_6$cycloalkyl, aryl, heteroaryl and $C_1$-$C_2$alkyl-N-morpholino, wherein said aryl and said heteroaryl is independently optionally substituted by one substituent independently selected from halogen $C_3$-$C_6$cycloalkyl and $C_1$-$C_2$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one or more substituents independently selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_2$alkoxy, $C_1$-$C_2$alkoxyalkyl, $C_1$-$C_4$hydroxyalkyl, $C_1$-$C_2$haloalkoxy, $C_1$-$C_2$dialkylamino$C_1$-$C_2$alkyl, $C_1$-$C_2$haloalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_2$alkyl, $C_3$-$C_6$cycloalkyl, aryl and $C_1$-$C_2$alkyl-N-morpholino, wherein said aryl is independently optionally substituted by one or more substituents independently selected from halogen, $C_3$-$C_6$cycloalkyl and $C_1$-$C_2$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent independently selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_2$alkoxy, $C_1$-$C_2$alkoxyalkyl, $C_1$-$C_4$hydroxyalkyl, $C_1$-$C_2$haloalkoxy, $C_1$-$C_2$dialkylamino$C_1$-$C_2$alkyl, $C_1$-$C_2$haloalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_2$alkyl, $C_3$-$C_6$cycloalkyl, aryl and $C_1$-$C_2$alkyl-N-morpholino, wherein said aryl is independently optionally substituted by one substituent independently selected from halogen, $C_3$-$C_6$cycloalkyl and $C_1$-$C_2$alkoxy.

In a further very preferred embodiment, said Ra is selected from the group consisting of

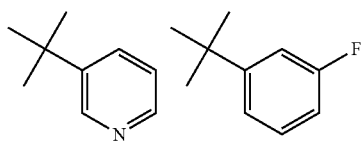

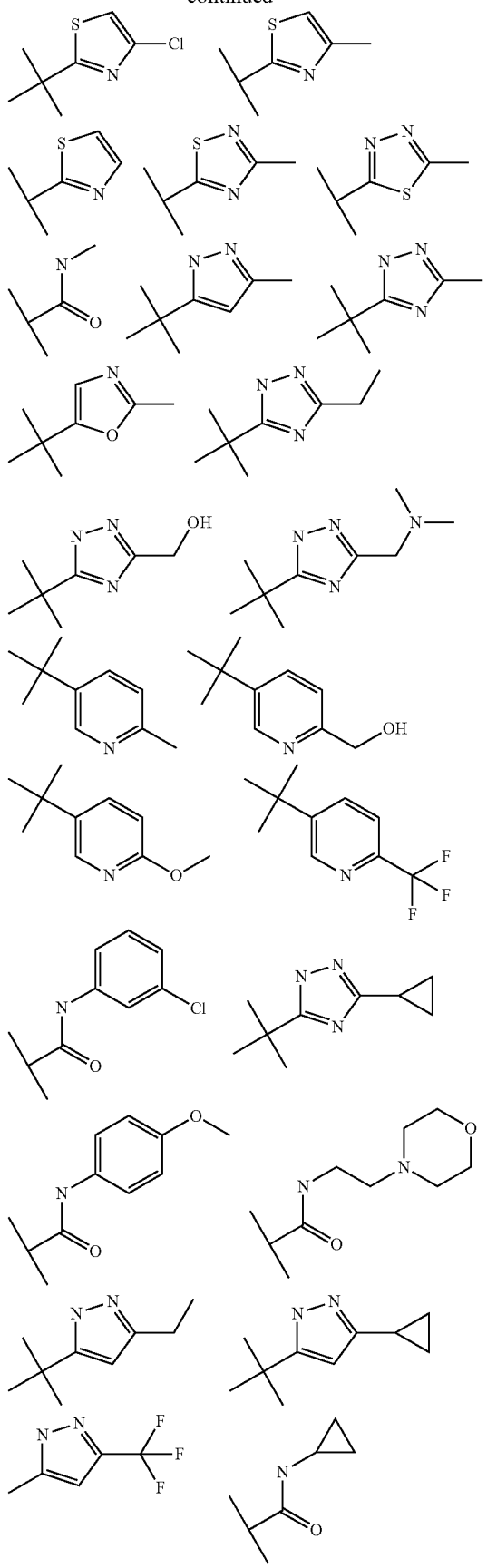

-continued

In a further very preferred embodiment, said Ra is selected from phenyl, pyridinyl, pyrimidinyl, thiazolyl, thiodiazolyl, oxazolyl, pyrazolyl and thiazolyl and wherein said phenyl, pyridinyl, thiazolyl, thiodiazolyl, oxazolyl, pyrazolyl and thiazolyl is independently optionally substituted by one or more substituents selected from halogen, hydroxyl, $C_3$-$C_6$cycloalkyl, $C_1$-$C_2$alkyl-substituted $C_3$-$C_6$cylcoalkyl, $C_1$-$C_4$alkyl, $C_1$-$C_4$alkoxy, $C_1$-$C_4$haloalkyl, $C_1$-$C_4$hydroxyalkyl, $C_1$-$C_2$haloalkoxy, $C_1$-$C_4$dialkylamino$C_1$-$C_4$alkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one or more substituents selected from halogen, hydroxyl, $C_3$-$C_6$Cycloalkyl, $C_1$-$C_2$alkyl-substituted $C_3$-$C_6$Cycloalkyl, $C_1$-$C_4$alkyl, $C_1$-$C_4$alkoxy, $C_1$-$C_4$haloalkyl, $C_1$-$C_4$hydroxyalkyl, $C_1$-$C_2$haloalkoxy, $C_1$-$C_4$dialkylamino$C_1$-$C_4$alkyl, and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one or more substituents selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_2$alkoxy, $C_1$-$C_2$haloalkyl, $C_1$-$C_4$hydroxyalkyl, $C_1$-$C_2$haloalkoxy, $C_1$-$C_2$dialkylamino$C_1$-$C_2$alkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent selected from halogen, hydroxyl, $C_3$-$C_6$cycloalkyl, $C_1$-$C_2$alkyl-substituted $C_3$-$C_6$cycloalkyl, $C_1$-$C_4$alkyl, $C_1$-$C_2$alkoxy, $C_1$-$C_2$haloalkyl, $C_1$-$C_4$hydroxyalkyl, $C_1$-$C_2$haloalkoxy, $C_1$-$C_2$dialkylamino$C_1$-$C_2$alkyl, oxetane and oxetane substituted by halogen, hydroxyl, $C_1$-$C_2$alkyl, $C_1$-$C_2$haloalkyl, $C_1$-$C_2$alkoxy.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one or more substituents selected from F, Cl, hydroxyl, cyclopropyl, methyl-substituted cyclopropyl, hydroxy-substituted oxetane, methoxy, $CF_3$, $OCH_2CHF_2$, hydroxymethyl, $C(CH_3)_2OH$, $CH(CH_3)OH$, $CH[CH(CH_3)_2]OH$, dimethylaminomethyl, methyl, ethyl, iso-propyl and tert-butyl.

In a further very preferred embodiment, said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent selected from F, Cl, hydroxyl, cyclopropyl, methyl-substituted cyclopropyl, hydroxy-substituted oxetane, methoxy, $CF_3$, $OCH_2CHF_2$, hydroxymethyl, $C(CH_3)_2OH$, $CH(CH_3)OH$, $CH[CH(CH_3)_2]OH$, dimethylaminomethyl, methyl, ethyl, iso-propyl and tert-butyl.

In a further very preferred embodiment, said Ra is selected from the group consisting of

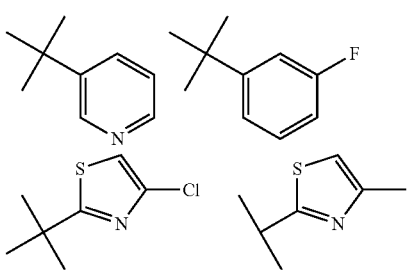

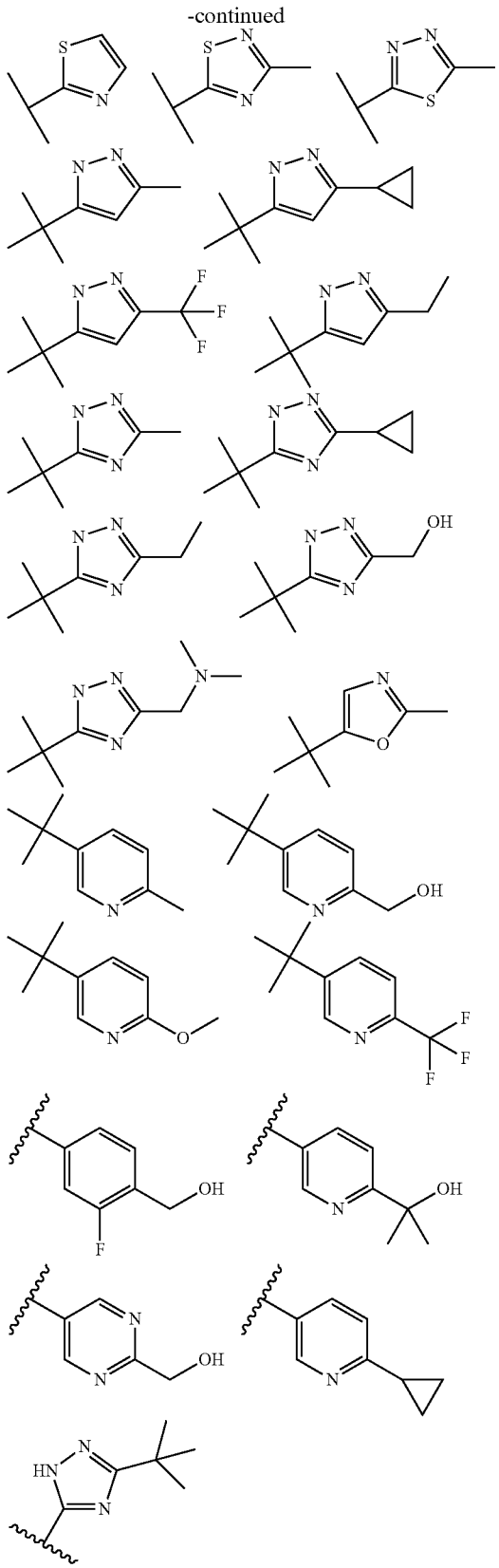

In a further very preferred embodiment, said Ra is —CONHR' wherein R' is selected from $C_1$-$C_4$alkyl, aryl and $C_1$-$C_4$alkyl-N-morpholino, wherein said aryl is optionally substituted by one or more substituents independently selected from halogen, $C_1$-$C_4$alkyl and $C_1$-$C_4$alkoxy.

In a further very preferred embodiment, said Ra is —CONHR' wherein R' is selected from $C_1$-$C_4$alkyl, aryl and $C_1$-$C_4$alkyl-N-morpholino, wherein said aryl is optionally substituted by one substituent independently selected from halogen, $C_1$-$C_4$alkyl and $C_1$-$C_4$alkoxy.

In a further very preferred embodiment, said Ra is —CONHR' wherein R' is selected from $C_1$-$C_2$alkyl, aryl and $C_1$-$C_2$alkyl-N-morpholino, wherein said aryl is optionally substituted by one or more substituents independently selected from halogen, $C_1$-$C_2$alkyl and $C_1$-$C_2$alkoxy.

In a further very preferred embodiment, said Ra is —CONHR' wherein R' is selected from $C_1$-$C_2$alkyl, aryl and $C_1$-$C_2$alkyl-N-morpholino, wherein said aryl is optionally substituted by one substituent independently selected from halogen, $C_1$-$C_2$alkyl and $C_1$-$C_2$alkoxy.

In a further very preferred embodiment, said Ra is —CONHR' wherein R' is selected from methyl, phenyl, and ethyl-N-morpholino, wherein said phenyl is optionally substituted by one or more substituents independently selected from C and methoxy.

In a further very preferred embodiment, said Ra is —CONHR' wherein R' is selected from methyl, phenyl, and ethyl-N-morpholino, wherein said phenyl is optionally substituted by one substituent independently selected from C and methoxy.

In a further very preferred embodiment, said Ra is selected from the group consisting of

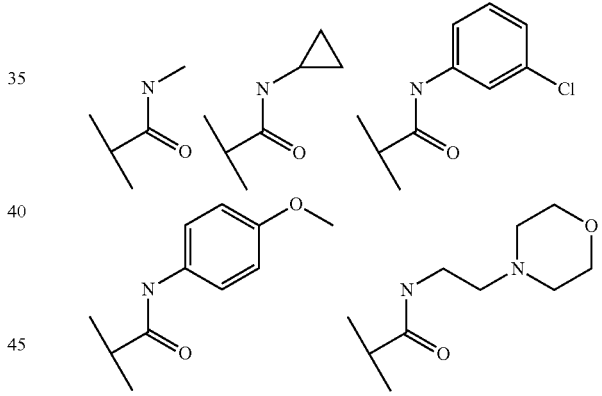

In a further very preferred embodiment, said R1 is selected from hydrogen, halogen, $C_1$-$C_4$alkyl, $C_1$-$C_4$haloalkyl, $C_1$-$C_4$alkoxy, $C_1$-$C_4$hydroxyalkyl and $C_1$-$C_4$alkoxyalkyl.

In a further very preferred embodiment, said R1 is selected from hydrogen, halogen, $C_1$-$C_2$alkyl, $C_1$-$C_2$haloalkyl, $C_1$-$C_2$alkoxy, $C_1$-$C_2$hydroxyalkyl and $C_1$-$C_2$alkoxyalkyl.

In a further very preferred embodiment, said R1 is selected from hydrogen, halogen, $C_1$-$C_2$alkyl and $C_1$-$C_2$haloalkyl. In a further very preferred embodiment, said R1 is selected from hydrogen, F, Cl, $CH_3$ and $CF_3$. In a further very preferred embodiment, said R1 is selected from hydrogen, F and $CF_3$. In a further very preferred embodiment, said R1 is selected from hydrogen, F and $CH_3$. In a further very preferred embodiment, said R1 is H.

In a further very preferred embodiment, said R1 is F, and wherein preferably said F is at the ortho-position relative to the point of attachment to the triazine ring.

In a further very preferred embodiment, said R1 is CF$_3$, and wherein preferably said CF$_3$ is at the meta-position relative to the point of attachment to the triazine ring.

In a further very preferred embodiment, said R1 is CH$_3$, and wherein preferably said CH$_3$ is at the meta-position relative to the point of attachment to the triazine ring.

In a further very preferred embodiment, said R1 is selected from halogen, C$_1$-C$_4$haloalkyl, and hydrogen; and said Ra is selected from phenyl, pyridinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by substituents selected from halogen, C$_1$-C$_4$alkyl and C$_1$-C$_4$haloalkyl; or Ra is —CONHR' wherein R' is C$_1$-C$_4$alkyl; and said Ar/Het is selected from pyridinyl, phenyl and oxazolyl wherein said pyridinyl, phenyl and oxazolyl is independently optionally substituted by substituents selected from halogen and, C$_1$-C$_4$alkyl.

In a further very preferred embodiment, said R1 is selected from F, CF$_3$, and hydrogen; Ra is selected from phenyl, pyridinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by substituents selected from F, methyl and CF$_3$; or Ra is —CONHR' wherein R' is methyl; Ar/Het is selected from pyridinyl, phenyl and oxazolyl wherein said pyridinyl, phenyl and oxazolyl is independently optionally substituted by substituents selected from F and methyl.

In a further very preferred embodiment, said R1 is selected from hydrogen, F and CF$_3$, and said Ra is selected from phenyl, pyridinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more substituents selected from hydrogen, halogen, C$_1$-C$_4$alkyl, C$_1$-C$_4$haloalkyl, C$_1$-C$_4$alkoxy, C$_1$-C$_4$alkylaminocarbonyl, C$_1$-C$_4$hydroxyalkyl, C$_1$-C$_4$dialkylaminoalkyl and C$_1$-C$_4$aminoalkyl; or Ra is —CONHR' wherein R' is selected from C$_1$-C$_4$alkyl, aryl, heteroaryl and C$_1$-C$_4$alkyl-N-morpholino wherein said aryl, heteroaryl and C$_1$-C$_4$alkyl-N-morpholino is independently optionally substituted by one or more substituents selected from hydrogen, halogen, C$_1$-C$_4$alkyl, C$_1$-C$_4$alkoxy, C$_1$-C$_4$hydroxalkyl and C$_1$-C$_4$alkoxyalkyl; and said Ar/Het is selected from pyridinyl, phenyl and oxazolyl wherein said pyridinyl, phenyl and oxazolyl is independently optionally substituted by one or more substituents selected from halogen, cyano, C$_1$-C$_4$alkyl, C$_1$-C$_4$haloalkyl, C$_1$-C$_4$alkoxy, C$_1$-C$_4$hydroxyalkyl and C$_1$-C$_4$alkoxyalkyl.

In a further very preferred embodiment, said compound is a compound of formula Ia, formula Ib or formula Ic,

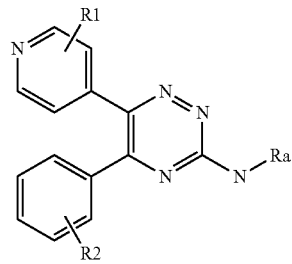

Ib

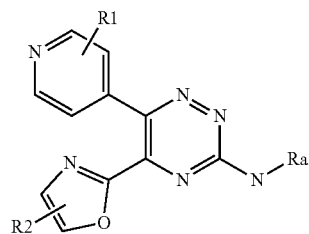

Ic wherein each of said R2 in said formula Ia, formula Ib or formula Ic represents 1 or 2 identical or different R2 substituents, wherein said R2 is independently at each occurrence selected from hydrogen, C$_1$-C$_4$alkyl, C$_1$-C$_4$hydroxyalkyl, halogen, cyano and C$_1$-C$_4$alkoxy.

In a further very preferred embodiment, said compound is a compound of formula Ia, formula Ib or formula Ic, wherein each of said R2 in said formula Ia, formula Ib or formula Ic represents 1 R2 substituent, and wherein R2 is independently selected from hydrogen, C$_1$-C$_4$alkyl, halogen and C$_1$-C$_4$alkoxyl.

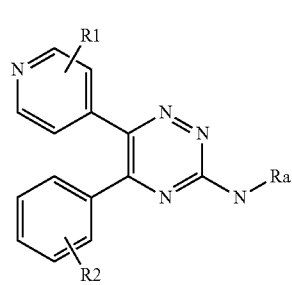

Ia

Ib

-continued

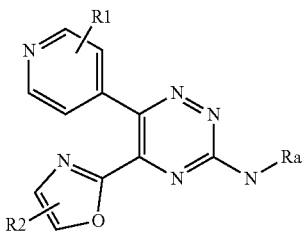

Ic

In a further very preferred embodiment, said R2 is selected from hydrogen, $C_1$-$C_2$alkyl, $C_1$-$C_2$hydroxyalkyl, halogen and $C_1$-$C_2$alkoxyl.

In a further very preferred embodiment, said compound is a compound of formula Ia, formula Ib or formula Ic, wherein each of said R2 in said formula Ia, formula Ib or formula Ic represents 1 or 2 identical or different R2 substituents, wherein said R2 is independently at each occurrence selected from hydrogen, $C_1$-$C_2$alky, $C_1$-$C_2$hydroxyalkyl and halogen.

In a further very preferred embodiment, said compound is a compound of formula Ia, formula Ib or formula Ic, wherein each of said R2 in said formula Ia, formula Ib or formula Ic represents 1 R2 substituent, and wherein said R2 is selected from hydrogen, $C_1$-$C_2$alkyl, $C_1$-$C_2$hydroxyalkyl and halogen.

In a further very preferred embodiment, said compound is a compound of formula Ia, formula Ib or formula Ic, wherein each of said R2 in said formula Ia, formula Ib or formula Ic represents 1 or 2 identical or different R2 substituents, wherein said R2 is independently at each occurrence selected from hydrogen, F, hydroxymethyl, and methyl.

In a further very preferred said compound is a compound of formula Ia, formula Ib or formula Ic, and wherein said R2 is selected from hydrogen, F and methyl.

In a further very preferred embodiment, said compound is a compound of formula Ia

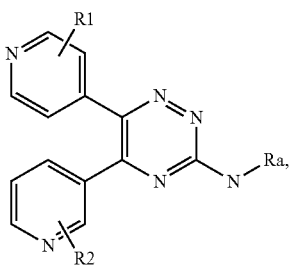

Ia wherein
said R1 is selected from hydrogen, halogen and $C_1$-$C_2$haloalkyl;
said R2 is selected from hydrogen, $C_1$-$C_2$alkyl, $C_1$-$C_2$hydroxyalkyl and halogen; and said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent independently selected from halogen, hydroxyl, $C_3$-$C_6$cycloalkyl, $C_1$-$C_2$alkyl-substituted cycloalkyl, $C_1$-$C_4$alkyl, $C_1$-$C_2$alkoxy, $C_1$-$C_2$alkoxyalkyl, $C_1$-$C_4$hydroxyalkyl, $C_1$-$C_2$haloalkoxy, $C_1$-$C_2$dialkylamino$C_1$-$C_2$alkyl, $C_1$-$C_2$haloalkyl and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_2$alkyl. $C_3$-$C_6$cycloalkyl, aryl and $C_1$-$C_2$alkyl-N-morpholino, wherein said aryl is independently optionally substituted by one substituent independently selected from halogen, $C_3$-$C_6$cycloalkyl and $C_1$-$C_2$alkoxy. In a further very preferred embodiment, said compound is a compound of formula Ia, and said R1 is hydrogen.

In a further very preferred embodiment, said compound is a compound of formula Ib

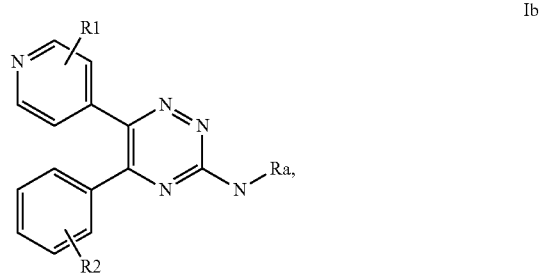

Ib wherein
said R1 is selected from hydrogen, halogen and $C_1$-$C_2$haloalkyl;
said R2 is selected from hydrogen, $C_1$-$C_2$alky and halogen; and
said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent independently selected from halogen, hydroxyl, $C_3$-$C_6$cycloalkyl, $C_1$-$C_2$alkyl-substituted cycloalkyl, $C_1$-$C_4$alkyl, $C_1$-$C_2$alkoxy, $C_1$-$C_2$alkoxyalkyl, $C_1$-$C_4$hydroxyalkyl, $C_1$-$C_2$haloalkoxy, $C_1$-$C_2$dialkylamino$C_1$-$C_2$alkyl $C_1$-$C_2$haloalkyl, and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy, or wherein Ra is —CONHR' wherein R' is selected from $C_1$-$C_2$alkyl, $C_3$-$C_6$cycloalkyl, aryl and $C_1$-$C_2$alkyl-N-morpholino, wherein said aryl is independently optionally substituted by one substituent independently selected from halogen, $C_3$-$C_6$cycloalkyl and $C_1$-$C_2$alkoxy. In a further very preferred embodiment, said compound is a compound of formula Ia, and said R1 is hydrogen.

In a further very preferred embodiment, said compound is a compound of formula Ib, and wherein said R2 is F, and wherein preferably said F is at the ortho-position relative to the point of attachment to the triazine ring.

In a further very preferred embodiment, said compound is a compound of formula Ic

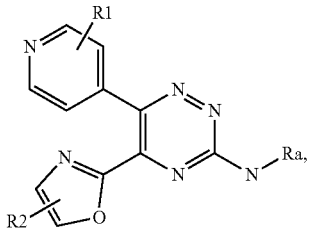

Ic wherein
said R1 is selected from hydrogen, halogen and $C_1$-$C_2$haloalkyl;
said R2 is selected from hydrogen, $C_1$-$C_2$alky and halogen; and
said Ra is selected from phenyl, pyridinyl, pyrimidinyl, thiazolyl, thiodiazolyl, oxazolyl, pyrazolyl and triazolyl and wherein said phenyl, pyridinyl, thiazolyl, thiodiazolyl, oxazolyl, pyrazolyl and triazolyl is independently optionally substituted by one substituent independently selected from halogen, hydroxyl, $C_3$-$C_6$cycloalkyl, $C_1$-$C_2$alkyl-substituted cycloalkyl, $C_1$-$C_4$alkyl, $C_1$-$C_2$alkoxy, $C_1$-$C_2$alkoxyalkyl, $C_1$-$C_4$hydroxyalkyl, $C_1$-$C_2$haloalkoxy, $C_1$-$C_2$dialkylamino$C_1$-$C_2$alkyl, $C_1$-$C_2$haloalkyl a and a heterocycle selected from oxetane and azetidine wherein said oxetane and said azetidine are independently optionally substituted by halogen, hydroxyl, $C_1$-$C_2$alkyl, $C_1$-$C_2$haloalkyl, $C_1$-$C_2$alkoxy; or wherein Ra is —CONHR' wherein R' is selected from $C_1$-$C_2$alkyl, $C_3$-$C_6$cycloalkyl, aryl and $C_1$-$C_2$alkyl-N-morpholino, wherein said aryl is independently optionally substituted by one substituent independently selected from halogen, $C_3$-$C_6$cycloalkyl and $C_1$-$C_2$alkoxy. In a further very preferred embodiment, said compound is a compound of formula Ia, and said R1 is hydrogen.

In a further very preferred embodiment, said compound is selected from
6-(3-fluoropyridin-4-yl)-N,5-di(pyridin-3-yl)-1,2,4-triazin-3-amine;
N-(3-fluorophenyl)-6-(3-fluoropyridin-4-yl)-5-(pyridin-3-yl)-1,2,4-triazin-3-amine;
N-(6-(3-fluoropyridin-4-yl)-5-(pyridin-3-yl)-1,2,4-triazin-3-yl)thiazol-2-amine;
4-chloro-N-(6-(3-fluoropyridin-4-yl)-5-(pyridin-3-yl)-1,2,4-triazin-3-yl)thiazol-2-amine;
N-(6-(3-fluoropyridin-4-yl)-5-(pyridin-3-yl)-1,2,4-triazin-3-yl)-3-methyl-1,2,4-thiadiazol-5-amine;
N-(6-(3-fluoropyridin-4-yl)-5-(pyridin-3-yl)-1,2,4-triazin-3-yl)-5-methyl-1,3,4-thiadiazol-2-amine:
1-(6-(3-fluoropyridin-4-yl)-5-(pyridin-3-yl)-1,2,4-triazin-3-yl)-3-methylurea;
5-(2-fluorophenyl)-N-(pyridin-3-yl)-6-(2-(trifluoromethyl)pyridin-4-yl)-1,2,4-triazin-3-amine;
5-(2-fluorophenyl)-N-(pyridin-3-yl)-6-(2-(trifluoromethyl)pyridin-4-yl)-1,2,4-triazin-3-amine;
4-chloro-N-(5-(2-fluorophenyl)-6-(2-(trifluoromethyl)pyridin-4-yl)-1,2,4-triazin-3-yl)thiazol-2-amine;
N-(5-(2-fluorophenyl)-6-(2-(trifluoromethyl)pyridin-4-yl)-1,2,4-triazin-3-yl)-3-methyl-1,2,4-thiadiazol-5-amine;
5-(2-fluorophenyl)-N-(3-fluorophenyl)-6-(3-fluoropyridin-4-yl)-1,2,4-triazin-3-amine;
N-(5-(2-fluorophenyl)-6-(3-fluoropyridin-4-yl)-1,2,4-triazin-3-yl)-3-methyl-1,2,4-thiadiazol-5-amine;
5-(2-fluorophenyl)-6-(3-fluoropyridin-4-yl)-N-(3-methyl-1H-pyrazol-5-yl)-1,2,4-triazin-3-amine;
5-(2-fluorophenyl)-6-(3-fluoropyridin-4-yl)-N-(3-methyl-1H-1,2,4-triazol-5-yl)-1,2,4-triazin-3-amine;
1-(5-(2-fluorophenyl)-6-(3-fluoropyridin-4-yl)-1,2,4-triazin-3-yl)-3-methylurea;
N-(3-fluorophenyl)-6-(3-fluoropyridin-4-yl)-5-(5-methyloxazol-2-yl)-1,2,4-triazin-3-amine;
N-(3-ethyl-1H-1,2,4-triazol-5-yl)-5-(2-fluorophenyl)-6-(3-fluoro-4-pyridyl)-1,2,4-triazin-3-amine;
[5-[[5-(2-fluorophenyl)-6-(3-fluoro-4-pyridyl)-1,2,4-triazin-3-yl]amino]-1H-1,2,4-triazol-3-yl]methanol;
N-[3-[(dimethylamino)methyl]-1H-1,2,4-triazol-5-yl]-5-(2-fluorophenyl)-6-(3-fluoro-4-pyridyl)-1,2,4-triazin-3-amine;
5-(2-fluorophenyl)-6-(3-fluoro-4-pyridyl)-N-(6-methyl-3-pyridyl)-1,2,4-triazin-3-amine;
[5-[[5-(2-fluorophenyl)-6-(3-fluoro-4-pyridyl)-1,2,4-triazin-3-yl]amino]-2-pyridyl]methanol;
5-(2-fluorophenyl)-6-(3-fluoro-4-pyridyl)-N-(6-methoxy-3-pyridyl)-1,2,4-triazin-3-amine;
5-(2-fluorophenyl)-6-(3-fluoro-4-pyridyl)-N-[6-(trifluoromethyl)-3-pyridyl]-1,2,4-triazin-3-amine;
1-(3-chlorophenyl)-3-[6-(3-fluoro-4-pyridyl)-5-(3-pyridyl)-1,2,4-triazin-3-yl]urea;
1-[6-(3-fluoro-4-pyridyl)-5-(3-pyridyl)-1,2,4-triazin-3-yl]-3-(4-methoxyphenyl)urea;
1-[6-(3-fluoro-4-pyridyl)-5-(3-pyridyl)-1,2,4-triazin-3-yl]-3-(2-morpholinoethyl)urea;
1-(3-chlorophenyl)-3-[5-(2-fluorophenyl)-6-(3-fluoro-4-pyridyl)-1,2,4-triazin-3-yl]urea;
1-[5-(2-fluorophenyl)-6-(3-fluoro-4-pyridyl)-1,2,4-triazin-3-yl]-3-(4-methoxyphenyl)urea;
1-[5-(2-fluorophenyl)-6-(3-fluoro-4-pyridyl)-1,2,4-triazin-3-yl]-3-(2-morpholinoethyl)urea;
N-(3-cyclopropyl-1H-1,2,4-triazol-5-yl)-5-(2-fluorophenyl)-6-(3-fluoro-4-pyridyl)-1,2,4-triazin-3-amine;
5-(2-fluorophenyl)-6-(3-fluoro-4-pyridyl)-N-[3-(trifluoromethyl)-1H-pyrazol-5-yl]-1,2,4-triazin-3-amine;
N-(3-ethyl-1H-pyrazol-5-yl)-5-(2-fluorophenyl)-6-(3-fluoro-4-pyridyl)-1,2,4-triazin-3-amine;
N-(3-cyclopropyl-1H-pyrazol-5-yl)-5-(2-fluorophenyl)-6-(3-fluoro-4-pyridyl)-1,2,4-triazin-3-amine;
1-cyclopropyl-3-[5-(2-fluorophenyl)-6-(3-fluoro-4-pyridyl)-1,2,4-triazin-3-yl]urea;
N-[6-(2,2-difluoroethoxy)pyridin-3-yl]-5-(2-fluorophenyl)-6-(3-fluoropyridin-4-yl)-1,2,4-triazin-3-amine;
2-fluoro-4-{[5-(2-fluorophenyl)-6-(3-fluoropyridin-4-yl)-1,2,4-triazin-3-yl]amino}phenyl)methanol;
2-(5-{[5-(2-fluorophenyl)-6-(3-fluoropyridin-4-yl)-1,2,4-triazin-3-yl]amino}pyridin-2-yl)propan-2-ol;
(5-{[5-(2-fluorophenyl)-6-(3-fluoropyridin-4-yl)-1,2,4-triazin-3-yl]amino}pyrimidin-2-yl)methanol;
1-(5-{[5-(2-fluorophenyl)-6-(3-fluoropyridin-4-yl)-1,2,4-triazin-3-yl]amino}pyridin-2-yl)ethan-1-ol;
3-(5-{[5-(2-fluorophenyl)-6-(3-fluoropyridin-4-yl)-1,2,4-triazin-3-yl]amino}pyridin-2-yl)oxetan-3-ol;
5-(2-fluorophenyl)-6-(3-fluoropyridin-4-yl)-N-[6-(propan-2-yl)pyridin-3-yl]-1,2,4-triazin-3-amine;
1-(5-{[5-(2-fluorophenyl)-6-(3-fluoropyridin-4-yl)-1,2,4-triazin-3-yl]amino}pyridin-2-yl)-2-methylpropan-1-ol;
N-(6-cyclopropylpyridin-3-yl)-5-(2-fluorophenyl)-6-(3-fluoropyridin-4-yl)-1,2,4-triazin-3-amine;

5-(2-fluorophenyl)-6-(3-fluoropyridin-4-yl)-N-[3-(propan-2-yl)-1H-1,2,4-triazol-5-yl]-1,2,4-triazin-3-amine;
N-(3-tert-butyl-1H-1,2,4-triazol-5-yl)-5-(2-fluorophenyl)-6-(3-fluoropyridin-4-yl)-1,2,4-triazin-3-amine;
5-(2-fluorophenyl)-6-(3-fluoropyridin-4-yl)-N-[3-(1-methylcyclopropyl)-1H-1,2,4-triazol-5-yl]-1,2,4-triazin-3-amine; and
2-(5-{[5-(2-fluorophenyl)-6-(3-fluoropyridin-4-yl)-1,2,4-triazin-3-yl]amino}-1H-1,2,4-triazol-3-yl)propan-2-ol.

In a further very preferred embodiment, said compound is selected from
6-(3-fluoropyridin-4-yl)-N,5-di(pyridin-3-yl)-1,2,4-triazin-3-amine;
N-(3-fluorophenyl)-6-(3-fluoropyridin-4-yl)-5-(pyridin-3-yl)-1,2,4-triazin-3-amine;
N-(6-(3-fluoropyridin-4-yl)-5-(pyridin-3-yl)-1,2,4-triazin-3-yl)thiazol-2-amine;
4-chloro-N-(6-(3-fluoropyridin-4-yl)-5-(pyridin-3-yl)-1,2,4-triazin-3-yl)thiazol-2-amine;
N-(6-(3-fluoropyridin-4-yl)-5-(pyridin-3-yl)-1,2,4-triazin-3-yl)-3-methyl-1,2,4-thiadiazol-5-amine;
N-(6-(3-fluoropyridin-4-yl)-5-(pyridin-3-yl)-1,2,4-triazin-3-yl)-5-methyl-1,3,4-thiadiazol-2-amine:
1-(6-(3-fluoropyridin-4-yl)-5-(pyridin-3-yl)-1,2,4-triazin-3-yl)-3-methylurea;
5-(2-fluorophenyl)-N-(pyridin-3-yl)-6-(2-(trifluoromethyl)pyridin-4-yl)-1,2,4-triazin-3-amine;
5-(2-fluorophenyl)-N-(pyridin-3-yl)-6-(2-(trifluoromethyl)pyridin-4-yl)-1,2,4-triazin-3-amine;
4-chloro-N-(5-(2-fluorophenyl)-6-(2-(trifluoromethyl)pyridin-4-yl)-1,2,4-triazin-3-yl)thiazol-2-amine;
N-(5-(2-fluorophenyl)-6-(2-(trifluoromethyl)pyridin-4-yl)-1,2,4-triazin-3-yl)-3-methyl-1,2,4-thiadiazol-5-amine;
5-(2-fluorophenyl)-N-(3-fluorophenyl)-6-(3-fluoropyridin-4-yl)-1,2,4-triazin-3-amine;
N-(5-(2-fluorophenyl)-6-(3-fluoropyridin-4-yl)-1,2,4-triazin-3-yl)-3-methyl-1,2,4-thiadiazol-5-amine;
5-(2-fluorophenyl)-6-(3-fluoropyridin-4-yl)-N-(3-methyl-1H-pyrazol-5-yl)-1,2,4-triazin-3-amine;
5-(2-fluorophenyl)-6-(3-fluoropyridin-4-yl)-N-(3-methyl-1H-1,2,4-triazol-5-yl)-1,2,4-triazin-3-amine;
1-(5-(2-fluorophenyl)-6-(3-fluoropyridin-4-yl)-1,2,4-triazin-3-yl)-3-methylurea;
(2-fluoro-4-{[5-(2-fluorophenyl)-6-(3-fluoropyridin-4-yl)-1,2,4-triazin-3-yl]amino}phenyl)methanol;
2-(5-{[5-(2-fluorophenyl)-6-(3-fluoropyridin-4-yl)-1,2,4-triazin-3-yl]amino}pyridin-2-yl)propan-2-ol;
(5-{[5-(2-fluorophenyl)-6-(3-fluoropyridin-4-yl)-1,2,4-triazin-3-yl]amino}pyrimidin-2-yl)methanol;
N-(6-cyclopropylpyridin-3-yl)-5-(2-fluorophenyl)-6-(3-fluoropyridin-4-yl)-1,2,4-triazin-3-amine; and
N-(3-tert-butyl-1H-1,2,4-triazol-5-yl)-5-(2-fluorophenyl)-6-(3-fluoropyridin-4-yl)-1,2,4-triazin-3-amine.

Many of the inventive compounds of formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, phydroxybenzoic acid, 1-hydroxynaphthalene-2-carboxylic acid or 3-hydroxynaphthalene-2carboxylic acid, and sulfonic acids such as methanesulfonic acid or benzenesulfonic acid. These salts may be prepared from compounds of formula I by known salt-forming procedures.

Compounds of formula I which contain acidic, e. g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

A "hydrate" refers to an association or complex of one or more water molecules and a compound of the invention. The hydrates can be stoichiometric or non-stoichiometric. Particularly preferred examples of hydrates include hemihydrates, monohydrates and dihydrates.

In another aspect, the present invention provides the inventive compound of formula I for use as a medicament.

In another aspect, the present invention provides a pharmaceutical composition comprising the inventive compound of formula I, optionally together with a pharmaceutically acceptable diluent or carrier.

In a further aspect, the present invention provides the inventive compound of formula I or the inventive pharmaceutical composition for use in a method of treating a condition, disorder or disease mediated by activation of the adenosine A2B receptor.

In a further aspect, the present invention provides the inventive compound of formula I or the inventive pharmaceutical composition for use in a method of treating a condition, disorder or disease ameliorated by the inhibition of the adenosine A2B receptor.

In a further aspect, the present invention provides the inventive compound of formula I or the inventive pharmaceutical composition for use in a method of treating a condition or disease susceptible to amelioration by antagonism of the adenosine A2B receptor.

In another aspect, the present invention provides the use of a compound of formula I according to the present invention in the manufacture of a medicament for the treatment of a condition, disorder or disease mediated by activation of the adenosine A2B receptor.

Due to their ability of inhibition of adenosine A2B receptor activation, compounds of formula I and pharmaceutically acceptable salts, or hydrates thereof in accordance with the present invention are useful in the treatment or prevention of conditions, disorders and diseases which are mediated by the activation of the adenosine A2B receptor. Said conditions, disorders and diseases are particularly selected from a respiratory disease, an inflammatory obstructive airways disease, an inflammatory disease, a metabolic disease, a renal disease, a vascular disease, an allergic disease, an inflammatory gastrointestinal tract disorder, an autoimmune disease, a neurological disorder and, in particular, a cancer. Accordingly, the compounds and pharmaceutical compositions of the present invention are useful in the treatment of cancer, and hereby in particular ovarian, lung, liver, oral, colon, skin and prostate cancer including melanoma and squamous cell carcinoma.

Thus, in another aspect, the present invention provides a method of treating a condition, disorder or disease mediated by activation of the adenosine A2B receptor comprising administering a therapeutically effective amount of a compound of formula I according to the present invention.

In another aspect, the present invention provides the inventive compound of formula I or the inventive pharmaceutical composition for use in a method of treating a condition, disorder or disease selected from a respiratory disease, an inflammatory obstructive airways disease, an inflammatory disease, a metabolic disease, a renal disease, a vascular disease, an allergic disease, an inflammatory gastrointestinal tract disorder, an autoimmune disease, a neurological disorder and a cancer.

In another aspect, the present invention provides the use of a compound of formula I according to the present invention in the manufacture of a medicament for the treatment of a condition, disorder or disease selected from a respiratory disease, an inflammatory obstructive airways disease, an inflammatory disease, a metabolic disease, a renal disease, a vascular disease, an allergic disease, an inflammatory gastrointestinal tract disorder, an autoimmune disease, a neurological disorder and a cancer.

In another aspect, the present invention provides a method of treating a condition, disorder or disease selected from a respiratory disease, an inflammatory obstructive airways disease, an inflammatory disease, a metabolic disease, a renal disease, a vascular disease, an allergic disease, an inflammatory gastrointestinal tract disorder, an autoimmune disease, a neurological disorder and a cancer, wherein said method comprises administering to a subject, particularly a human subject, in need thereof, a therapeutically effective amount of an inventive compound of formula I or a pharmaceutically acceptable salt, or hydrate thereof.

In a very preferred embodiment, said respiratory disease, inflammatory obstructive airways disease, inflammatory disease, metabolic disease, renal disease, vascular disease, allergic disease, inflammatory gastrointestinal tract disorder, autoimmune disease, neurological disorder or said cancer is selected from pulmonary fibrosis, pulmonary hypertension (PH), chronic obstructive pulmonary disease (COPD), asthma, acute lung injury (ALI), adult respiratory distress syndrome (ARDS), bronchitis, pneumoconiosis, psoriasis, contact dermatitis, atopic dermatitis, conjunctivitis, allergic rhinitis, bowel disease, multiple sclerosis, diabetes, juvenile diabetes, diabetes mellitus, diabetic nephropathy, renal fibrosis, chronic kidney disease (CKD), renal ischemia, hypertension, retinopathy, Parkinson disease, Alzheimer disease, Huntington disease, attention deficit disorder (ADD), attention deficit hyperactivity disorder (ADHD), ovarian cancer, lung cancer, liver cancer, renal cancer, rectal cancer, oral cancer, breast cancer, bladder cancer, colon cancer, skin cancer and prostate cancer including melanoma and squamous cell carcinoma.

Thus, the compounds and pharmaceutical compositions of the present invention are useful in the treatment of inflammatory or obstructive airways diseases, resulting, for example, in reduction of bronchial hyperreactivity, remodelling or disease progression. Inflammatory or obstructive airways diseases for which the present inventive compounds and pharmaceutical compositions are applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Prophylactic efficacy in the treatment of asthma will be evidenced by reduced frequency or severity of symptomatic attack, improvement in lung function or by reduced requirement for other, symptomatic therapy, such anti-inflammatory (e.g. corticosteroid) or bronchodilatory therapy. Further inflammatory or obstructive airways diseases and conditions for which the present inventive compounds and pharmaceutical compositions are useful include acute lung injury (ALI), adult respiratory distress syndrome (ARDS), chronic obstructive pulmonary, airways or lung disease (COPD, COAD or COLD) as well as bronchitis and pneumoconiosis.

Moreover, the compounds and pharmaceutical compositions of the present invention are useful in the treatment of inflammatory or allergic conditions of the skin, for example psoriasis, contact dermatitis and atopic dermatitis, as well as in the treatment of inflammatory diseases or conditions of the eye such as conjunctivitis, or diseases affecting the nose including allergic rhinitis.

Furthermore, the compounds and pharmaceutical compositions of the present invention are useful in the treatment of an inflammatory disease in which autoimmune reactions are implicated or having an autoimmune component, including autoimmune inflammatory bowel disease, multiple sclerosis, diabetes and juvenile diabetes (diabetes mellitus type I).

The inventive compounds and pharmaceutical compositions may be administered by any suitable route, depending on the nature of the disorder to be treated, e.g. orally (as syrups, tablets, capsules, lozenges, controlled-release preparations, fast-dissolving preparations, lozenges, etc); topically (as creams, ointments, lotions, nasal sprays or aerosols, etc); by injection (subcutaneous, intradermal, intramuscular, intravenous, etc.) or by inhalation (as a dry powder, a solution, a dispersion, etc).

In further aspects, the present invention provides processes for the manufacture of compounds of formula I as described herein.

Thus, in another aspect, the present invention provides a method of manufacturing a compound of formula I or pharmaceutically acceptable salt, or hydrate thereof,

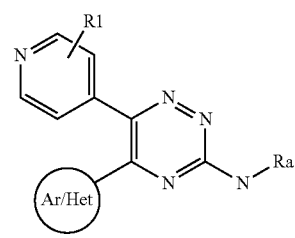

I wherein
R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;
Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy;

Ar/Het is selected from pyridinyl, phenyl and oxazolyl wherein said pyridinyl, phenyl and oxazolyl is independently optionally substituted by one or more, preferably one, substituents selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;

wherein said method comprises reacting a compound of formula II

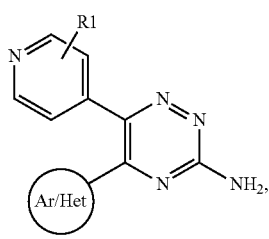

II wherein R1 and Ar/Het are as defined above;
with a compound of formula III

Ra—Br    III wherein Ra is as defined above.

Thus, in a further aspect, the present invention provides a method of manufacturing a compound of formula I or pharmaceutically acceptable salt, or hydrate thereof,

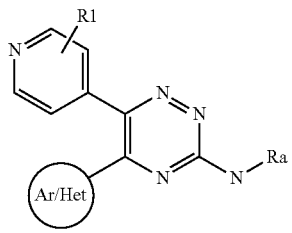

I wherein
R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;

is selected from phenyl or a heteroaryl, wherein said phenyl or said heteroaryl is optionally independently substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl and a heterocycle selected from oxiran, oxetane, aziridine and azetidine, wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents selected from halogen, cycloalkyl, $C_1$-$C_8$alkyl, $C_1$-$C_8$alkoxy, $C_1$-$C_8$hydroxyalkyl and $C_1$-$C_8$alkoxyalkyl; wherein further preferably said heteroaryl is a 5- or 6-membered heteroaryl, wherein again further preferably said 5- or 6-membered heteroaryl is selected from pyridinyl, pyrimidinyl, thiazolyl, thiodiazolyl, oxazolyl, pyrazolyl and triazolyl;

Ar/Het is selected from pyridinyl, phenyl and oxazolyl wherein said pyridinyl, phenyl and oxazolyl is independently optionally substituted by one or more, preferably one, substituents selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;

wherein said method comprises reacting a compound of formula II

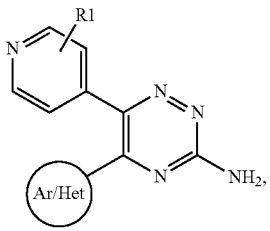

II wherein R1 and Ar/Het are as defined above;
with a compound of formula III

Ra—Br    III wherein Ra is as defined above.

The embodiments, preferred embodiments and very preferred embodiments for said R1, Ar/Het including R2, and Ra as defined herein shall apply to these and all described inventive methods of manufacturing of said compounds of formula I.

Thus, in a preferred embodiment of said method, said Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy.

Said inventive method can be carried out via a Buchwald cross coupling reaction, wherein said Buchwald cross coupling reaction is typically conducted with the palladium precatalysts XPhosPdG2 or tBuXPhosPdG1 and sodium tert-butoxide as a base in anhydrous 1,4-dioxane at elevated temperature, i.e. at 120° C., optionally in a microwave reactor.

Thus, in a further preferred embodiment of said method, said reacting of said compound of formula II with said compound of formula III is in the presence of a palladium catalyst or pre-catalyst and in the presence of a base. The skilled person in the art knows the palladium catalyst or pre-catalyst catalyst and bases usable for the inventive method. Preferably, said palladium catalyst or pre-catalyst is XPhosPdG2 or tBuXPhosPdG1. In another preferred embodiment, said base is sodium tert-butoxide. In another preferred embodiment, said reacting of said compound of formula II with said compound of formula III is conducted in a solvent at a temperature of 80-140° C.; wherein preferably said solvent is dioxane and preferably said temperature is 110-130° C.

In another aspect, the present invention provides a method of manufacturing a compound of formula I or pharmaceutically acceptable salt, or hydrate thereof,

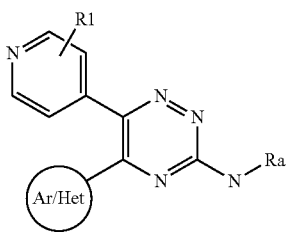

I wherein
R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;
Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl, and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy;
Ar/Het is selected from pyridinyl, phenyl and oxazolyl wherein said pyridinyl, phenyl and oxazolyl is independently optionally substituted by [one or more] substituents selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;
wherein said method comprises reacting a compound of formula V

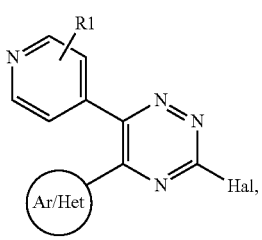

V wherein R1 and Ar/Het are as defined above;
with a compound of formula VI

Ra—NH2    VI wherein Ra is as defined above.

The embodiments, preferred embodiments and very preferred embodiments for said R1, Ar/Het including R2, and Ra as defined herein shall apply to this inventive method of manufacturing of said compounds of formula I.

In a further aspect, the present invention provides a method of manufacturing a compound of formula I or pharmaceutically acceptable salt, or hydrate thereof,

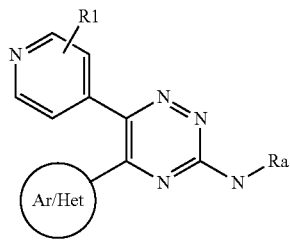

I wherein
R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;
Ra is selected from phenyl or a heteroaryl, wherein said phenyl or said heteroaryl is optionally independently substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl and a heterocycle selected from oxiran, oxetane, aziridine and azetidine, wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy; or Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents selected from halogen, cycloalkyl, $C_1$-$C_8$alkyl, $C_1$-$C_8$alkoxy, $C_1$-$C_8$hydroxalkyl and $C_1$-$C_8$alkoxyalkyl; wherein further preferably said heteroaryl is a 5- or 6-membered heteroaryl, wherein again further preferably said 5- or 6-membered heteroaryl is selected from pyridinyl, pyrimidinyl, thiazolyl, thiodiazolyl, oxazolyl, pyrazolyl and triazolyl;
Ar/Het is selected from pyridinyl, phenyl and oxazolyl wherein said pyridinyl, phenyl and oxazolyl is independently optionally substituted by [one or more] substituents selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;
wherein said method comprises reacting a compound of formula V

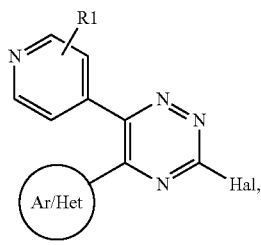

V wherein R1 and Ar/Het are as defined above;
with a compound of formula VI

Ra—NH2    VI wherein Ra is as defined above.

The embodiments, preferred embodiments and very preferred embodiments for said R1, Ar/Het including R2, and Ra as defined herein shall apply to this inventive method of manufacturing of said compounds of formula I.

Thus, in a preferred embodiment of said method, said Ra is selected from phenyl, pyridinyl, pyrimidinyl, thiazolyl, thiodiazolyl, oxazolyl, pyrazolyl and triazolyl wherein said phenyl, pyridinyl, thiazolyl, thiodiazolyl, oxazolyl, pyrazolyl and triazolyl is independently optionally substituted by one or more, preferably one, substituents independently selected from halogen, hydroxyl, cycloalkyl, $C_1$-$C_4$alkyl-substituted cycloalkyl, $C_1$-$C_8$alkyl, $C_1$-$C_8$haloalkyl, $C_1$-$C_8$alkoxy, $C_1$-$C_8$alkylaminocarbonyl, $C_1$-$C_8$hydroxyalkyl, $C_1$-$C_8$haloalkoxy, $C_1$-$C_8$dialkylamino$C_1$-$C_8$alkyl, $C_1$-$C_8$aminoalkyl, and a heterocycle selected from oxiran, oxetane, aziridine and azetidine wherein said oxiran, oxetane, aziridine and azetidine are independently optionally substituted by halogen, hydroxyl, $C_1$-$C_2$alkyl, $C_1$-$C_2$haloalkyl, $C_1$-$C_2$alkoxy.

Said inventive method can be carried out by reacting said compounds V and VI in a solvent such as isopropanol (IPA) and in the presence of a base such as N,N-diisopropylethylamine (DIPEA), at elevated temperature. Alternatively, said inventive method can be carried out by palladium catalyzed Buchwald type C—N cross-coupling reaction known to the person skilled in the art.

Thus, in a further preferred embodiment of said method, said reacting of said compound of formula V with said compound of formula VI is in the presence of a metal catalyst or in the presence of a base, preferably in the presence of a base. In a further preferred embodiment of said method, said halogen in said compounds of formula V is iodine. In a further preferred embodiment of said method, said base is DIPEA. In another preferred embodiment, said reacting of said compound of formula V with said compound of formula VI is conducted in a solvent at a temperature of 60-140° C.; wherein preferably said temperature is 70-90° C. In a further preferred embodiment, said solvent is IPA.

In another aspect, the present invention provides a method of manufacturing a compound of formula I or pharmaceutically acceptable salt, or hydrate thereof,

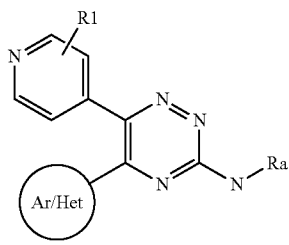

I wherein
R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;
Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents independently selected from halogen, cycloalkyl, $C_1$-$C_8$alkyl, $C_1$-$C_8$alkoxy, $C_1$-$C_8$hydroxalkyl and $C_1$-$C_8$alkoxyalkyl;
Ar/Het is selected from pyridinyl, phenyl and oxazolyl wherein said pyridinyl, phenyl and oxazolyl is independently optionally substituted by one or more] substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;
wherein said method comprises reacting a compound of formula V

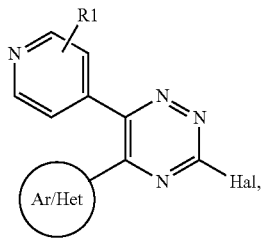

V wherein R1 and Ar/Het are as defined above;
with a compound of formula VII

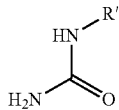

VII wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents independently selected from halogen, cycloalkyl, $C_1$-$C_8$alkyl, $C_1$-$C_8$alkoxy, $C_1$-$C_8$hydroxyalkyl and $C_1$-$C_8$alkoxyalkyl.

The embodiments, preferred embodiments and very preferred embodiments for said R1, Ar/Het including R2, R' and Ra as defined herein shall apply to this inventive method of manufacturing of said compounds of formula I.

Thus, in a preferred embodiment of said method, said R' is selected from $C_1$-$C_4$alkyl, $C_3$-$C_6$cycloalkyl, aryl, heteroaryl and $C_1$-$C_4$alkyl-N-morpholino.

Said inventive method can be carried out by palladium catalyzed Buchwald type C—N cross-coupling with a catalyst such as Ruphos precatalyst, sodium tert-butoxide as a base in a solvent such as 1,4-dioxane at elevated temperatures.

Alternatively, said inventive method can be carried out by reaction of compounds V and VII in a solvent such as IPA, DMF, DMSO or methylene chloride and in the presence of a base such as DIPEA or trietylamine at room temperature or elevated temperature, as known by the person skilled in the art.

Thus, in a further preferred embodiment of said method, said reacting of said compound of formula V with said compound of formula VII is in the presence of a metal catalyst or precatalyst, or in the presence of a base, preferably in the presence of a base. In a further preferred embodiment of said method, said halogen in said compounds of formula V is iodine. In a further preferred embodiment of said method, wherein said reacting of said compound of formula V with said compound of formula VII is in the presence of a base, said base is DIPEA or trietylamine, preferably DIPEA. In another preferred embodiment, said reacting of said compound of formula V with said compound of formula VI is conducted in a solvent at a temperature of room temperature, i.e. at 20-28° C. or at elevated temperatures, i.e. at 60-140° C.; wherein preferably said temperature is 70-120° C. In a further preferred embodiment, said solvent is selected from IPA, DMF, DMSO or methylene chloride, preferably said solvent is IPA.

In another aspect, the present invention provides a method of manufacturing a compound of formula I or pharmaceutically acceptable salt, or hydrate thereof,

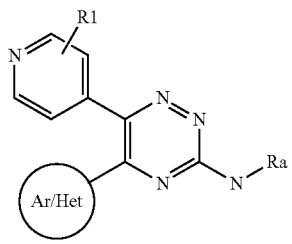

I wherein
R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;
Ra is —CONHR' wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents independently selected from halogen, cycloalkyl, $C_1$-$C_8$alkyl, $C_1$-$C_8$alkoxy, $C_1$-$C_8$hydroxyalkyl and $C_1$-$C_8$alkoxyalkyl;

Ar/Het is selected from pyridinyl, phenyl and oxazolyl wherein said pyridinyl, phenyl and oxazolyl is independently optionally substituted by one or more, preferably one substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;
wherein said method comprises reacting a compound of formula II

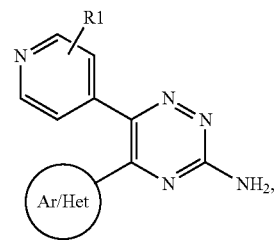

II wherein R1 and Ar/Het are as defined above;
with a compound of formula IV

R'—NH2    IV, in the presence of a reagent able to form an urea-functionality with said compounds of formula II and IV;
wherein R' is selected from $C_1$-$C_8$alkyl, cycloalkyl, aryl, heteroaryl and $C_1$-$C_8$alkyl-N-morpholino, wherein said aryl, heteroaryl and $C_1$-$C_8$alkyl-N-morpholino is independently optionally substituted by one or more, preferably one, substituents independently selected from halogen, cycloalkyl, $C_1$-$C_8$alkyl, $C_1$-$C_8$alkoxy, $C_1$-$C_8$hydroxyalkyl and $C_1$-$C_8$alkoxyalkyl; and wherein said reagent able to form an urea-functionality with said compounds of formula II and IV is preferably selected from 1,1'-carbonyldiimidazole (CDI), phosgene, diphosgene and triphosgene, wherein further preferably said reagent able to form an urea-functionality with said compounds of formula II and IV is 1,1'-carbonyldiimidazole (CDI).

The embodiments, preferred embodiments and very preferred embodiments for said R1, Ar/Het including R2, R' and Ra as defined herein shall apply to this inventive method of manufacturing of said compounds of formula I.

Thus, in a preferred embodiment of said method, said R' is selected from $C_1$-$C_4$alkyl, $C_3$-$C_6$cycloalkyl, aryl, heteroaryl and $C_1$-$C_4$alkyl-N-morpholino.

Said inventive method can be carried out by with 1,1'-carbonyldiimidazole (CDI) in the presence of a base such as DIPEA in THF as a solvent. Instead of CDI other reagents suited for the formation of urea functional groups can be employed such as phosgene, diphosgene, triphosgene and the likes.

Thus, in a further preferred embodiment of said method, said reacting of said compound of formula II with said compound of formula IV is in the presence of a reagent able to form an urea-functionality with said compounds of formula II and IV and in the presence of a base. In a further preferred embodiment of said method, said base is DIPEA. In another preferred embodiment, said reacting of said compound of formula II with said compound of formula IV in the presence of a reagent able to form an urea-functionality with said compounds of formula II and IV is conducted in a solvent wherein preferably said solvent is THF.

In another aspect, the present invention provides for a compound of formula II

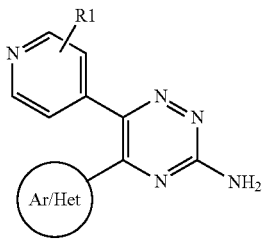

II wherein

R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;

Ar/Het is selected from pyridinyl, phenyl and oxazolyl wherein said pyridinyl, phenyl and oxazolyl is independently optionally substituted by one or more, preferably one, substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl.

The embodiments, preferred embodiments and very preferred embodiments for said R1, Ar/Het including R2, as defined herein shall apply to this inventive compound of formula II.

Very preferred embodiments of said compound of formula II are selected from

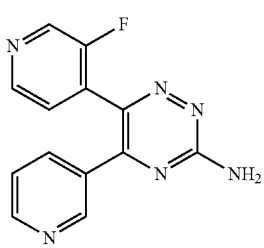

II-1

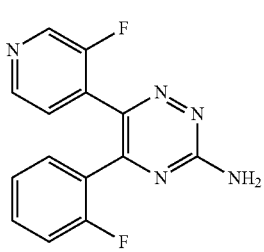

II-2

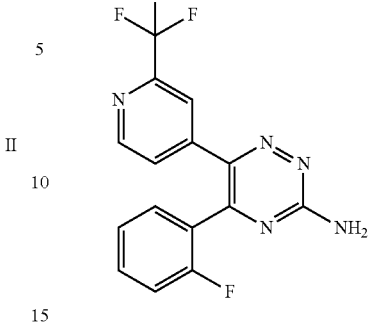

II-3

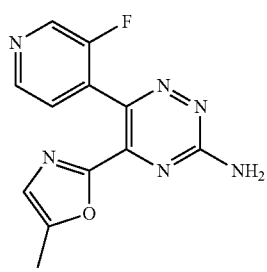

II-4

In another aspect, the present invention provides for a compound of formula V

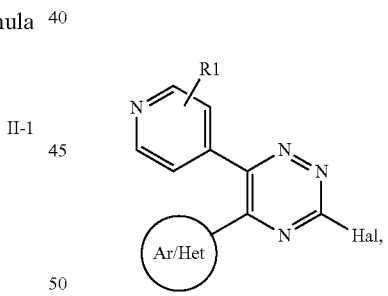

V wherein

R1 represents 1 to 3 identical or different R1 substituents, wherein said R1 is independently at each occurrence selected from hydrogen, halogen, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl, preferably R1 represents 1 or 2 R1, further preferably R1 represents 1 R1;

Ar/Het is selected from pyridinyl, phenyl and oxazolyl wherein said pyridinyl, phenyl and oxazolyl is independently optionally substituted by one or more, preferably one, substituents independently selected from halogen, cyano, $C_1$-$C_8$alkyl, $C_1$-$C_8$haloalkyl, $C_1$-$C_8$alkoxy, $C_1$-$C_8$hydroxyalkyl and $C_1$-$C_8$alkoxyalkyl;

A very preferred embodiment of said compound of formula II is V-1

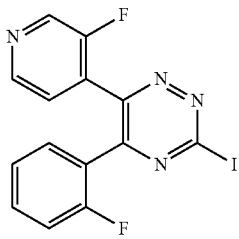

DETAILED DESCRIPTION OF PREPARATION PROCESSES OF COMPOUNDS OF FORMULA I

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein unless indicated to the contrary. In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

The compounds of formula I of the present invention can be prepared according to Scheme 1:

Scheme 1

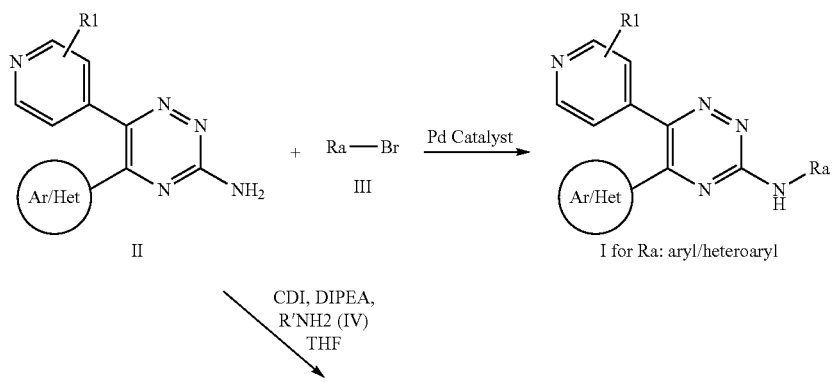

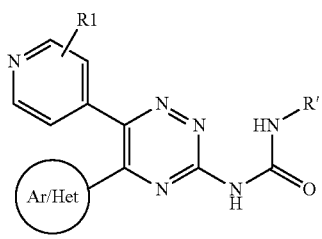

I for Ra: CONHR'

Thus, compounds of formula I with Ra=aryl or heteroaryl in accordance with the present invention can be prepared starting from compounds of general formula II which can be coupled with an appropriate heteroaryl- or aryl-bromide RaBr of formula III to give the desired compound of general formula I via a Buchwald cross coupling reaction. Said Buchwald cross coupling reaction is typically conducted with the palladium precatalysts XPhosPdG2 or tBuXPhos-PdG1 and sodium tert-butoxide as a base in anhydrous 1,4-dioxane at elevated temperature, i.e. at 120° C., optionally in a microwave reactor (Buchwald et al. Chem Sci. 2013, 4, 916).

Compounds of formula I with Ra=—CONHR' in accordance with the present invention can be prepared from II via treatment with 1,1'-carbonyldiimidazole (CDI) in the presence of a base such as DIPEA in THF as a solvent and subsequent reaction of the intermediate with an appropriate amine R'NH2 of formula IV. Instead of CDI other reagents suited for the formation of urea functional groups can be employed such as phosgene, diphosgene, triphosgene and the likes.

Alternatively, the compounds of formula I of the present invention can be synthesized as outlined in Scheme 2:

Scheme 2

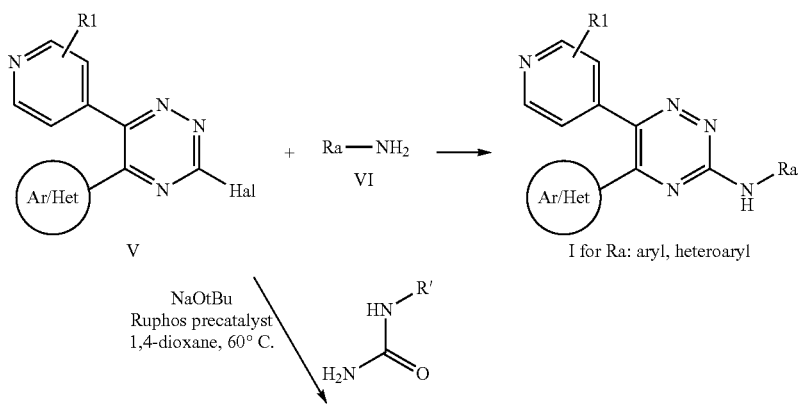

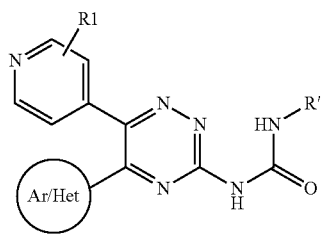

I for Ra: CONHR'

Hal = Br, I

Thus, compounds of formula I with Ra=aryl or heteroaryl in accordance with the present invention can be prepared by reaction of halo-triazines V, preferably with Hal=Iodine, and an appropriate aryl- or heteroaryl-amine of general formula VI in a solvent such as IPA and with a suited base such as DIPEA, at elevated temperature, i.e. at 80° C.

Alternatively the reaction can be accomplished by palladium catalyzed Buchwald type C—N cross-coupling reaction essentially as described in Scheme 1.

Compounds of formula I with Ra=—CONHR' in accordance with the present invention can be prepared by Buchwald coupling from V and corresponding substituted ureas of formula VII with a catalyst such as Ruphos precatalyst, sodium tert-butoxide as a base in a solvent such as 1,4-dioxane at elevated temperatures, i.e. at 60° C. (Buchwald et al. Chem Sci. 2013, 4, 916 and J. Am. Chem. Soc. 2010, 132, 15914).

Amino-triazine intermediates of formula II and halo-triazine intermediates of formula V which can be used as starting materials for the preparation of compounds of formula I can be prepared as described in the Scheme 3 and in Scheme 4.

nents in a solvent such as ethanol in the presence of two equivalents of acetic acid. The regioisomers obtained can be separated by preparative HPLC to give the desired compounds of formula II. In cases where the isomers are difficult to separate by preparative HPLC another option consists of employing the isomeric mixture in the subsequent reaction step and performing the isolation of the desired isomer at a later stage of the reaction sequence. In cases where aerobic DABCO catalyzed oxidation procedure is used oxidation and ring closure reaction can be performed in a one pot synthesis.

An alternative scheme for preparation of amino-triazine intermediates of general formula II is summarized in Scheme 4.

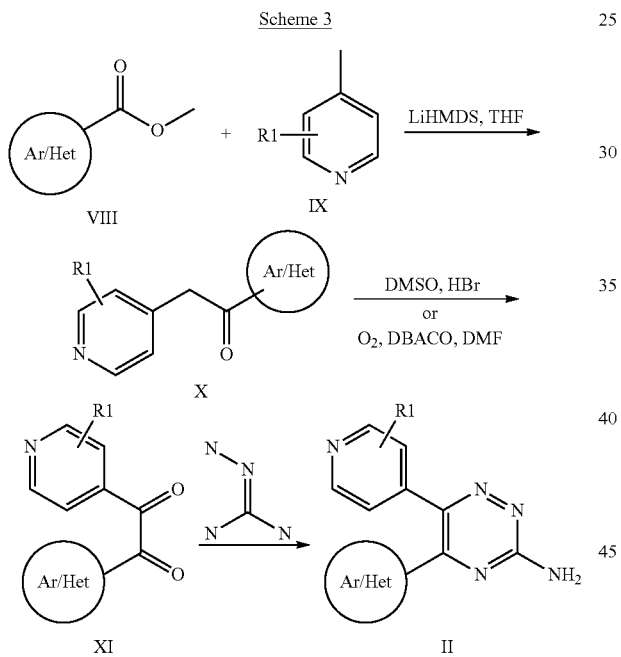

Scheme 3

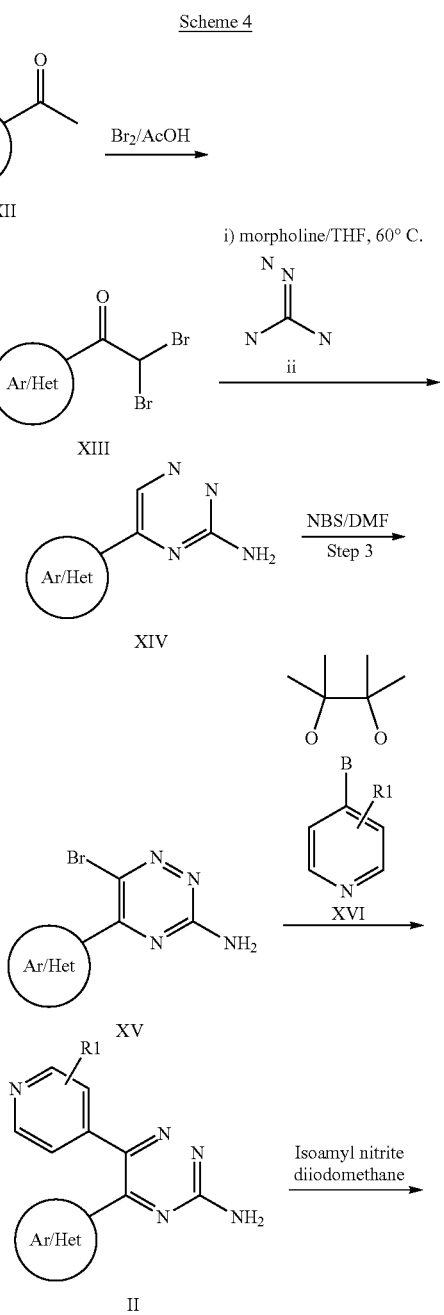

Scheme 4

Thus, according to Scheme 3, in a first step an appropriately substituted ethyl aryl-, heteroaryl-carboxylate VIII is reacted with substituted 4-methyl-pyridines IX in an acylation reaction with, for example, LiHMDS as a base and in a aprotic solvent such as THF to give ketone X. Subsequent oxidation to the corresponding diketones of formula XI can be accomplished with 48% aqueous hydrobromic acid in dimethyl sulfoxide (M. B. Floyd, J. Org. Chem. 1985, 50, 5022-5027). A further method comprises 1,4-diazabicyclo [2.2.2]octane (DABCO) catalyzed aerobic oxidation in anhydrous DMF at elevated temperature, i.e. at 90° C., as described (C. Qi, Synthesis, 2011, p 387-396). Alternatively, the oxidation can also be carried out with selenium dioxide as known in the art (N. Rabjohn, N. Org. React. (N. Y.) 1976, 24, 261).

Subsequent condensation of XI with aminoguanidine bicarbonate can be achieved upon heating of both compo- -continued

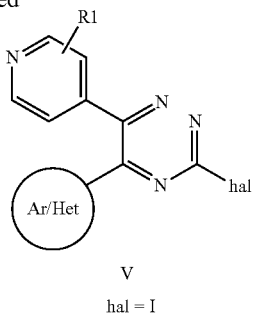

V
hal = I

Starting from an appropriate aryl-, heteroryl methyl ketones XII these are brominated with bromine in anhydrous acetic acid at 65° C. to give the desired dibromomethyl-ketones XII. Subsequent reaction with an excess of morpholine (i.e. 4.2 eq) in anhydrous THF at elevated temperatures, i.e. at 65° C., followed by treatment of crude intermediate at 70° C. with amino guanidine bicarbonate in methanol under addition of acetic acid gives then the aminotriazines of formula XIV. Selective bromination of XIV is achieved with NBS in DMF to provide compounds XV. The transformation of XV to compounds of general formula II can then be achieved via Suzuki coupling with appropriately substituted pyridine-4-boronic acid pinacol esters XVI in a microwave reactor under heating with cesium carbonate as a base, Pd(dppf)Cl$_2$ as catalyst in mixture of 1,4-dioxane/water (2:1) as solvent.

Halo-triazines of general formula V employed for the preparation of compounds of formula I can be prepared from II by Sandmeyer reaction, such, as in case of hal=Iodine, on treatment with isoamyl nitrite in diiodomethane at elevated temperatures, i.e. at 60° C.

The starting materials employed in the reaction are either commercially available, known in the literature or described in the experimental part. Depending on the different groups as defined for compounds of formula I one reaction scheme might be preferred over the other.

EXAMPLES

Example 1

Synthesis of Preferred Compounds of Formula I

Preferred compounds of formula I of the present invention were synthesized as described in the following and are either referred as Compound 1, 2, 3 or the like and, thus, by way of arabic numbers or by way referring to Example 1, 2, 3 or the like. The aforementioned definitions are interchangeably used herein.

Synthesis of Examples 1 to 6

Table 1 lists the preferred compounds and examples 1-6, respectively, of the present invention, its name, structure, characterizing data such as LCMS and NMR as well as the Intermediates from which they have been prepared.

TABLE 1

| Ex No | Compound | Prepared from | LCMS [M + H]$^+$ | NMR (CD$_3$OD) δ |
|---|---|---|---|---|
| 1 | 6-(3-fluoropyridin-4-yl)-N,5-di(pyridin-3-yl)-1,2,4-triazin-3-amine | 3-bromopyridine and 6-(3-fluoropyridin-4-yl)-5-(pyridin-3-yl)-1,2,4-triazin-3-amine (Intermediate II-1) | 346.2 | 9.31 (bs, 1H), 8.77-8.57 (m, 4H), 8.42 (s, 1H), 7.99 (m, 1H), 7.89 (m, 1H), 7.73 (s, 1H), 7.47 (m, 1H). |
| 2 | N-(3-fluorophenyl)-6-(3-fluoropyridin-4-yl)-5-(pyridin-3-yl)-1,2,4-triazin-3-amine | 1-bromo-3-fluorobenzene and 6-(3-fluoropyridin-4-yl)-5-(pyridin-3-yl)-1,2,4-triazin-3-amine (Intermediate II-1) | 363.2 | 8.91-8.28 (bs, 3H), 8.04 (m, 1H), 7.91 (bs, 1H), 7.73 (m, 2H), 7.57-7.49 (m, 2H), 7.35 (m, 1H), 6.82 (m, 1H). |
| 3 | N-(6-(3-fluoropyridin-4-yl)-5-(pyridin-3-yl)-1,2,4-triazin-3-yl)thiazol-2-amine | 2-bromothiazole and 6-(3-fluoropyridin-4-yl)-5-(pyridin-3-yl)-1,2,4- | 352.1 | 8.83 (s, 1H), 8.77 (bs, 1H), 8.60 (m, 1H), 8.41 (s, 1H), |

TABLE 1-continued

| Ex No | Compound | Prepared from | LCMS [M + H]+ | NMR (CD3OD) δ |
|---|---|---|---|---|
| | (structure) | triazin-3-amine (Intermediate II-1) | | 8.06 (m, 1H), 7.89 (m, 1H), 7.12 (m, 1H). |
| 4 | 4-chloro-N-(6-(3-fluoropyridin-4-yl)-5-(pyridin-3-yl)-1,2,4-triazin-3-yl)thiazol-2-amine (structure) | 2-bromo-4-chloro-thiazole and 6-(3-fluoropyridin-4-yl)-5-(pyridin-3-yl)-1,2,4-triazin-3-amine (Intermediate II-1) | 386.1 | 8.95 (bs, 1H), 8.81 (bs, 1H), 8.66 (m, 1H), 8.45 (s, 1H), 8.25 (m, 1H), 7.97 (m, 1H), 7.71 (m, 1H), 7.58 (s, 1H), 6.89 (s, 1H). |
| 5 | N-(6-(3-fluoropyridin-4-yl)-5-(pyridin-3-yl)-1,2,4-triazin-3-yl)-3-methyl-1,2,4-thiadiazol-5-amine (structure) | 5-bromo-3-methyl-1,2,4-thiadiazole and 6-(3-fluoropyridin-4-yl)-5-(pyridin-3-yl)-1,2,4-triazin-3-amine (Intermediate II-1) | 367.0 | 8.84 (s, 1H), 8.73 (s, 1H), 8.65 (m, 1H), 8.46 (s, 1H), 8.10 (m, 1H), 7.925 (m, 1H), 7.77 (s, 1H), 7.54 (m, 1H), 2.56 (s, 3H). |
| 6 | N-(6-(3-fluoropyridin-4-yl)-5-(pyridin-3-yl)-1,2,4-triazin-3-yl)-5-methyl-1,3,4-thiadiazol-2-amine (structure) | 2-bromo-5-methyl-1,3,4-thiadiazole and 6-(3-fluoropyridin-4-yl)-5-(pyridin-3-yl)-1,2,4-triazin-3-amine (Intermediate II-1) | 367.1 | 8.84 (s, 1H), 8.63 (s, 1H), 8.62 (s, 1H), 8.43 (s, 1H), 8.08 (m, 1H), 7.90 (m, 1H), 7.55 (m, 1H), 2.72 (s, 3H). |

Preparation of 6-(3-fluoropyridin-4-yl)-5-(pyridin-3-yl)-1,2,4-triazin-3-amine: (Intermediate II-1)

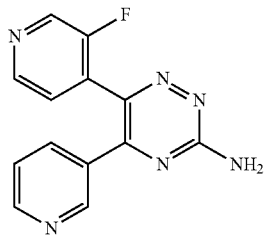

II-1

Step 1: Synthesis of 2-(3-fluoropyridin-4-yl)-1-(pyridin-3-yl)ethan-1-one

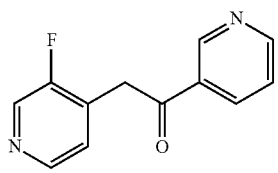 [SMILES: O=C(Cc1ccncc1F)c1cccnc1]

To a cooled (−10° C.) solution of 3-fluoro-4-methylpyridine (22.2 g, 0.2007 mol) in THF (100 mL), was added methyl nicotinate (25 g, 0.1824 mol), followed by LiHMDS (1M hexane, 273 mL, 0.2736 mol) in drop wise. The reaction mixture was allowed to stir at room temperature and the progress of the reaction was monitored by TLC analysis. After completion of the reaction, the reaction mixture was carefully quenched with saturated ammonium chloride solution, extracted with ethyl acetate (2×100 mL). The combined organic layers were washed with brine solution (100 mL), dried over anhydrous sodium sulphate and concentrated under reduced pressure to afford 2-(3-fluoropyridin-4-yl)-1-(pyridin-2-yl)ethan-1-one (14.5 g, 36.8%) as light brown solid. m/z=217.1 [M+H]$^+$ Step 2: 1-(3-fluoropyridin-4-yl)-2-(pyridin-3-yl)ethane-1,2-dione

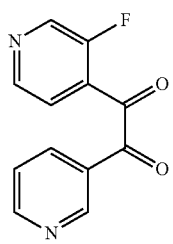 [SMILES: O=C(C(=O)c1ccncc1F)c1cccnc1]

To a stirred solution of 2-(3-fluoropyridin-4-yl)-1-(pyridin-2-yl)ethan-1-one (14.5 g, 0.0671 mol) in DMSO (15 mL), was added hydrobromic acid (48%, 33 mL, 0.2013 mol) at 55° C. After 3 h TLC analysis showed complete conversion of the starting material. The reaction mixture was cooled to room temperature, diluted the reaction with water and solid Na$_2$CO$_3$ was added by adjusting the pH=8. The contents were extracted with ethyl acetate (2×100 mL) and the combined organics were washed with brine solution (100 mL), dried over anhydrous sodium sulphate and concentrated under reduced pressure to afford 1-(3-fluoropyridin-4-yl)-2-(pyridin-3-yl)ethane-1,2-dione (11.5 g, 75.6%). m/z=231.0 [M+H]$^+$.

Step 3: 6-(3-fluoropyridin-4-yl)-5-(pyridin-3-yl)-1,2,4-triazin-3-amine (Intermediate II-1)

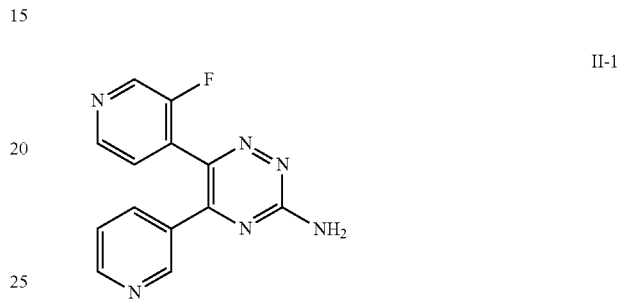

II-1

To a stirred solution 1-(3-fluoropyridin-4-yl)-2-(pyridin-3-yl)ethane-1,2-dione (11.5 g, 0.05 mol) in ethanol (50 mL), was added acetic acid (0.6 mL, 0.01 mol) and aminoguanidine bicarbonate (7.48 g, 0.055 mol). The reaction mixture was heated to 70° C. and the progress of the reaction was monitored by TLC analysis. After 16 h, the reaction was diluted with water, extracted with ethyl acetate (2×150 mL) and the combined organics were washed with brine solution (80 mL), dried over anhydrous sodium sulphate and concentrated under reduced pressure to afford crude material. The crude material was then purified by flash column chromatography on silica gel eluting with 0-45% ethyl acetate in petroleum ether to yield regioisomers. The regioisomers were separated by prep HPLC to afford 6-(3-fluoropyridin-4-yl)-5-(pyridin-3-yl)-1,2,4-triazin-3-amine (1.4 g, 10%) as pale yellow solid. m/z=269.1 [M+H]$^+$.

Step 4: General Procedure for the Preparation of Examples 1 to 6 of Table 1 Through Buchwald Coupling Under nitrogen atmosphere, to a stirred solution of 6-(3-fluoropyridin-4-yl)-5-(pyridin-3-yl)-1,2,4-triazin-3-amine (120 mg, 0.4477 mmol) in anhydrous 1,4-dioxane (4 mL), were added bromo compound (0.4477 mmol), sodium tert-butoxide (107.4 mg, 1.1192 mmol), XPhos Pd G2 (35.1 mg, 0.0447 mmol). The reaction mixture was heated to 120° C. and the progress of the reaction was monitored by TLC analysis. After 16 h, the reaction mixture was cooled to ambient temperature diluted the reaction with water (35 mL), extracted with ethyl acetate (2×50 mL) and combined organics were washed with brine solution (20 mL), dried over anhydrous sodium sulphate and concentrated under reduced pressure to afford crude material. The crude material was purified by prep HPLC to afford final compound.

Synthesis of Example 7

1-(6-(3-fluoropyridin-4-yl)-5-(pyridin-3-yl)-1,2,4-triazin-3-yl)-3-methylurea

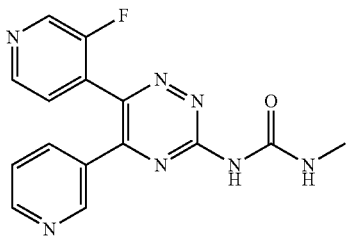

To a stirred solution of 6-(3-fluoropyridin-4-yl)-5-(pyridin-3-yl)-1,2,4-triazin-3-amine (Intermediate II-1) (120 mg, 0.4477 mmol) in THF (4 mL), was added CDI (108.7 mg, 0.6715 mmol), DIPEA (0.22 mL, 1.3431 mmol), reaction mixture stirred at 70° C. for 5 h, then added methyl amine (1.1 mL, 2.2385 mmol), heated to 70° C. under sealed condition. After 10 h stirring, volatiles were removed under reduced pressure to afford crude material. The crude material was purified by prep HPLC to afford 1-(6-(3-fluoropyridin-4-yl)-5-(pyridin-3-yl)-1,2,4-triazin-3-yl)-3-methylurea as off white solid. m/z=326.1 [M+H]$^+$.

1H-NMR (CD$_3$OD): 8.87 (bs, 1H), 8.79 (bs, 1H), 8.64 (m, 1H), 8.50 (s, 1H), 8.21 (m, 1H), 7.91 (m, 1H), 7.68 (m, 1H).

Synthesis of Examples 8 to 13

Table 2 lists the preferred compounds and examples 8-13, respectively, of the present invention, its name, structure, characterizing data such as LCMS and NMR as well as the Intermediates from which they have been prepared.

TABLE 2

| Ex No | Compound | Prepared from | LCMS | NMR (CD$_3$OD) δ |
|---|---|---|---|---|
| 8 | 5-(2-fluorophenyl)-N-(pyridin-3-yl)-6-(2-(trifluoromethyl)pyridin-4-yl)-1,2,4-triazin-3-amine | 3-bromopyridine and 5-(2-fluorophenyl)-6-[2-(trifluoromethyl)-4-pyridyl]-1,2,4-triazin-3-amine (Intermediate II-3) | 411.1 [M − H] | 1H-NMR (400 MHz, MeOD): δ 9.25 (s, 1H), 8.70 (m, 3H), 7.82-7.88 (m, 2H), 7.61-7.74 (m, 3H), 7.35-7.47 (m, 1H), 7.09-7.22 (m, 1H), |
| 9 | 5-(2-fluorophenyl)-N-(pyridin-3-yl)-6-(2-(trifluoromethyl)pyridin-4-yl)-1,2,4-triazin-3-amine | 1-bromo-3-fluoro-benzene and 5-(2-fluorophenyl)-6-[2-(trifluoromethyl)-4-pyridyl]-1,2,4-triazin-3-amine (Intermediate II-3) | 428.1 [M − H] | 1H-NMR (400 MHz, CDCl3): δ 8.73 (m, 1H), (m, 1H), 8.36 (s, 1H), 7.53-7.85 (m, 4H), 7.40-7.46 (m, 2H), 7.11 (q, J = 9.20 Hz, 1H), 6.84 (s, 1H) |
| 10 | 4-chloro-N-(5-(2-fluorophenyl)-6-(2-(trifluoromethyl)pyridin-4-yl)-1,2,4-triazin-3-yl)thiazol-2-amine | 2-bromo-4-chloro-thiazole and 5-(2-fluorophenyl)-6-[2-(trifluoromethyl)-4- | 453.0 [M + H]$^+$ | 1H-NMR (400 MHz, MeOD): δ 8.72 (d, J = 5.04 Hz, 1H), 7.94 (q, J = |

TABLE 2-continued

| Ex No | Compound | Prepared from | LCMS | NMR (CD₃OD) δ |
|---|---|---|---|---|
| | [structure] | pyridyl]-1,2,4-triazin-3-amine (Intermediate II-3) | | −14.84 Hz, 2H), 7.63-7.77 (m, 2H), 7.49 (q, J = 7.56 Hz, 1H), 7.12 (t, J = 8.96 Hz, 1H), 6.98 (s, 1H) |
| 11 | N-(5-(2-fluorophenyl)-6-(2-(trifluoromethyl)pyridin-4-yl)-1,2,4-triazin-3-yl)-3-methyl-1,2,4-thiadiazol-5-amine [structure] | 5-bromo-3-methyl-1,2,4-thiadiazole and 5-(2-fluorophenyl)-6-[2-(trifluoromethyl)-4-pyridyl]-1,2,4-triazin-3-amine (Intermediate II-3) | 431.8 [M − H]⁻ | 1H-NMR (400 MHz, MeOD): δ 8.74 (d, J = 4.80 Hz, 1H), 7.94 (q, J = 19.60 Hz, 2H), 7.66-7.78 (m, 1H), 7.39-7.53 (m, 2H), 7.14 (t, J = 8.80 Hz, 1H), 2.55 (s, 3H) |
| 12 | 5-(2-fluorophenyl)-N-(3-fluorophenyl)-6-(3-fluoropyridin-4-yl)-1,2,4-triazin-3-amine [structure] | 1-bromo-3-fluoro-benzene and 5-(2-fluorophenyl)-6-(3-fluoropyridin-4-yl)-1,2,4-triazin-3-amine (Intermediate II-2) | 380.1 [M + H]⁺ | 1H-NMR (400 MHz, DMSO-d6): δ 0.96 (s, 1H), (m, 1H), 7.57-7.83 (m, 4H), 6.91-7.44 (m, 6H) |
| 13 | N-(5-(2-fluorophenyl)-6-(3-fluoropyridin-4-yl)-1,2,4-triazin-3-yl)-3-methyl-1,2,4-thiadiazol-5-amine [structure] | 5-bromo-3-methyl-1,2,4-thiadiazole and 5-(2-fluorophenyl)-6-(3-fluoropyridin-4-yl)-1,2,4-triazin-3-amine (Intermediate II-2) | 384.0 [M + H]⁺ | 1H-NMR (400 MHz, DMSO-d6): δ 8.46 (t, J = 4.80 Hz, 2H), 7.71 (m, 2H), 7.51 (t, J = 7.40 Hz, 1H), 7.14-7.40 (m, 2H), 2.33 (s, 3H) |

Synthesis of 5-(2-fluorophenyl)-6-(3-fluoropyridin-4-yl)-1,2,4-triazin-3-amine (Intermediate II-2)

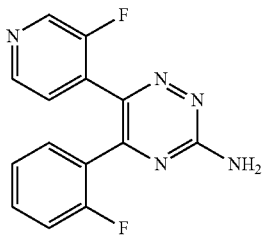

II-2

Step 1: Synthesis of 2,2-dibromo-1-(2-fluorophenyl)ethan-1-one

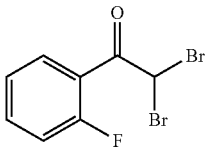 [SMILES: O=C(c1ccccc1F)C(Br)Br]

To a solution of 1-(2-fluorophenyl)ethan-1-one (20 g, 0.144 mol) in anhydrous acetic acid was added bromine in acetic acid (10 ml, 0.188 mol) dropwise and the reaction mixture was heated to 65° C. The progress of the reaction was monitored by TLC analysis. After 16 h, the reaction mixture was cooled to ambient temperature and poured in a beaker containing crushed ice and extracted with ethyl acetate, and organic layer was washed with aqueous sodium thiosulfate and the combined organic layer was concentrated under reduced pressure to yield (35 g, 79%) of the required product. m/z=296.93 [M+H]$^+$.

Step 2: Synthesis of 5-(2-fluorophenyl)-1,2,4-triazin-3-amine

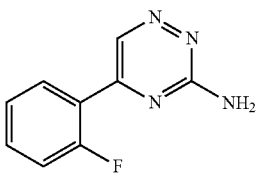 [SMILES: Nc1nncc(-c2ccccc2F)n1]

To a solution of 2,2-dibromo-1-(2-fluorophenyl)ethan-1-one (35 g, 0.118 mol) in anhydrous THF was added morpholine (42 ml, 0.498 mol) and the reaction mixture was heated slowly to 65° C. After 16 h, the reaction mixture was cooled to RT, filtered through celite and washed with DCM. The combined organic layer was concentrated to give crude intermediate which was used for next step without purification.

To a solution of above crude in methanol added amino guanidine bicarbonate (16 g, 0.118 mol), followed by dropwise addition of acetic acid (21 ml, 0.354 mol) over 15 min and heated to 70° C. After 16 h, the reaction mixture was cooled to ambient temperature and extracted with ethyl acetate and concentrated and purified by flash column chromatography to yield (4 g, 18%) of the required product. m/z=191.18 [M+H]$^+$.

Step 3: Synthesis of 6-bromo-5-(2-fluorophenyl)-1,2,4-triazin-3-amine

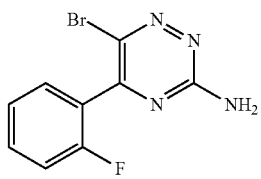 [SMILES: Nc1nnc(Br)c(-c2ccccc2F)n1]

At 0° C., to a solution of 5-(2-fluorophenyl)-1,2,4-triazin-3-amine (4 g, 0.021 mol) in DMF was added NBS (5.5 g 0.0315 mol) as DMF solution. The reaction mixture was allowed to stir at ambient temperature and the progress of the reaction was monitored by TLC analysis. After 16 h, the reaction mixture was quenched with ice and the resultant solid was filtered and dried to yield (4 g, 71%) of the required product. m/z=270 [M+H]$^+$.

Step 4: Synthesis of 5-(2-fluorophenyl)-6-(3-fluoropyridin-4-yl)-1,2,4-triazin-3-amine (Intermediate II-2)

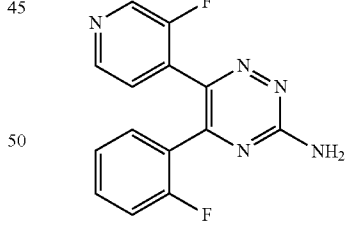

II-2

Under nitrogen atmosphere to a stirred solution of 6-bromo-5-(2-fluorophenyl)-1,2,4-triazin-3-amine (3 g 0.011 mol) in 1,4-dioxane:water (2:1) were added 3-fluoro-4-(4,4,5,5-tetramethyl-1,3,2-dioxaborolan-2-yl)pyridine (3.7 g 0.0167 mol), cesium carbonate (7 g 0.022 mol) and Pd(dppf)Cl$_2$ (0.6 g 0.008 mol). The reaction mixture was degassed and backfilled with nitrogen and heated in microwave reactor. After 1 h, the reaction mixture was filtered through celite. The filtrate was concentrated and purified by flash column chromatography to yield (400 mg, 13%) of the required product. m/z=286.2 [M+H]$^+$.

Step 5: Synthesis of 5-(2-fluorophenyl)-6-[2-(trifluoromethyl)-4-pyridyl]-1,2,4-triazin-3-amine (Intermediate II-3

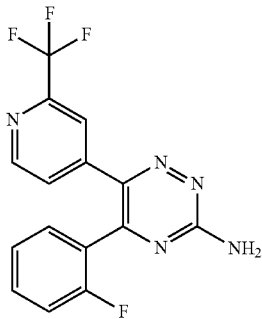

II-3

Under nitrogen atmosphere to a stirred solution of 6-bromo-5-(2-fluorophenyl)-1,2,4-triazin-3-amine (1 g 0.0037 mmol) in 1,4-dioxane:water (2:1) were added 2-(trifluoromethyl)pyridine-4-boronic acid, pinacol ester (1.24 g 0.0055 mmol), sodium carbonate (1.1 g 0.011 mol) and tetrakis(triphenylphosphine)palladium (430 mg 0.0037 mol). The reaction mixture was degassed and backfilled with nitrogen and heated in microwave reactor. After 1 h, the reaction mixture was filtered through celite. The filtrate was concentrated and purified by flash column chromatography to yield (400 mg, 33%) of the required product. m/z=336.2 [M+H]$^+$.

Step 6: General Procedure for the Preparation of Examples 8 to 13 of Table 2 Through Buchwald Coupling Under nitrogen atmosphere to a stirred solution of 5-(2-fluorophenyl)-6-(3-fluoropyridin-4-yl)-1,2,4-triazin-3-amine (intermediate II-2) (0.1 g 0.35 mol) or 5-(2-fluorophenyl)-6-[2-(trifluoromethyl)-4-pyridyl]-1,2,4-triazin-3-amine (Intermediate II-3) (0.1 g, 0.3 mol) in anhydrous 1,4-dioxane were added corresponding aryl or heteroaryl bromide (1.5 eq), t-butyl Xphos Pd G1 precatalyst (10 mg), sodium tertiarybutoxide (0.057 g, 0.59 mmol). The reaction mixture was heated to 120° C. microwave reactor. After 1 h, the reaction mixture was filtered through celite. The filtrate was concentrated and the crude product thus obtained was purified by preparative HPLC to yield the desired product.

Synthesis of Examples 14 and 15

Table 3 lists the preferred compounds and examples 14 and 15, respectively, of the present invention, its name, structure, characterizing data such as LCMS and NMR as well as the Intermediates from which they have been prepared.

TABLE 3

| Ex No | Compound | Prepared from | LCMS [M + H]$^+$ | NMR |
|---|---|---|---|---|
| 14 | 5-(2-fluorophenyl)-6-(3-fluoropyridin-4-yl)-N-(3-methyl-1H-pyrazol-5-yl)-1,2,4-triazin-3-amine | 3-methyl-1H-pyrazol-5-amine and 5-(2-fluorophenyl)-6-(3-fluoropyridin-4-yl)-3-iodo-1,2,4-triazine (Intermediate V-1) | 366.1 | 1H-NMR (400 MHz, MeOD): δ 8.51 (q, J = 1.60 Hz, 2H), 7.73 (m, 2H), 7.55 (d, J = 8.40 Hz, 1H), 7.36 (t, J = 7.20 Hz, 1H), 7.13 (q, J = 9.20 Hz, 1H), 5.49 (s, 1H), 2.24 (s, 3H) |
| 15 | 5-(2-fluorophenyl)-6-(3-fluoropyridin-4-yl)-N-(3-methyl-1H-1,2,4-triazol-5-yl)-1,2,4-triazin-3-amine | 3-methyl-1H-1,2,4-triazol-5-amine and 5-(2-fluorophenyl)-6-(3-fluoropyridin-4-yl)-3-iodo-1,2,4-triazine (Intermediate V-1) | 367.1 | 1H-NMR (400 MHz, MeOD): δ 8.54 (q, J = 1.60 Hz, 2H), 7.76 (m, 2H), 7.58 (d, J = 6.80 Hz, 1H), 7.39 (t, J = 7.60 Hz, 1H), 7.13 (t, J = 9.20 Hz, 1H), 2.38 (s, 3H) |

Synthesis of 5-(2-fluorophenyl)-6-(3-fluoropyridin-4-yl)-3-iodo-1,2,4-triazine (Intermediate V-1)

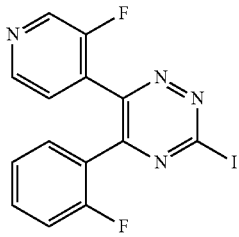

V-1

Alternative Synthesis of 5-(2-fluorophenyl)-6-(3-fluoropyridin-4-yl)-1,2,4-triazin-3-amine (Intermediate II-2)

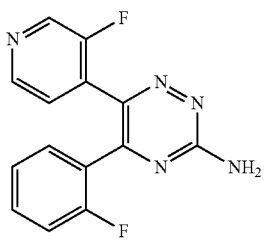

II-2

Step 1: Synthesis of 1-(2-fluorophenyl)-2-(3-fluoropyridin-4-yl) ethan-1-one

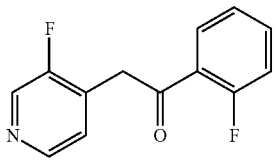 [SMILES: O=C(Cc1ccncc1F)c1ccccc1F]

At −78° C., to a stirred solution of 3-fluoro-4-methylpyridine (10 g, 0.064 mol) in THF (100 mL), was added LiHMDS (80 mL, 1M hexane, 0.083 mol) and the reaction mixture was allowed to stir at the same temperature. After 15 minutes a solution of methyl 2-fluorobenzoate (7.2 g, 0.064 mol) in THF was added and the reaction mixture was allowed to stir at ambient temperature. After 3 h, TLC analysis indicated complete conversion of the starting material. The reaction mixture was carefully quenched with saturated ammonium chloride solution (50 mL), extracted with ethyl acetate (2×100 mL). The combined organic layers were washed with brine solution (100 mL), dried over anhydrous sodium sulphate and concentrated under reduced pressure to afford 1-(2-fluorophenyl)-2-(3-fluoropyridin-4-yl)ethan-1-one (14 g, 36.8%) as light brown oil which was taken to the next step without further purification. LCMS: m/z=234 [M+H]$^+$.

Step 2: Synthesis of 1-(2-fluorophenyl)-2-(3-fluoropyridin-4-yl) ethane-1,2-dione

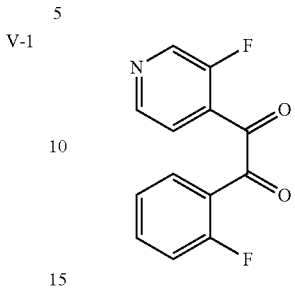

To a stirred solution of 1-(2-fluorophenyl)-2-(3-fluoropyridin-4-yl) ethan-1-one (14 g, 0.060 mol) in DMSO (50 mL), was added hydrobromic acid (48%, 28 mL, 0.180 mol) at 55° C. After 16 h, TLC analysis showed complete conversion of the starting material. The reaction mixture was cooled to room temperature, diluted with water and solid Na$_2$CO$_3$ was added by adjusting the pH=8. The contents were extracted with ethyl acetate (2×100 mL) and the combined organics were washed with brine solution (100 mL), dried over anhydrous sodium sulphate and concentrated under reduced pressure to afford 1-(2-fluorophenyl)-2-(3-fluoropyridin-4-yl)ethane-1,2-dione (8 g, 54%). LCMS: m/z=248.0 [M+H]$^+$.

Step 3: Synthesis of 5-(2-fluorophenyl)-6-(3-fluoropyridin-4-yl)-1,2,4-triazin-3-amine (Intermediate II-2)

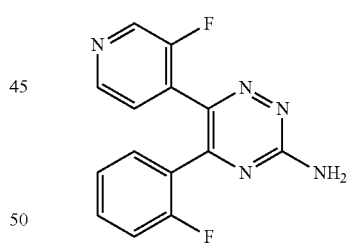

II-2

To a stirred solution 1-(2-fluorophenyl)-2-(3-fluoropyridin-4-yl) ethane-1,2-dion (8 g, 0.032 mol) in ethanol (50 mL), was added acetic acid (0.8 mL, 0.012 mol) and amino guanidine bicarbonate (4.8 g, 0.0356 mol). The reaction mixture was heated to 70° C. and the progress of the reaction was monitored by TLC analysis. After 16 h, the reaction was diluted with water, extracted with ethyl acetate (2×150 mL) and the combined organics were washed with brine solution (80 mL), dried over anhydrous sodium sulphate and concentrated under reduced pressure. The residue thus obtained was then purified by flash column chromatography on silica gel (230-400 mesh) eluting with 0-45% ethyl acetate in petroleum ether to yield required compound (0.8 g, 8%) as pale yellow solid. LCMS: m/z=286.0 [M+H]$^+$.

Step 4: Synthesis of 5-(2-fluorophenyl)-6-(3-fluoropyridin-4-yl)-3-iodo-1,2,4-triazine (Intermediate V-1)

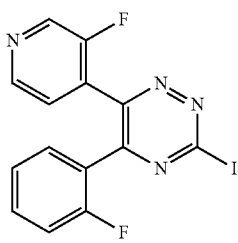

V-1

To a stirred solution 5-(2-fluorophenyl)-6-(3-fluoropyridin-4-yl)-1,2,4-triazin-3-amine (0.5 g, 0.0017 mol) in diiodomethane (10 mL), was added isoamyl nitrite (2.3 mL, 0.017 mol) at 0° C. and then the reaction mixture was heated to 60° C. The progress of the reaction was monitored by TLC analysis. After 16, the reaction mixture was cooled to ambient temperature and the volatiles were removed under reduced pressure. The residue was then purified by flash column chromatography on silica gel (230-400 mesh) to yield required compound (0.25 g, 36%) as brown gummy solid. LCMS m/z=397.0 [M+H]$^+$.

Step 5: General Procedure for the Preparation of Example 14 and 15 of Table 3

To a stirred solution of 5-(2-fluorophenyl)-6-(3-fluoropyridin-4-yl)-3-iodo-1,2,4-triazine (100 mg, 0.252 mmol) in IPA (2 mL), were added corresponding aryl or heteroaryl amine (0.378 mmol), DIPEA (97 mg, 0.756 mmol). The reaction mixture was heated to 80° C. and the progress of the reaction was monitored by TLC analysis. After 16 h, the reaction mixture was cooled to ambient temperature, concentrate under reduced pressure and the residue was purified by prep HPLC using Column: Atlantis dC18 (50*4.6) 5μ Mobile phase: A: 0.1% Formic Acid in H$_2$O B: ACN, Flow Rate: 1.5 ml/min.

Synthesis of Example 16

1-(5-(2-fluorophenyl)-6-(3-fluoropyridin-4-yl)-1,2,4-triazin-3-yl)-3-methylurea

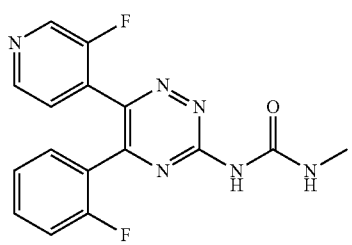

16

Under nitrogen atmosphere. to a stirred solution of 5-(2-fluorophenyl)-6-(3-fluoropyridin-4-yl)-3-iodo-1,2,4-triazine (Intermediate V-1) (100 mg, 0.252 mmol) in 1,4-dioxane was added N-methyl urea (28 mg, 0.378 mmol), sodium tert-butoxide (72 mg, 0.756 mmol), Ruphos pre-catalyst (10 mg) and the reaction mixture was heated to 60° C. for 2 h. The progress of the reaction was monitored by TLC analysis and then reaction mixture was filtered through celite and the filtrate was concentrated and purified by prep HPLC using Column: Atlantis dC18 (50*4.6) 5μ Mobile phase: A: 0.1% Formic Acid in H$_2$O B: ACN, Flow Rate: 1.5 ml/min. LC-MS: m/z 343.1 [M+H]$^+$. 1H-NMR (400 MHz, MeOD): δ 8.49 (s, 2H), 7.67 (m, 1H), 7.55-7.61 (m, 1H), 7.49-7.54 (m, 1H), 7.32-7.36 (m, 1H), 7.08 (q, J=8.40 Hz, 1H), 2.98 (s, 3H).

Synthesis of Example 17

N-(3-fluorophenyl)-6-(3-fluoropyridin-4-yl)-5-(5-methyloxazol-2-yl)-1,2,4-triazin-3-amine

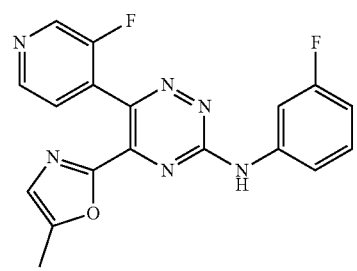

17

Synthesis of 6-(3-fluoro-4-pyridyl)-5-(5-methyloxazol-2-yl)-1,2,4-triazin-3-amine (Intermediate II-4)

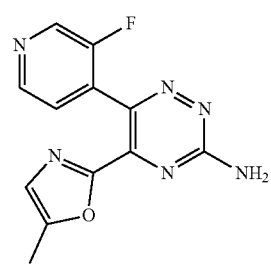

II-4

Step 1: Synthesis of ethyl 2-oxo-2-((2-oxopropyl)amino) acetate

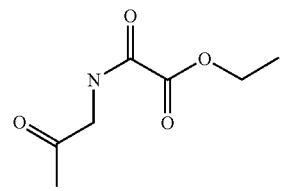

Triethylamine (98 ml, 0.702 mol) was added dropwise to a stirred solution of aminopropan-2-one hydrochloride (35.0 g, 0.319 mol) in anhydrous toluene (400 ml). A solution of ethyl oxalyl chloride (42 ml, 0.382 mol) was added drop wise over 15 min at 45° C. The reaction mixture was then refluxed for 2.5 h, and slowly allowed to stir at ambient temperature. After 16 h, the reaction mixture was poured into ice cold water and the contents were extracted with ethyl acetate (200 mL), washed with aqueous sodium bicarbonate solution (500 ml), dried over sodium sulphate and concentrated to afford the title compound (25 g, crude) as dark brown liquid. The crude was taken to the next step without further purification.

Step 2: Synthesis of ethyl 5-methyloxazole-2-carboxylate

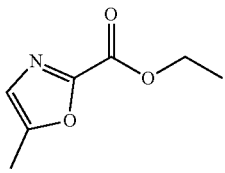

To a stirred solution of ethyl 2-oxo-2-((2-oxopropyl) amino) acetate (25 g, 0.144 mol) in anhydrous toluene (300 mL) was added phosphorous oxychloride (13 mL, 0.144 mmol) and the reaction mixture was heated to 100° C. After 16 hours, the reaction mixture was cooled to ambient temperature and carefully poured into ice water (200 mL). The contents were extracted with ethyl acetate (200 mL) washed with saturated sodium bicarbonate solution (2×100 mL), water (2×100 mL), dried over sodium sulphate and concentrated under reduced pressure. The crude material was purified by silica gel column chromatography eluting with 0-50% ethyl acetate in petroleum ether to afford the title compound (7 g, 31%) as brown oil.

Step 3: Synthesis of 2-(3-fluoropyridin-4-yl)-1-(5-methyloxazol-2-yl) ethan-1-one

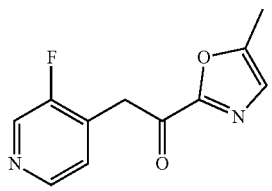 [SMILES: Cc1cnc(C(=O)Cc2ccncc2F)o1]

At −78° C., to a stirred solution of 3-fluoro-4-methylpyridine (5.1 g, 0.045 mol) in anhydrous tetrahydrofuran (70 mL), was added LiHMDS (1M in hexane) (45 ml, 0.045 mol) drop wise. The reaction mixture was allowed to stir at −78° C. for 15 min and then added ethyl 5-methyloxazole-2-carboxylate (7 g, 0.045 mol). The reaction mixture was allowed to stir at ambient temperature and the progress of the reaction was monitored by TLC analysis. After completion of the reaction, the reaction mixture was carefully quenched with saturated ammonium chloride solution and extracted with ethyl acetate (2×100 mL). The combined organic layers were washed with brine solution (100 mL), dried over anhydrous sodium sulphate and concentrated under reduced pressure to afford 2-(3-fluoropyridin-4-yl)-1-(5-methyloxazol-2-yl)ethan-1-one (5 g, 50%) as brown oil. The crude material was taken further without purification. LCMS: m/z=221[M+H]$^+$.

Step 4: Synthesis of 6-(3-fluoropyridin-4-yl)-5-(5-methyloxazol-2-yl)-1,2,4-triazin-3-amine (Intermediate II-4)

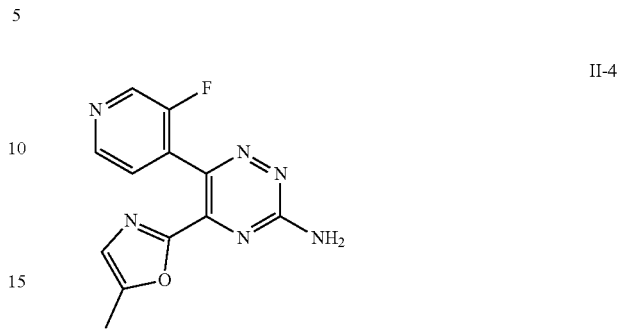

II-4

To a stirred solution of 2-(3-fluoropyridin-4-yl)-1-(5-methyloxazol-2-yl) ethan-1-one (5 g, 0.022 mol) in DMF was added DABCO (1.01 g, 0.009 mol), amino guanidine bicarbonate (4.4 g, 0.033 mol) and acetic acid (1.3 ml, 0.022 mol). The reaction mixture was heated to 90° C. and the progress of the reaction was monitored by TLC analysis. After 16 h, the reaction mixture was cooled to ambient temperature cooling to room temperature and the volatiles were removed under reduced pressure. The residue thus obtained was purified by silica gel (230-400 mesh) column chromatography, eluting with 0-5% methanol in dichloromethane afford the desired compound (500 mg, 10%) in an about 1:1 mixture with its regioisomer 5-(3-fluoro-4-pyridyl)-6-(5-methyloxazol-2-yl)-1,2,4-triazin-3-amine. Pale yellow solid, 500 mg, 10%. The mixture was directly used in the next reaction step.

Step 5: Synthesis of N-(3-fluorophenyl)-6-(3-fluoropyridin-4-yl)-5-(5-methyloxazol-2-yl)-1,2,4-triazin-3-amine (Example 17)

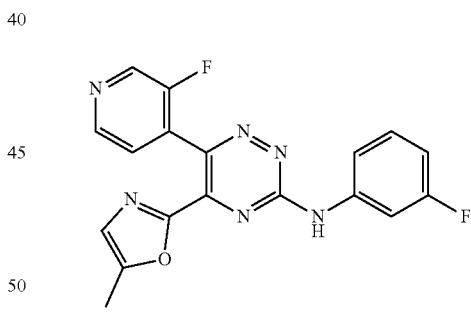

To a stirred solution of a 1:1 mixture 6-(3-fluoropyridin-4-yl)-5-(5-methyloxazol-2-yl)-1,2,4-triazin-3-amine with its regioiosmer isomer 5-(3-fluoro-4-pyridyl)-6-(5-methyloxazol-2-yl)-1,2,4-triazin-3-amine (400 mg, 1.470 mmol) in anhydrous 1,4-dioxane under nitrogen atmosphere was added 1-fluoro-3-iodobenzene (326.4 mg, 1.470 mmol), sodium tert-butoxide (423 mg, 4.41 mmol), xantphos (80 mg 0.147 mmol), Pd$_2$(dba)$_3$ (60 mg 0.0705 mmol). The reaction mixture was heated to 85° C. and the progress of the reaction was monitored by TLC analysis. After 16 h, the reaction mixture was cooled to ambient temperature and filtered through a pad of celite. The filtrate was concentrated under reduced pressure and the residue thus obtained was purified by reverse phase preparatory HPLC using Column: ZORBAX XDB C-18 (50×4.6 mm) 3.5 μm, Mobile Phase: A:

0.1% HCOOH in H$_2$O: ACN (95:5), Mobile phase: B: ACN, Flow Rate: 1.5 ml/min to yield the mixture of regio-isomers (20 mg) as pale yellow solid. The two regioisomers were separated by reverse phase preparatory HPLC using Column: X-bridge C-18 (150×19 mm) 5 μm, Mobile Phase: 10 mM ammonium bicarbonate in water/ACN, Flow Rate: 1.5 ml/min to afford the two isomers (F1: 3.5 mg) and (F2: 3.1 mg). Isomer F1: Rt=1.90 min. LCMS [M+H]$^+$ m/z=367.1. 400 MHz, DMSO-d$_6$: δ 11.13 (s, 1H), 8.67 (t, J=4.08 Hz, 2H), 7.41-7.43 (m, 4H), 6.93 (t, J=8.84 Hz, 2H), 2.38 (s, 3H). Isomer F2: Rt=1.97 min. LCMS [M+H]$^+$ m/z=367.1. 400 MHz, MeOD: δ 8.56 (q, J=1.88 Hz, 2H), 7.79-7.81 (m, 2H), 7.57 (q, J=1.28 Hz, 1H), 7.01-7.01 (m, 1H), 7.01-7.01 (m, 1H), 2.43 (s, 3H). The desired structure was tentatively assigned to this isomer F2 based on the much higher biological activity over isomer F1.

Synthesis of Examples 18 to 48

Table 4 lists further preferred compounds and examples 18-48 respectively, of the present invention, its name, structure, as well as the Intermediates and the procedures for their preparation.

TABLE 4

| Ex No | Compound | Prepared from | Method / Procedure |
|---|---|---|---|
| 18 | N-(3-ethyl-1H-1,2,4-triazol-5-yl)-5-(2-fluorophenyl)-6-(3-fluoro-4-pyridyl)-1,2,4-triazin-3-amine | N-SEM protected heteroaryl bromide 3-bromo-5-ethyl-1-{[2-(trimethylsilyl)ethoxy]-methyl}-1H-1,2,4-triazole and 5-(2-fluorophenyl)-6-(3-fluoropyridin-4-yl)-1,2,4-triazin-3-amine (Intermediate II-2). LCMS: m/z = 381.2 [M + H]$^+$. | In analogy to the preparation of Examples 8 to 13 of Table 2 except that the coupling was Cu catalysed instead of Pd catalysis* |
| 19 | [5-[[5-(2-fluorophenyl)-6-(3-fluoro-4-pyridyl)-1,2,4-triazin-3-yl]amino]-1H-1,2,4-triazol-3-yl]methanol | (5-Amino-1H-1,2,4-triazol-3-yl)methanol and 5-(2-fluorophenyl)-6-(3-fluoropyridin-4-yl)-3-iodo-1,2,4-triazine (Intermediate V-1) | In analogy to the preparation of Examples 14, 15 of Table 3. |
| 20 | N-[3-[(dimethylamino)methyl]-1H-1,2,4-triazol-5-yl]-5-(2-fluorophenyl)-6-(3-fluoro-4-pyridyl)-1,2,4-triazin-3-amine | N-SEM protected heteroaryl bromide [(5-bromo-1-{[2-(trimethylsilyl)ethoxy]methyl}-1H-1,2,4-triazol-3-yl)methyl]dimethylamine and 5-(2-fluorophenyl)-6-(3-fluoropyridin-4-yl)-1,2,4-triazin-3-amine (Intermediate II-2).) LCMS: m/z = 410.2 [M + H]$^+$. As dihydrochloride. | In analogy to the preparation of Examples 8 to 13 of Table 2. By Cu - catalyzed cross-coupling instead of Pd -catalyzed cross-coupling as described in example 18, this Table 4. |
| 21 | 5-(2-fluorophenyl)-6-(3-fluoro-4-pyridyl)-N-(6-methyl-3-pyridyl)-1,2,4-triazin-3-amine | 5-bromo-2-methyl-pyridine and 5-(2-fluorophenyl)-6-(3-fluoropyridin-4-yl)-1,2,4- | In analogy to the preparation of Examples 8 to 13 of |

TABLE 4-continued

| Ex No | Compound | Prepared from | Method / Procedure |
|---|---|---|---|
| | [structure] | triazin-3-amine (Intermediate II-2)<br>LCMS: m/z = 377.2 [M + H]+. | Table 2. |
| 22 | [5-[[5-(2-fluorophenyl)-6-(3-fluoro-4-pyridyl)-1,2,4-triazin-3-yl]amino]-2-pyridyl]methanol<br>[structure] | (5-bromo-2-pyridyl)methanol and 5-(2-fluorophenyl)-6-(3-fluoropyridin-4-yl)-1,2,4-triazin-3-amine (Intermediate II-2) LCMS: m/z = 393.0 [M + H]+. | In analogy to the preparation of Examples 8 to 13 of Table 2. |
| 23 | 5-(2-fluorophenyl)-6-(3-fluoro-4-pyridyl)-N-(6-methoxy-3-pyridyl)-1,2,4-triazin-3-amine<br>[structure] | 5-bromo-2-methoxy-pyridine and 5-(2-fluorophenyl)-6-(3-fluoropyridin-4-yl)-1,2,4-triazin-3-amine (Intermediate II-2)<br>LCMS: m/z = 393.2 [M + H]+. | In analogy to the preparation of Examples 8 to 13 of Table 2. |
| 24 | 5-(2-fluorophenyl)-6-(3-fluoro-4-pyridyl)-N-[6-(trifluoromethyl)-3-pyridyl]-1,2,4-triazin-3-amine<br>[structure] | 5-bromo-2-(trifluoromethyl)pyridine and 5-(2-fluorophenyl)-6-(3-fluoropyridin-4-yl)-1,2,4-triazin-3-amine (Intermediate II-2)<br>LCMS: m/z = 431.2 [M + H]+. | In analogy to the preparation of Examples 8 to 13 of Table 2. |
| 25 | 1-(3-chlorophenyl)-3-[6-(3-fluoro-4-pyridyl)-5-(3-pyridyl)-1,2,4-triazin-3-yl]urea<br>[structure] | 3-Chloroaniline and 6-(3-fluoropyridin-4-yl)-5-(pyridin-3-yl)-1,2,4-triazin-3-amine. | In analogy to Example 7 |

TABLE 4-continued

| Ex No | Compound | Prepared from | Method / Procedure |
|---|---|---|---|
| 26 | 1-[6-(3-fluoro-4-pyridyl)-5-(3-pyridyl)-1,2,4-triazin-3-yl]-3-(4-methoxyphenyl)urea | 4-methoxyaniline and 6-(3-fluoropyridin-4-yl)-5-(pyridin-3-yl)-1,2,4-triazin-3-amine | In analogy to Example 7 |
| 27 | 1-[6-(3-fluoro-4-pyridyl)-5-(3-pyridyl)-1,2,4-triazin-3-yl]-3-(2-morpholinoethyl)urea | 2-morpholinoethanamine and 6-(3-fluoropyridin-4-yl)-5-(pyridin-3-yl)-1,2,4-triazin-3-amine | In analogy to Example 7 |
| 28 | 1-(3-chlorophenyl)-3-[5-(2-fluorophenyl)-6-(3-fluoro-4-pyridyl)-1,2,4-triazin-3-yl]urea | 3-Chloroaniline and 5-(2-fluorophenyl)-6-(3-fluoropyridin-4-yl)-1,2,4-triazin-3-amine (Intermediate II-2) LCMS: m/z = 439.0 [M + H]⁺. | In analogy to Example 7 by preparing first the isocyanate from 3-chloroanilne |
| 29 | 1-[5-(2-fluorophenyl)-6-(3-fluoro-4-pyridyl)-1,2,4-triazin-3-yl]-3-(4-methoxyphenyl)urea | 3-Methoxyaniline and 5-(2-fluorophenyl)-6-(3-fluoropyridin-4-yl)-1,2,4-triazin-3-amine (Intermediate II-2) LCMS: m/z = 435.4 [M + H]⁺. | In analogy to Example 7 by preparing first the isocyanate from 4-ethoxyaniline |
| 30 | 1-[5-(2-fluorophenyl)-6-(3-fluoro-4-pyridyl)-1,2,4-triazin-3-yl]-3-(2-morpholinoethyl)urea | 2-morpholinoethanamine 4-ethoxyaniline and 5-(2-fluorophenyl)-6-(3- | In analogy to Example 7 by preparing first the |

TABLE 4-continued

| Ex No | Compound | Prepared from | Method / Procedure |
|---|---|---|---|
|  | 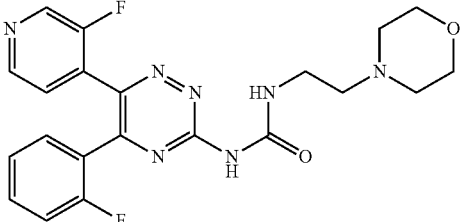 | fluoropyridin-4-yl)-1,2,4-triazin-3-amine (Intermediate II-2) LCMS: m/z = 442.2 [M + H]+. | isocyanate from 2-morpholinoethan-amine 4-ethoxy-aniline |
| 31 | N-(3-cyclopropyl-1H-1,2,4-triazol-5-yl)-5-(2-fluorophenyl)-6-(3-fluoro-4-pyridyl)-1,2,4-triazin-3-amine 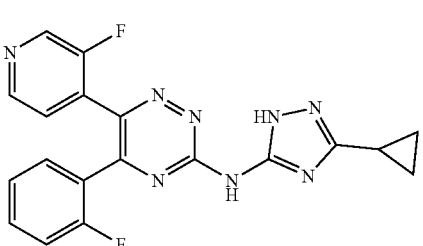 | N-SEM protected heteroaryl bromide 5-bromo-3-cyclopropyl-1-{[2-(trimethylsilyl)ethoxy]methyl}-1H-1,2,4-triazole and 5-(2-fluorophenyl)-6-(3-fluoropyridin-4-yl)-1,2,4-triazin-3-amine (Intermediate II-2). LCMS: m/z = 393.2 [M + H]+. | In analogy to the preparation of Examples 8 to 13 of Table 2. By Cu-catalyzed cross-coupling instead of Pd-catalyzed cross-coupling as described in example 18, this table 4. |
| 32 | 5-(2-fluorophenyl)-6-(3-fluoro-4-pyridyl)-N-[3-(trifluoromethyl)-1H-pyrazol-5-yl]-1,2,4-triazin-3-amine 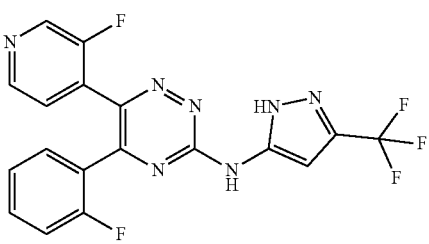 [SMILES: Fc1cnccc1-c1nnc(Nc2cc(C(F)(F)F)n[nH]2)nc1-c1ccccc1F] | 3-(Trifluoromethyl)-1H-pyrazol-5-amine and 5-(2-fluorophenyl)-6-(3-fluoropyridin-4-yl)-3-iodo-1,2,4-triazine (Intermediate V-1) | In analogy to the preparation of Examples 14, 15 of Table 3. |
| 33 | N-(3-ethyl-1H-pyrazol-5-yl)-5-(2-fluorophenyl)-6-(3-fluoro-4-pyridyl)-1,2,4-triazin-3-amine 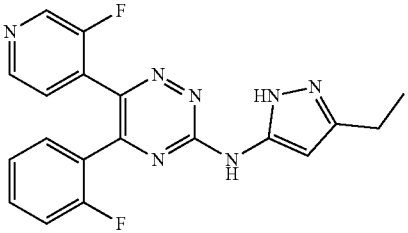 [SMILES: CCc1cc(Nc2nnc(-c3ccncc3F)c(-c3ccccc3F)n2)[nH]n1] | 3-ethyl-1H-pyrazol-5-amine and 5-(2-fluorophenyl)-6-(3-fluoropyridin-4-yl)-3-iodo-1,2,4-triazine (Intermediate V-1) | In analogy to the preparation of Examples 14, 15 of Table 3. |
| 34 | N-(3-cyclopropyl-1H-pyrazol-5-yl)-5-(2-fluorophenyl)-6-(3-fluoro 4-pyridyl)-1,2,4-triazin-3-amine 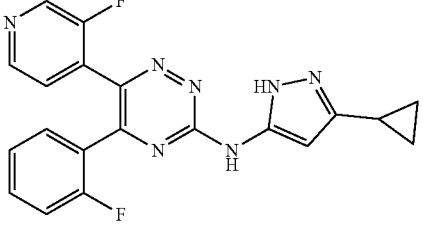 | 3-cyclopropyl-1H-pyrazol-5-amine and 5-(2-fluorophenyl)-6-(3-fluoropyridin-4-yl)-3-iodo-1,2,4-triazine (Intermediate V-1) | In analogy to the preparation of Examples 14, 15 of Table 3. |

TABLE 4-continued

| Ex No | Compound | Prepared from | Method / Procedure |
|---|---|---|---|
| 35 | 1-cyclopropyl-3-[5-(2-fluorophenyl)-6-(3-fluoro-4-pyridyl)-1,2,4-triazin-3-yl]urea 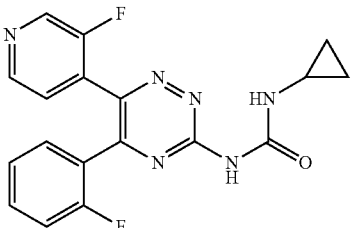 | cyclopropylamine and 5-(2-fluorophenyl)-6-(3-fluoropyridin-4-yl)-1,2,4-triazin-3-amine (Intermediate II-2) LCMS: m/z = 369.4 [M + H]$^+$. | In analogy to Example 7 by preparing first the isocyanate from cyclopropylamine |
| 36 | N-[6-(2,2-difluoroethoxy)pyridin-3-yl]-5-(2-fluorophenyl)-6-(3-fluoropyridin-4-yl)-1,2,4-triazin-3-amine 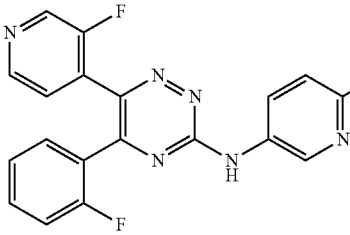 | 5-bromo-2-(2,2-difluoroethoxy)pyridine and 5-(2-fluorophenyl)-6-(3-fluoropyridin-4-yl)-1,2,4-triazin-3-amine (Intermediate II-2) LCMS: m/z = 443.2 [M + H]$^+$. | In analogy to the preparation of Examples 8 to 13 of Table 2. |
| 37 | (2-fluoro-4-{[5-(2-fluorophenyl)-6-(3-fluoropyridin-4-yl)-1,2,4-triazin-3-yl]amino}phenyl)methanol 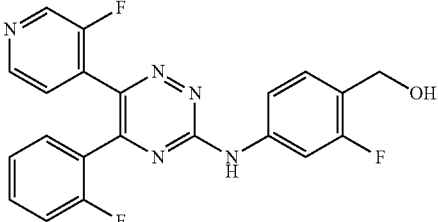 | (4-bromo-2-fluorophenyl)methanol and 5-(2-fluorophenyl)-6-(3-fluoropyridin-4-yl)-1,2,4-triazin-3-amine (Intermediate II-2) LCMS: m/z = 410.2 [M + H]$^+$. | In analogy to the preparation of Examples 8 to 13 of Table 2. |
| 38 | 2-(5-{[5-(2-fluorophenyl)-6-(3-fluoropyridin-4-yl)-1,2,4-triazin-3-yl]amino}pyridin-2-yl)propan-2-ol 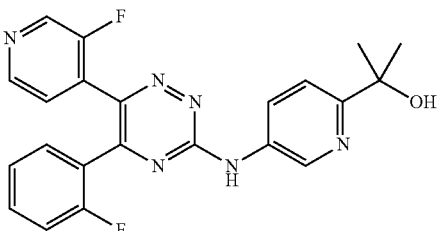 | 2-(5-bromopyridin-2-yl)propan-2-ol and 5-(2-fluorophenyl)-6-(3-fluoropyridin-4-yl)-1,2,4-triazin-3-amine (Intermediate II-2) LCMS: m/z = 421.2 | In analogy to the preparation of Examples 8 to 13 of Table 2. |
| 39 | (5-{[5-(2-fluorophenyl)-6-(3-fluoropyridin-4-yl)-1,2,4-triazin-3-yl]amino}pyrimidin-2-yl)methanol | (5-bromopyrimidin-2-yl)methanol and 5-(2-fluorophenyl)-6-(3-fluoropyridin-4-yl)-1,2,4- | In analogy to the preparation of Examples 8 to 13 of Table 2. |

TABLE 4-continued

| Ex No | Compound | Prepared from | Method / Procedure |
|---|---|---|---|
| | | triazin-3-amine (Intermediate II-2)<br>LCMS: m/z = 394.2 | |
| 40 | 1-(5-{[5-(2-fluorophenyl)-6-(3-fluoropyridin-4-yl)-1,2,4-triazin-3-yl]amino}pyridin-2-yl)ethan-1-ol | 1-(5-bromopyridin-2-yl)ethan-1-ol and 5-(2-fluorophenyl)-6-(3-fluoropyridin-4-yl)-1,2,4-triazin-3-amine (Intermediate II-2)<br>LCMS: m/z = 407.2 | In analogy to the preparation of Examples 8 to 13 of Table 2. |
| 41 | 3-(5-{[5-(2-fluorophenyl)-6-(3-fluoropyridin-4-yl)-1,2,4-triazin-3-yl]amino}pyridin-2-yl)oxetan-3-ol | 3-(5-bromopyridin-2-yl)oxetan-3-ol and 5-(2-fluorophenyl)-6-(3-fluoropyridin-4-yl)-1,2,4-triazin-3-amine (Intermediate II-2)<br>LCMS: m/z = 435.0 | In analogy to the preparation of Examples 8 to 13 of Table 2. |
| 42 | 5-(2-fluorophenyl)-6-(3-fluoropyridin-4-yl)-N-[6-(propan-2-yl)pyridin-3-yl]-1,2,4-triazin-3-amine | 5-bromo-2-(propan-2-yl)pyridine and 5-(2-fluorophenyl)-6-(3-fluoropyridin-4-yl)-1,2,4-triazin-3-amine (Intermediate II-2)<br>LCMS: m/z = 405.0 | In analogy to the preparation of Examples 8 to 13 of Table 2. |
| 43 | 1-(5-{[5-(2-fluorophenyl)-6-(3-fluoropyridin-4-yl)-1,2,4-triazin-3-yl]amino}pyridin-2-yl)-2-methylpropan-1-ol | 1-(5-bromopyridin-2-yl)-2-methylpropan-1-ol and 5-(2-fluorophenyl)-6-(3-fluoropyridin-4-yl)-1,2,4-triazin-3-amine (Intermediate | In analogy to the preparation of Examples 8 to 13 of Table 2. |

TABLE 4-continued

| Ex No | Compound | Prepared from | Method / Procedure |
|---|---|---|---|
| | [structure] | II-2)<br>LCMS: m/z = 435.0 | |
| 44 | N-(6-cyclopropylpyridin-3-yl)-5-(2-fluorophenyl)-6-(3-fluoropyridin-4-yl)-1,2,4-triazin-3-amine<br><br>[structure] | 5-bromo-2-cyclopropylpyridine and 5-(2-fluorophenyl)-6-(3-fluoropyridin-4-yl)-1,2,4-triazin-3-amine (Intermediate II-2). LCMS: m/z = 403.0 | In analogy to the preparation of Examples 8 to 13 of Table 2. |
| 45 | 5-(2-fluorophenyl)-6-(3-fluoropyridin-4-yl)-N-[3-(propan-2-yl)-1H-1,2,4-triazol-5-yl]-1,2,4-triazin-3-Amine<br><br>[structure] | N-SEM protected heteroaryl bromide 5-bromo-3-(propan-2-yl)-1-{[2-(trimethylsilyl)ethoxy]methyl}-1H-1,2,4-triazole and 5-(2-fluorophenyl)-6-(3-fluoropyridin-4-yl)-1,2,4-triazin-3-amine (Intermediate II-2). LCMS: m/z = 395.2 [M + H]+. As hydrochloride. | In analogy to the preparation of Examples 8 to 13 of Table 2. By Cu -catalyzed cross-coupling instead of Pd -catalyzed cross-coupling as described in example 18, this table 4. |
| 46 | N-(3-tert-butyl-1H-1,2,4-triazol-5-yl)-5-(2-fluorophenyl)-6-(3-fluoropyridin-4-yl)-1,2,4-triazin-3-amine<br><br>[structure] | N-SEM protected heteroaryl bromide 5-bromo-3-tert-butyl-1-{[2-(trimethylsilyl)ethoxy]methyl}-1H-1,2,4-triazole and 5-(2-fluorophenyl)-6-(3-fluoropyridin-4-yl)-1,2,4-triazin-3-amine (Intermediate II-2). LCMS: m/z = 409.2 [M + H]+. As hydrochloride. | In analogy to the preparation of Examples 8 to 13 of Table 2. By Cu -catalyzed cross-coupling instead of Pd -catalyzed cross-coupling as described in example 18, this table 4. |
| 47 | 5-(2-fluorophenyl)-6-(3-fluoropyridin-4-yl)-N-[3-(1-methylcyclopropyl)-1H-1,2,4-triazol-5-yl]-1,2,4-triazin-3-amine | N-SEM protected heteroaryl bromide 5-bromo-3-(1-methylcyclopropyl)-1-{[2-(trimethylsilyl)ethoxy]methyl}-1H-1,2,4-triazole and 5-(2- | In analogy to the preparation of Examples 8 to 13 of Table 2. By Cu -catalyzed cross- |

TABLE 4-continued

| Ex No | Compound | Prepared from | Method / Procedure |
|---|---|---|---|
| | (structure: pyridine-F, triazine with 2-fluorophenyl and 3-fluoropyridin-4-yl, linked via NH to triazole bearing 1-methylcyclopropyl) | fluorophenyl)-6-(3-fluoropyridin-4-yl)-1,2,4-triazin-3-amine (Intermediate II-2). LCMS: m/z = 407.2 [M + H]$^+$. As hydrochloride. | coupling instead of Pd-catalyzed cross-coupling as described in example 18, this table 4. |
| 48 | 2-(5-{[5-(2-fluorophenyl)-6-(3-fluoropyridin-4-yl)-1,2,4-triazin-3-yl]amino}-1H-1,2,4-triazol-3-yl)propan-2-ol (structure: pyridine-F, triazine with 2-fluorophenyl and 3-fluoropyridin-4-yl, linked via NH to triazole bearing C(CH$_3$)$_2$OH) | N-SEM protected heteroaryl bromide 2-(5-bromo-1-{[2-(trimethylsilyl)ethoxy]methyl}-1H-1,2,4-triazol-3-yl)propan-2-ol and 5-(2-fluorophenyl)-6-(3-fluoropyridin-4-yl)-1,2,4-triazin-3-amine (Intermediate II-2). LCMS: m/z = 411.0 [M + H]$^+$. | In analogy to the preparation of Examples 8 to 13 of Table 2. By Cu-catalyzed cross-coupling instead of Pd-catalyzed cross-coupling as described in example 18, this table 4. |

*0.39 mmol intermediate II, CuI (0.23 mmol), 1N,2N-dimethylcyclohexane-1,2-diamine (0.23 mmol), N-SEM protected heteroaryl bromide (0.59 mmol), Caesium carbonate (1.2 eq), in DMA (2 ml) heating at 125° C. for 12 h under argon. Subsequent N-SEM deprotection of the coupling product with aq. HCl: (0.255 mmol scale), aq. conc HCl (5 ml), ethanol (10 ml), stirring for 2 h at 60° C.

Example 2

Biological Activity of Preferred Compounds of Formula I

Radioligand Binding Assays

For all four adenosine receptors (A1, A2A, A2B and A3) filtration binding assay was performed. Radioligand binding competition assay was done in duplicates in the wells of a 96-well plate (Master Block, Greiner, 786201) containing binding buffer, receptor membrane extracts, a fixed concentration of tracer and test compound at increasing concentrations. In order to eliminate effect of buffer components, binding buffer was the same for all four receptors and contained: 50 mM Tris-HCl pH 7.4, 5 mM MgCl$_2$, 1 mM EDTA, 150 mM NaCl, 0.1% Na-azide, and 5 U/ml adenosine-deaminase. Nonspecific binding was determined by co-incubation with 200-fold excess of cold competitor. In all radioligand binding experiments, the samples were incubated in a final volume of 0.1 ml for 60 minutes at 25° C. and then filtered over Unifilter plates (Perkin Elmer) pre-treated for 2 hours to limit tracer non-specific binding. Filters were washed five times with 0.5 ml of ice-cold washing buffer (50 mM Tris-HCl pH 7.4, 5 mM MgCl$_2$, 1 mM EDTA) and 50 μl of Microscint 20 (Perkin Elmer) were added to each filter. The plates are incubated 15 min at room temperature on an orbital shaker and then counted with a TopCount™ for 1 min/well.

For A1 receptor the assay was performed with [$^3$H]-DPCPX and membranes from CHO-K1 cells transfected with human A1 receptor (Euroscreen FAST-00B).

For A2A receptor the assay was performed with [$^3$H]-NECA and membranes from HEK293 cells transfected with human A2A receptor (Euroscreen FAST-002B).

For A2B, the assay was carried with [$^3$H]-DPCPX and membranes prepared from HEK293 cells transfected with human A2B receptor (Euroscreen FAST-003B).

For A3, the assay was carried out with [$^{125}$I]-MECA and membranes from CHO-K1 cells transfected with human A3 receptor (Euroscreen FAST-004B).

Intracellular cAMP Assays

Two assays have been employed, one using HEK293 with A2B receptors endogenously expressed (named cAMP assay (a) in the following) and a second one using HEK293 cells impressing recombinant human A2B receptors (named cAMP assay (b) in the following)

For cAMP Assay (a):

Real-time cAMP-assays in live cells were performed in HEK293 cells stably expressing the EPAC-sensor (I. Vedel, et al., 2015, J. Biomol. Screen. 20, 849-857). HEK293 cells have been shown to natively express A2B receptors (S-Hinz et al, J. Pharmaco.1 Exp. Ther. 2104, 249, 427).

In order to test for cAMP inhibition by preferred compounds of formula I and antagonists, respectively, from this invention, endogenous A2A and A2B expression in above cell lines was exploited. To run the assay, cells were incubated in 80 μl assay buffer for 15 minutes at room temperature. The assay buffer was composed of Hanks Balanced Salt Solution (Gibco) with 20 mM HEPES, pH 7.4 and 7.5 sg/ml adenosine-deaminase. All cAMP assays were run at room temperature using a PHERAstar FSX plate reader. The FRET donor (mCerulean) was excited at 430 nm. Fluorescence emission was measured at 480 nm and 530 nm for 65 minutes (cycle time 1.45 min). Prior to stimulation fluorescence was measured for 10 min (baseline). Subsequently cells were stimulated with 5 μM NECA (5'-(N-Ethylcarboxamido)adenosine; Tocris, Cat.-No:35920-39-9). Sharply 10.15 min after stimulation the compounds were added at increasing concentrations (between 0 and 200 µM) and fluorescence was recorded for 40 min. Each compound concentration was measured in duplicates.

For cAMP assay (b):

HEK293 cells expressing recombinant human A2B receptor, grown prior to the test in media without antibiotic, were detached by gentle flushing with PBS-EDTA (5 mM EDTA), recovered by centrifugation and resuspended in assay buffer (KRH: 5 mM KCl, 1.25 mM MgSO4, 124 mM NaCl, 25 mM HEPES, 13.3 mM Glucose, 1.25 mM KH2PO4, 1.45 mM CaCl2), 0.5 g/l BSA, supplemented with 1 mM IBMX or 25 µM Rolipram).

Dose response curves were performed in parallel with the reference compounds. 12 µl of cells were mixed with 6 µl of the test compound at increasing concentrations and then incubated 10 min. Thereafter 6 µl of the reference agonist was added at a final concentration corresponding to the historical EC80. The plates were then incubated for 30 min at room temperature. After addition of the lysis buffer and 1 hour incubation, cAMP concentrations were estimated, according to the manufacturer specification, with the HTRF kit.

Table 5 shows in vitro affinity data of selected compounds on human A2B receptors versus affinities on human A2A receptors demonstrating high selectivity for human A2B receptors over human A2A receptors.

TABLE 5

In vitro activity data on human A2B and A2A receptors (radioligand binding assays)

| Ex | Human A2B Receptor IC50, µM | Human A2A Receptor IC50, µM | Human A2B Receptor pKi | Human A2A Receptor pKi |
|---|---|---|---|---|
| 1 | 0.32 | 18.46 | 6.55 | 4.73 |
| 2 | 0.12 | 12.71 | 6.99 | 4.9 |
| 3 | 1.25 | | 5.95 | <4.70 |
| 4 | 0.36 | 3.28 | 6.5 | 5.48 |
| 5 | 4.66 | | 5.38 | <4.70 |
| 6 | 4.77 | | 5.37 | <4.70 |
| 7 | 6.32 | | 5.25 | <4.70 |
| 8 | 0.25 | 24.10 | 6.65 | 4.62 |
| 9 | 0.58 | 28% inhibition (50 µM) | 6.28 | <4.70 |
| 10 | 1.07 | | 6.02 | <4.70 |
| 11 | 1.01 | | 6.05 | <4.70 |
| 12 | 0.42 | 32.65 | 6.42 | 4.49 |
| 13 | 1.17 | | 5.98 | <4.70 |
| 14 | 0.46 | 54% I at 50 uM | 6.93 | <4.70 |
| 15 | 0.17 | 39.42 | 6.82 | 4.4 |
| 16 | 0.16 | 48% inhibition at 50 µM | 6.84 | <4.70 |
| 17 | | | 7.17 | 5.8 |
| 18 | | | 6.68 | |
| 21 | | | 7.81 | 6 |
| 22 | | | 7.95 | 4.7 |
| 23 | | | 7.43 | 6.57 |
| 24 | | | 7.33 | |
| 29 | | | 6.94 | |
| 31 | | | 7.27 | |
| 35 | | | 6.55 | |
| 36 | | | 7.42 | 6.56 |
| 37 | | | 7.84 | 6.1 |
| 38 | | | 7.65 | 5.84 |
| 39 | | | 7.76 | 5.66 |
| 40 | | | 7.89 | 6.25 |
| 44 | | | 7.58 | 6.00 |
| 46 | | | 7.01 | |

Table 6 shows in vitro affinity and activity data of selected compounds on human A1 and human A3 receptors (radioligand binding assays).

TABLE 6

| Ex | Human A1 Receptor IC50, µM | Human A1 Receptor pKi | Human A3 Receptor IC50, µM | Human A3 Receptor pKi |
|---|---|---|---|---|
| 1 | 19.01 | 5.02 | | |
| 2 | 7.44 | 5.43 | | |
| 8 | | | 1.35 | 5.99 |
| 14 | 2.20 | 5.96 | 27.12 | 4.68 |
| 15 | 1.18 | 6.23 | 43.48 | 4.48 |
| 16 | 3.79 | 5.73 | 9.52 | 5.14 |
| 18 | | 5.00 | | |
| 24 | | 5.58 | | |
| 31 | | 5.00 | | |
| 38 | | 6.26 | | 6.42 |
| 39 | | 6.19 | | 6.52 |

Biophysical Assays: A2B and A2A receptors used for biophysical measurements were produced using baculovirus mediated expression in insect cells. Expression constructs for both receptors contained point mutations that increased receptor thermal stability. Thermostabilised A2B and A2A receptors were solubilized using mild detergents (DDM and DM, respectively) and purified by standard purification methods. A2B receptor was purified in the buffer containing: 40 mM Tris-HCl pH 7.4, 200 mM NaCl, 0.05% DDM, and 0.005% CHS. A2A receptor was purified in the buffer containing: 40 mM Tris-HCl pH 7.4, 200 mM NaCl, 0.15% DM, and 0.002% CHS.

CPM Thermostability Assay

The compounds from the present invention were screened for A2B/A2A receptor binding and stabilization using CPM thermostability assay (A. I. Alexandrov, et al., 2008, Structure 16, 351-359). Protein concentration in the reaction was 1 µM, while the compound concentration for the data shown here was 10 µM. Final concentration of the CPM dye (Invitrogen D346) in the reaction was 7.5 µg/ml. The reaction buffer for A2B was 40 mM Tris-HCl pH 7.4, 200 mM NaCl, 0.05% DDM, and 0.005% CHS. The reaction buffer for A2A was 40 mM Tris-HCl pH 7.4, 200 mM NaCl, and 0.15% DDM. To allow for binding, compounds were incubated with the purified receptor for 30 minutes on ice before addition of the CPM dye. Measurements were performed using Rotor-Gene Q qPCR instrument (QIAGEN). The temperature was ramped from 25° C. to 90° C. with 6° C. increase per minute. The gain was set to the first sample in the run which was always a protein without ligand that was used as a reference. CPM dye binding was monitored using 365 nm excitation and 460 nm emission. The data was analyzed with the instrument software and the melting temperatures were calculated as an average of each duplicate (duplicates on averages did not differ for more than 0.5° C.). Increase in the melting temperature ($\Delta$Tm) i.e. thermal shift value for each compound was calculated by subtracting the melting temperate of the apo receptor from the melting temperature of the receptor bound to a respective compound.

Wave Guided Interferometry (WGI)

WGI experiments with A2B receptor were performed using the Wave delta instrument (Creoptix AG), a label free surface biosensor. Purified A2B protein was immobilized on 4PCP-N chips (Creoptix, quasi planar NTA functionalized polycarboxylate surface) at typical levels between 3500-5000 µg/mm$^2$. Running buffer was 25 mM Tris-HCl pH 7.5, 350 mM NaCl, 0.1% DDM, and 2% DMSO. The procedure started with 40 start-up cycles in order to equilibrate and stabilize the surface. Once start-up cycles were performed, different concentrations of compounds (diluted in running buffer, and adjusted depending on the kinetic characteristics)

were injected in a multi cycle kinetic mode with typical association time of 120 s and dissociation time of 240 s. A DMSO calibration (typically 5 concentrations between 1 and 3% DMSO) was performed for every experiment in order to calibrate DMSO levels as well as to estimate the missing volume taken by the protein on the chip. Data were evaluated with Creoptix Wave software (Creoptix AG). All final signals are double referenced with injections of same compound concentrations on a reference channel and with buffer injections on the active channel (where protein is immobilized) and fitted with a 1:1 interaction model in order to obtain $K_D$ values.

Table 7 shows the activity of preferred inventive compounds with human thermostabilized A2B receptor in the biophysical CPM assay of receptor stabilization with activity expressed as ΔTm and in the WGI assay with kinetic binding affinity expressed as Kd.

TABLE 7

Biophysical assays with human thermostabilised A2B receptor

| Example | $K_D$ WGI (μM) | ΔTm CPM (10 μM) |
|---|---|---|
| 1 | 0.5 | 7.3 |
| 2 | 1 | 7.5 |
| 3 |  | 7 |
| 4 | 1 | 6.2 |
| 5 |  | 7.6 |
| 6 |  | 5.6 |
| 7 |  | 6.6 |
| 8 | 0.13 | 11.3 |
| 9 | 0.7 | 9.4 |
| 10 |  | 7.6 |
| 11 | 0.47 | 7.9 |
| 12 |  | 7.1 |
| 13 |  | 6.5 |
| 14 | 0.24 | 7.9 |
| 15 | 0.12 | 9.5 |
| 16 | 0.10 | 10.7 |
| 17 |  | 10.3 |
| 21 |  | 13.0 |
| 22 |  | 14.5 |
| 23 |  | 11.3 |
| 24 |  | 12.5 |
| 28 |  | 7.0 |
| 29 |  | 10.2 |
| 30 |  | 6.6 |
| 35 |  | 10.5 |
| 36 |  | 11.6 |
| 37 |  | 13.5 |
| 38 |  | 13.3 |
| 39 |  | 13.1 |
| 40 |  | 13.9 |
| 41 |  | 9.8 |
| 42 |  | 11.0 |
| 43 |  | 9.4 |
| 44 |  | 11.4 |
| 45 |  | 10.4 |
| 46 |  | 14 |
| 47 |  | 9.9 |
| 48 |  | 9.6 |

Table 8a shows the activity of selected molecules in functional cAMP accumulation assay in HEK293 cells (cAMP assay (a))

TABLE 8a

EC50 cAMP assay (a), HEK293 cells

| Example | cAMP EC50 (μM) | cAMP pIC50 |
|---|---|---|
| 1 | 0.40 | 6.40 |
| 2 | 0.63 | 6.20 |
| 3 | 2.00 | 5.70 |
| 6 | 3.98 | 5.40 |
| 7 | 6.92 | 5.16 |

Table 8b shows the activity of selected molecules in functional cAMP accumulation assay in HEK293 cells (cAMP assay (b))

TABLE 8b

EC50 cAMP assay (b), HEK293 cells

| Example | cAMP pIC50 |
|---|---|
| 15 | 6.3 |
| 17 | 6.49 |
| 21 | 7.18 |
| 22 | 7.53 |
| 23 | 6.98 |
| 24 | 6.97 |
| 31 | 6.56 |
| 38 | 7.30 |
| 39 | 7.38 |

The invention claimed is:

1. A compound of formula I

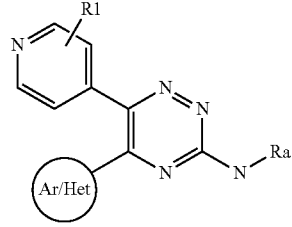

or a pharmaceutically acceptable salt or hydrate thereof, wherein said compound is a compound of formula Ia, formula Ib or formula Ic, wherein $R_2$ is selected from hydrogen, $C_1$-$C_8$ alkyl, halogen and $C_1$-$C_8$ alkoxy:

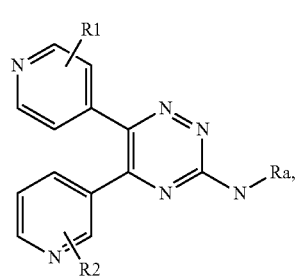

-continued
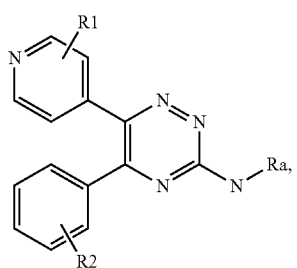
Ib
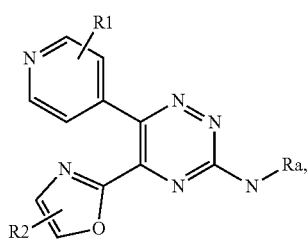
Ic
wherein said Ra is selected from the group consisting of:
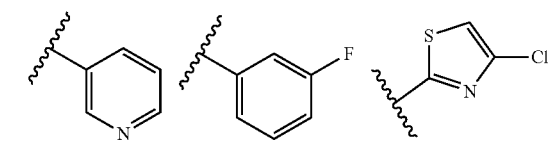
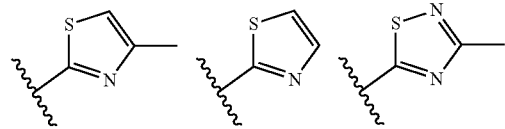
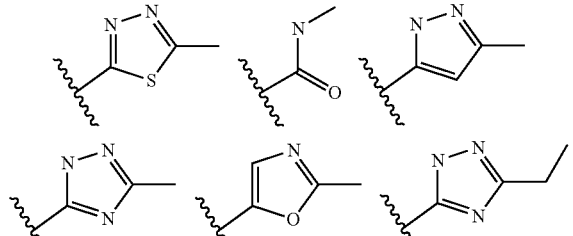
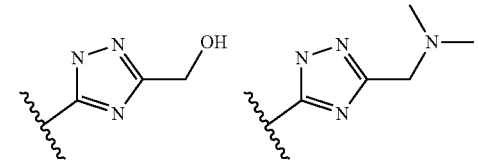
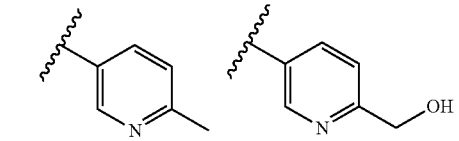
-continued
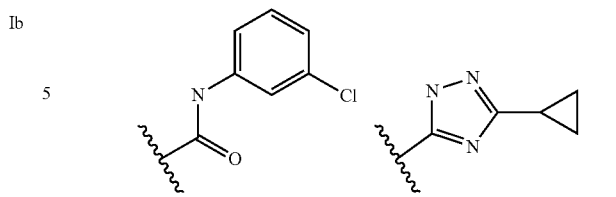
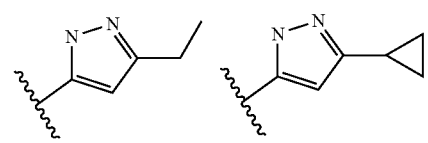
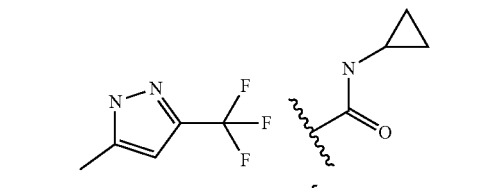
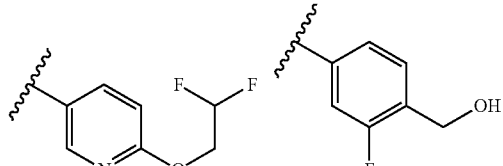
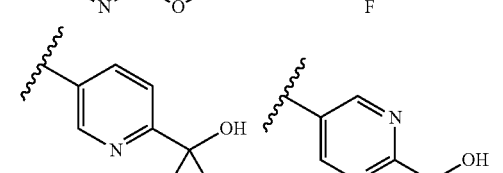
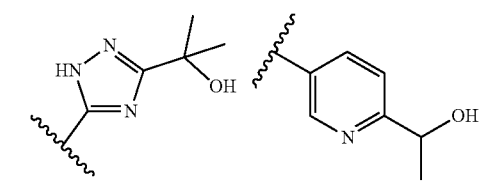

-continued

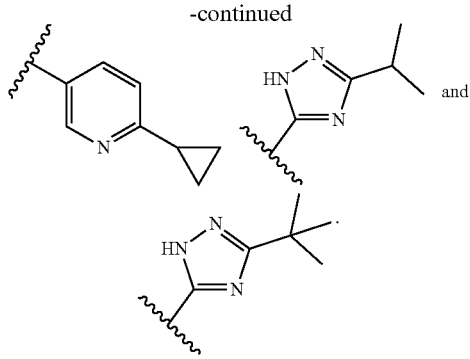

wherein said R1 is selected from hydrogen, halogen, $C_1$-$C_2$alkyl, $C_1$-$C_2$haloalkyl, $C_1$-$C_2$alkoxy, $C_1$-$C_2$hydroxyalkyl and $C_1$-$C_2$alkoxyalkyl.

2. The compound of claim 1, wherein said R2 is selected from hydrogen, $C_1$-$C_2$alkyl, halogen and $C_1$-$C_2$alkoxyl.

3. The compound of claim 1, wherein
said R1 is selected from hydrogen, halogen and $C_1$-$C_2$ haloalkyl; and
said R2 is selected from hydrogen, $C_1$-$C_2$alky and halogen.

4. The compound of claim 1, wherein said compound is selected from
6-(3-fluoropyridin-4-yl)-N,5-di(pyridin-3-yl)-1,2,4-triazin-3-amine;
N-(3-fluorophenyl)-6-(3-fluoropyridin-4-yl)-5-(pyridin-3-yl)-1,2,4-triazin-3-amine;
N-(6 (3-fluoropyridin-4-yl)-5-(pyridin 3-yl)-1,2,4-triazin-3-yl) thiazol-2-amine;
4-chloro-N-(6-(3-fluoropyridin-4-yl)-5-(pyridin-3-yl)-1,2,4-triazin-3-yl) thiazol-2-amine;
N-(6-(3-fluoropyridin-4-yl)-5-(pyridin-3-yl)-1,2,4-triazin-3-yl)-3-methyl-1,2,4-thiadiazol-5-amine;
N-(6-(3-fluoropyridin-4-yl) 5-(pyridin-3-yl)-1,2,4-triazin 3-yl) 5-methyl-1,3,4-thiadiazol-2-amine;
1-(6-(3-fluoropyridin-4-yl)-5-(pyridin-3-yl)-1,2,4-triazin-3-yl)-3-methylurea;
5-(2-fluorophenyl)-N-(pyridin-3 yl)-6-(2-(trifluoromethyl) pyridin-4-yl)-1,2,4-triazin-3-amine;
5-(2-fluorophenyl)-N-(pyridin-3-yl)-6-(2-(trifluoromethyl) pyridin-4-yl)-1,2,4-triazin-3-amine;
4-chloro-N-(5-(2-fluorophenyl)-6-(2-(trifluoromethyl) pyridin-4-yl) 1,2,4-triazin-3-yl) thiazol-2-amine;
N-(5-(2-fluorophenyl)-6-(2-(trifluoromethyl) pyridin-4-yl)-1,2,4-triazin-3-yl)-3-methyl-1,2,4-thiadiazol-S-amine;
5-(2-fluorophenyl)-N-(3-fluorophenyl)-6-(3-fluoropyridin-4-yl)-1,2,4-triazin-3-amine;
N-(5-(2-fluorophenyl)-6 (3-fluoropyridin-4-yl)-1,2,4-triazin-3-yl)-3-methyl-1,2,4-thiadiazol-5-amine;
5-(2-fluorophenyl)-6-(3-fluoropyridin-4-yl)-N-(3-methyl-1H-pyrazol-5-yl)-1,2,4-triazin-3-amine;
5-(2-fluorophenyl)-6-(3-fluoropyridin-4-yl)-N-(3-methyl-1H-1,2,4-triazol-5-yl)-1,2,4-triazin-3-amine;
5-(2-fluorophenyl)-6-(3-fluoropyridin-4-yl-N-[3-(1-methylcyclopropyl)-1H-1,2,4-triazol-5-yl]-1,2,4-triazin-3-amine; and
2-(5-{[5-(2-fluorophenyl)-6-(3-fluoropyridin-4-yl)-1,2,4-triazin-3-yl]amino}-1H-1,2,4-triazol-3-yl)propan-2-ol.

5. A pharmaceutical composition comprising a compound according to claim 1, and a pharmaceutically acceptable diluent or carrier.

* * * * *

UNITED STATES PATENT AND TRADEMARK OFFICE
CERTIFICATE OF CORRECTION

PATENT NO. : 12,391,670 B2
APPLICATION NO. : 17/287467
DATED : August 19, 2025
INVENTOR(S) : Werner Neidhart and Denis Bucher Page 1 of 3

It is certified that error appears in the above-identified patent and that said Letters Patent is hereby corrected as shown below:

In the Claims

Claim 4, Column 91, Line 28 to Column 92, Line 29 replace:
"6-(3-fluoropyridin-4-yl)-N,5-di(pyridin-3-yl)-1,2,4-triazin-3-amine;
N-(3-fluorophenyl)-6-(3-fluoropyridin-4-yl)-5-(pyridin-3-yl)-1,2,4-triazin-3-amine;
N-(6-(3-fluoropyridin-4-yl)-5-(pyridin-3-yl)-1,2,4-triazin-3-yi)thiazol-2-amine;
4-chloro-N-(6-(3-fluoropyridin-4-yl)-5-(pyridin-3-yl)-1,2,4-triazin-3-yl)thiazol-2-amine;
N-(6-(3-fluoropyridin-4-yl)-5-(pyridin-3-yl)-1,2,4-triazin-3-yl)-3-methyl-1,2,4-thiadiazol-5-amine;
N-(6-(3-fluoropyridin-4-yl)-5-(pyridin-3-yl)-1,2,4-triazin-3-yl)-5-methyl-1,3,4-thiadiazol-2-amine:
1-(6-(3-fluoropyridin-4-yl)-5-(pyridin-3-yl)-1,2,4-triazin-3-yl)-3-methylurea;
5-(2-fluorophenyl)-N-(pyridin-3-yl)-6-(2-(trifluoromethyl)pyridin-4-yl)-1,2,4-triazin-3-amine;
5-(2-fluorophenyl)-N-(pyridin-3-yl)-6-(2-(trifluoromethyl)pyridin-4-yl)-1,2,4-triazin-3-amine;
4-chloro-N-(5-(2-fluorophenyl)-6-(2-(trifluoromethyl)pyridin-4-yl)-1,2,4-triazin-3-yl)thiazol-2-amine;
N-(5-(2-fluorophenyl)-6-(2-(trifluoromethyl)pyridin-4-yl)-1,2,4-triazin-3-yl)-3-methyl-1,2,4-thiadiazol-5-amine;
5-(2-fluorophenyl)-N-(3-fluorophenyl)-6-(3-fluoropyridin-4-yl)-1,2,4-triazin-3-amine;
N-(5-(2-fluorophenyl)-6-(3-fluoropyridin-4-yl)-1,2,4-triazin-3-yl)-3-methyl-1,2,4-thiadiazol-5-amine;
5-(2-fluorophenyl)-6-(3-fluoropyridin-4-yl)-N-(3-methyl-1H-pyrazol-5-yl)-1,2,4-triazin-3-amine;
5-(2-fluorophenyl)-6-(3-fluoropyridin-4-yl)-N-(3-methyl-1H-1,2,4-triazol-5-yl)-1,2,4-triazin-3-amine;
5-(2-fluorophenyl)-6-(3-fluoropyridin-4-yl)-N-[3-(1-methylcyclopropyl)-1H-1,2,4-triazol-5-yl]-1,2,4-triazin-3-amine;
and
2-(5-([5-(2-fluorophenyl)-6-(3-fluoropyridin-4-yl)-1,2,4-triazin-3-yl]amino}-1H-1,2,4-triazol-3-yl)propan-2-ol."

With:
--6-(3-fluoropyridin-4-yl)-N,5-di(pyridin-3-yl)-1,2,4-triazin-3-amine;
N-(3-fluorophenyl)-6-(3-fluoropyridin-4-yl)-5-(pyridin-3-yl)-1,2,4-triazin-3-amine;

Signed and Sealed this
Eleventh Day of November, 2025

John A. Squires
*Director of the United States Patent and Trademark Office*

N-(6-(3-fluoropyridin-4-yl)-5-(pyridin-3-yl)-1,2,4-triazin-3-yl)thiazol-2-amine;
4-chloro-N-(6-(3-fluoropyridin-4-yl)-5-(pyridin-3-yl)-1,2,4-triazin-3-yl)thiazol-2-amine;
N-(6-(3-fluoropyridin-4-yl)-5-(pyridin-3-yl)-1,2,4-triazin-3-yl)-3-methyl-1,2,4-thiadiazol-5-amine;
N-(6-(3-fluoropyridin-4-yl)-5-(pyridin-3-yl)-1,2,4-triazin-3-yl)-5-methyl-1,3,4-thiadiazol-2-amine:
1-(6-(3-fluoropyridin-4-yl)-5-(pyridin-3-yl)-1,2,4-triazin-3-yl)-3-methylurea;
5-(2-fluorophenyl)-N-(pyridin-3-yl)-6-(2-(trifluoromethyl)pyridin-4-yl)-1,2,4-triazin-3-amine;
5-(2-fluorophenyl)-N-(pyridin-3-yl)-6-(2-(trifluoromethyl)pyridin-4-yl)-1,2,4-triazin-3-amine;
4-chloro-N-(5-(2-fluorophenyl)-6-(2-(trifluoromethyl)pyridin-4-yl)-1,2,4-triazin-3-yl)thiazol-2-amine;
N-(5-(2-fluorophenyl)-6-(2-(trifluoromethyl)pyridin-4-yl)-1,2,4-triazin-3-yl)-3-methyl-1,2,4-thiadiazol-5-amine;
5-(2-fluorophenyl)-N-(3-fluorophenyl)-6-(3-fluoropyridin-4-yl)-1,2,4-triazin-3-amine;
N-(5-(2-fluorophenyl)-6-(3-fluoropyridin-4-yl)-1,2,4-triazin-3-yl)-3-methyl-1,2,4-thiadiazol-5-amine;
5-(2-fluorophenyl)-6-(3-fluoropyridin-4-yl)-N-(3-methyl-1H-pyrazol-5-yl)-1,2,4-triazin-3-amine;
5-(2-fluorophenyl)-6-(3-fluoropyridin-4-yl)-N-(3-methyl-1H-1,2,4-triazol-5-yl)-1,2,4-triazin-3-amine;
1-(5-(2-fluorophenyl)-6-(3-fluoropyridin-4-yl)-1,2,4-triazin-3-yl)-3-methylurea;
N-(3-fluorophenyl)-6-(3-fluoropyridin-4-yl)-5-(5-methyloxazol-2-yl)-1,2,4-triazin-3-amine;
N-(3-ethyl-1H-1,2,4-triazol-5-yl)-5-(2-fluorophenyl)-6-(3-fluoro-4-pyridyl)-1,2,4-triazin-3-amine;
[5-[[5-(2-fluorophenyl)-6-(3-fluoro-4-pyridyl)-1,2,4-triazin-3-yl]amino]-1H-1,2,4-triazol-3-yl]methanol;
N-[3-[(dimethylamino)methyl]-1H-1,2,4-triazol-5-yl]-5-(2-fluorophenyl)-6-(3-fluoro-4-pyridyl)-1,2,4-triazin-3-amine;
5-(2-fluorophenyl)-6-(3-fluoro-4-pyridyl)-N-(6-methyl-3-pyridyl)-1,2,4-triazin-3-amine;
[5-[[5-(2-fluorophenyl)-6-(3-fluoro-4-pyridyl)-1,2,4-triazin-3-yl]amino]-2-pyridyl]methanol;
5-(2-fluorophenyl)-6-(3-fluoro-4-pyridyl)-N-(6-methoxy-3-pyridyl)-1,2,4-triazin-3-amine;
5-(2-fluorophenyl)-6-(3-fluoro-4-pyridyl)-N-[6-(trifluoromethyl)-3-pyridyl]-1,2,4-triazin-3-amine;
1-(3-chlorophenyl)-3-[6-(3-fluoro-4-pyridyl)-5-(3-pyridyl)-1,2,4-triazin-3-yl]urea;
1-[6-(3-fluoro-4-pyridyl)-5-(3-pyridyl)-1,2,4-triazin-3-yl]-3-(4-methoxyphenyl)urea;
1-[6-(3-fluoro-4-pyridyl)-5-(3-pyridyl)-1,2,4-triazin-3-yl]-3-(2-morpholinoethyl)urea;
1-(3-chlorophenyl)-3-[5-(2-fluorophenyl)-6-(3-fluoro-4-pyridyl)-1,2,4-triazin-3-yl]urea;
1-[5-(2-fluorophenyl)-6-(3-fluoro-4-pyridyl)-1,2,4-triazin-3-yl]-3-(4-methoxyphenyl)urea;
1-[5-(2-fluorophenyl)-6-(3-fluoro-4-pyridyl)-1,2,4-triazin-3-yl]-3-(2-morpholinoethyl)urea;
N-(3-cyclopropyl-1H-1,2,4-triazol-5-yl)-5-(2-fluorophenyl)-6-(3-fluoro-4-pyridyl)-1,2,4-triazin-3-amine;
5-(2-fluorophenyl)-6-(3-fluoro-4-pyridyl)-N-[3-(trifluoromethyl)-1H-pyrazol-5-yl]-1,2,4-triazin-3-amine;
N-(3-ethyl-1H-pyrazol-5-yl)-5-(2-fluorophenyl)-6-(3-fluoro-4-pyridyl)-1,2,4-triazin-3-amine;
N-(3-cyclopropyl-1H-pyrazol-5-yl)-5-(2-fluorophenyl)-6-(3-fluoro-4-pyridyl)-1,2,4-triazin-3-amine;
1-cyclopropyl-3-[5-(2-fluorophenyl)-6-(3-fluoro-4-pyridyl)-1,2,4-triazin-3-yl]urea;
N-[6-(2,2-difluoroethoxy)pyridin-3-yl]-5-(2-fluorophenyl)-6-(3-fluoropyridin-4-yl)-1,2,4-triazin-3-amine;
2-fluoro-4-{[5-(2-fluorophenyl)-6-(3-fluoropyridin-4-yl)-1,2,4-triazin-3-yl]amino}phenyl)methanol;
2-(5-{[5-(2-fluorophenyl)-6-(3-fluoropyridin-4-yl)-1,2,4-triazin-3-yl]amino}pyridin-2-yl)propan-2-ol;
(5-{[5-(2-fluorophenyl)-6-(3-fluoropyridin-4-yl)-1,2,4-triazin-3-yl]amino}pyrimidin-2-yl)methanol;

1-(5-{[5-(2-fluorophenyl)-6-(3-fluoropyridin-4-yl)-1,2,4-triazin-3-yl]amino}pyridin-2-yl)ethan-1-ol;
3-(5-{[5-(2-fluorophenyl)-6-(3-fluoropyridin-4-yl)-1,2,4-triazin-3-yl]amino}pyridin-2-yl)oxetan-3-ol;
5-(2-fluorophenyl)-6-(3-fluoropyridin-4-yl)-N-[6-(propan-2-yl)pyridin-3-yl]-1,2,4-triazin-3-amine;
1-(5-{[5-(2-fluorophenyl)-6-(3-fluoropyridin-4-yl)-1,2,4-triazin-3-yl]amino}pyridin-2-yl)-2-methylpropan-1-ol;
N-(6-cyclopropylpyridin-3-yl)-5-(2-fluorophenyl)-6-(3-fluoropyridin-4-yl)-1,2,4-triazin-3-amine;
5-(2-fluorophenyl)-6-(3-fluoropyridin-4-yl)-N-[3-(propan-2-yl)-1H-1,2,4-triazol-5-yl]-1,2,4-triazin-3-amine;
N-(3-tert-butyl-1H-1,2,4-triazol-5-yl)-5-(2-fluorophenyl)-6-(3-fluoropyridin-4-yl)-1,2,4-triazin-3-amine;
5-(2-fluorophenyl)-6-(3-fluoropyridin-4-yl)-N-[3-(1-methylcyclopropyl)-1H-1,2,4-triazol-5-yl]-1,2,4-triazin-3-amine; and
2-(5-{[5-(2-fluorophenyl)-6-(3-fluoropyridin-4-yl)-1,2,4-triazin-3-yl]amino}-1H-1,2,4-triazol-3-yl)propan-2-ol.--